United States Patent
Chang et al.

(10) Patent No.: US 9,272,029 B2
(45) Date of Patent: Mar. 1, 2016

(54) INTERFERON LAMBADA-ANTIBODY COMPLEXES

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); Donglin Liu, Kendall Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 14 days.

(21) Appl. No.: 13/749,985

(22) Filed: Jan. 25, 2013

(65) Prior Publication Data
US 2013/0136718 A1  May 30, 2013

Related U.S. Application Data

(60) Continuation-in-part of application No. 13/412,816, filed on Mar. 6, 2012, now Pat. No. 8,435,540, which is a division of application No. 13/178,092, filed on Jul. 7, 2011, now Pat. No. 8,158,129, which is a continuation-in-part of application No. 12/731,781, filed on Mar. 25, 2010, now Pat. No. 8,003,111.

(60) Provisional application No. 61/591,087, filed on Jan. 26, 2012, provisional application No. 61/163,666, filed on Mar. 26, 2009.

(51) Int. Cl.
| | |
|---|---|
| A61K 39/395 | (2006.01) |
| A61K 47/48 | (2006.01) |
| C07K 14/555 | (2006.01) |
| C07K 16/00 | (2006.01) |
| C07K 16/30 | (2006.01) |
| C07K 16/28 | (2006.01) |
| C07K 16/46 | (2006.01) |
| G01N 33/68 | (2006.01) |
| B82Y 30/00 | (2011.01) |

(52) U.S. Cl.
CPC .......... *A61K 39/395* (2013.01); *A61K 47/48215* (2013.01); *A61K 47/48246* (2013.01); *A61K 47/48423* (2013.01); *A61K 47/48576* (2013.01); *C07K 14/555* (2013.01); *C07K 16/00* (2013.01); *C07K 16/005* (2013.01); *C07K 16/283* (2013.01); *C07K 16/3007* (2013.01); *C07K 16/468* (2013.01); *G01N 33/6866* (2013.01); *B82Y 30/00* (2013.01); *C07K 2317/31* (2013.01); *C07K 2317/55* (2013.01); *C07K 2317/73* (2013.01); *C07K 2319/30* (2013.01); *C07K 2319/33* (2013.01); *C07K 2319/70* (2013.01)

(58) Field of Classification Search
CPC .......... A61K 39/395; A61K 47/48569; A61K 47/48246; C07K 14/555; C07K 16/00; C07K 16/30; C07K 2319/33; C07K 2319/00
See application file for complete search history.

(56) References Cited

U.S. PATENT DOCUMENTS

| | | | |
|---|---|---|---|
| 4,046,722 | A | 9/1977 | Rowland |
| 4,699,784 | A | 10/1987 | Shih et al. |
| 4,868,109 | A | 9/1989 | Lansdorp et al. |
| 5,770,198 | A | 6/1998 | Coller et al. |
| 6,261,537 | B1 | 7/2001 | Klaveness et al. |
| 6,306,393 | B1 | 10/2001 | Goldenberg et al. |
| 6,524,854 | B1 | 2/2003 | Monia et al. |
| 7,060,506 | B2 | 6/2006 | Craig |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,550,143 | B2 | 6/2009 | Chang et al. |
| 7,666,400 | B2 | 2/2010 | Chang et al. |
| 7,858,070 | B2 | 12/2010 | Chang et al. |
| 7,871,622 | B2 | 1/2011 | Chang et al. |
| 7,901,680 | B2 | 3/2011 | Chang et al. |
| 7,906,121 | B2 | 3/2011 | Chang et al. |
| 7,981,398 | B2 | 7/2011 | Chang et al. |
| 8,003,111 | B2 | 8/2011 | Chang et al. |
| 8,034,352 | B2 | 10/2011 | Chang et al. |

(Continued)

FOREIGN PATENT DOCUMENTS

| | | |
|---|---|---|
| WO | 00/68248 | 11/2000 |
| WO | 2006/107617 | 10/2006 |

(Continued)

OTHER PUBLICATIONS

Amet, N. et al. Insertion of the designed helical linker led to increased expression of Tf-based fusion proteins. Pharm. Res., 2009, vol. 26, No. 3, p. 523-528.*

Chen, X. et al. Design of an in vivo cleavable disulfide linker in recombinant fusion proteins. BioTechniques. 2010, vol. 49, p. 513-518.*

Matarrese et al., "Type I Interferon Gene Transfer Sensitizes Melanoma Cells to Apoptosis via a Target Activity on Mitochondrial Function" Am. J. Pathol. 2002, 160(4):1507-1520.

(Continued)

*Primary Examiner* — Robert Landsman
*Assistant Examiner* — Bruce D Hissong
(74) *Attorney, Agent, or Firm* — Richard A. Nakashima

(57) ABSTRACT

The present invention concerns methods and compositions for forming complexes of interferon-λ with an antibody or antigen-binding antibody fragment. In preferred embodiments, the interferon-λ and the antibody or fragment are fusion proteins, each comprising a dimerization and docking domain (DDD) moiety from human protein kinase A or an anchor domain (AD) moiety from an A-kinase anchoring protein (AKAP). In more preferred embodiments, the interferon-antibody complex is more efficacious for treatment of cancer, asthma, Alzheimer's disease, multiple sclerosis or viral infection than interferon-λ alone, antibody alone, or the combination of unconjugated interferon-λ and antibody.

6 Claims, 16 Drawing Sheets

(56) References Cited

U.S. PATENT DOCUMENTS

| | | | |
|---|---|---|---|
| 8,158,129 | B2 | 4/2012 | Chang et al. |
| 8,163,291 | B2 | 4/2012 | Chang et al. |
| 8,211,440 | B2 | 7/2012 | Chang et al. |
| 8,246,960 | B2 | 8/2012 | Chang et al. |
| 8,277,817 | B2 | 10/2012 | Chang et al. |
| 8,282,934 | B2 | 10/2012 | Chang et al. |
| 8,349,332 | B2 | 1/2013 | Chang et al. |
| 8,435,540 | B2 | 5/2013 | Chang et al. |
| 8,475,794 | B2 | 7/2013 | Chang et al. |
| 8,481,041 | B2 | 7/2013 | Chang et al. |
| 8,491,914 | B2 | 7/2013 | Chang et al. |
| 8,551,480 | B2 | 10/2013 | Chang et al. |
| 8,562,988 | B2 | 10/2013 | Chang et al. |
| 8,597,659 | B2 | 12/2013 | Chang et al. |
| 2003/0198956 | A1 | 10/2003 | Makowski et al. |
| 2003/0232420 | A1 | 12/2003 | Braun et al. |
| 2004/0018587 | A1 | 1/2004 | Makowski et al. |
| 2004/0126361 | A1 | 7/2004 | Saifer et al. |
| 2005/0003403 | A1 | 1/2005 | Rossi et al. |
| 2006/0210475 | A1 | 9/2006 | Goldenberg et al. |
| 2006/0228300 | A1* | 10/2006 | Chang et al. ............. 424/1.49 |
| 2007/0086942 | A1 | 4/2007 | Chang et al. |
| 2007/0264265 | A1 | 11/2007 | Goldenberg et al. |
| 2009/0111143 | A1 | 4/2009 | Goldenberg et al. |
| 2009/0202487 | A1* | 8/2009 | Chang et al. ............. 424/85.7 |
| 2011/0020273 | A1 | 1/2011 | Chang et al. |
| 2011/0064653 | A1 | 3/2011 | Hansen et al. |
| 2011/0064754 | A1 | 3/2011 | Taylor et al. |
| 2011/0143417 | A1 | 6/2011 | Chang et al. |
| 2011/0158905 | A1 | 6/2011 | Goldenberg et al. |
| 2011/0189083 | A1 | 8/2011 | Chang et al. |
| 2011/0263832 | A1 | 10/2011 | Kranz et al. |
| 2012/0093769 | A1 | 4/2012 | Chang et al. |
| 2012/0196346 | A1 | 8/2012 | Chang et al. |
| 2012/0276100 | A1 | 11/2012 | Chang et al. |
| 2012/0276608 | A1 | 11/2012 | Chang et al. |
| 2013/0078183 | A1 | 3/2013 | Chang et al. |
| 2013/0109073 | A1 | 5/2013 | Chang et al. |
| 2013/0164816 | A1 | 6/2013 | Chang et al. |
| 2013/0177532 | A1 | 7/2013 | Chang et al. |
| 2013/0217091 | A1 | 8/2013 | Chang et al. |
| 2013/0295005 | A1 | 11/2013 | Chang et al. |

FOREIGN PATENT DOCUMENTS

| | | |
|---|---|---|
| WO | 2006/107786 | 10/2006 |
| WO | 2007/046893 | 4/2007 |
| WO | 2007/075270 | 7/2007 |
| WO | 2011147982 A2 | 12/2011 |

OTHER PUBLICATIONS

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Newlon et al., "A Novel Mechanism of PKA Anchoring Revealed by Solution Structures of Anchoring Complexes" EMBO J. 2001; 20:1651-1662.

Newlon et al., "The molecular basis for protein kinase A anchoring revealed by solution NMR" Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Oyen et al., "Human testis cDNA for the regulatory subunit RIIα of cAMP-dependent protein kinase encodes an alternate amino-terminal region" FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).

Paquette et al., "Interferon-A and granulocyte-macrophage colony-stimulating factor differentiate peripheral blood monocytes into potent antigen-presenting cells" J. Leukoc. Biol. 64:358-367; 1998.

Pelham et al., "Interferon-A conjugation to human osteogenic sarcoma monoclonal antibody 791T/36" Cancer Immunol. Immuother. 1983;15(3):210-216.

Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.

Pilling et al., "Interferon-β mediates stromal cell rescue of T cells from apoptosis" Eur. J. Immunol. 29:1041-1050 (1999).

Rabjohn et al., "Molecular Cloning and Epitope Analysis of the Peanut Allergen Ara h 3" J. Clinical Investigation 103 (4):535-542 (1999).

Raefsky et al., "Studies of Interferon as a regulator of hematopoietic cells proliferation" J. Immunol. 135 (4):2507-2512 (1985).

Rose et al., "Structural basis of dimerization, coactivator recognition and MODY3 mutations in HNF-1α" Nature Struct. Biol. 2000; 7:744-748.

Rosendahl et al., "A Long-Acting, Highly Potent Interferon α-2 Conjugate Created Using Site-Specific PEGylation" Bioconjugate Chem. 2005;16:200-207.

Rossi et al., "Novel Designs of Multivalent Anti-CD20 Humanized Antibodies as Improved Lymphoma Therapeutics" Cancer Res. 68:8384-92 (2008).

Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Rustandi et al., "The Ca2+-Dependent Interaction of S100B(ββ) with a Peptide Derived from p53", Biochemistry 1998; 37: 1951-1960.

Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.

Salles et al., "Rituximab combined with chemotherapy and interferon in follicular lymphoma patients: results of the GELA-GOELAMS FL2000 study" Blood 2008; 112:4824-4831.

Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).

Scott et al., "Type II Regulatory Subunit Dimerization Determines the Subcellular Localization of the cAMP-dependent Protein Kinase" J. Biol. Chem. 265:21561-66 (1990).

Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).

Sharkey et al., "Improved Therapeutic Results by Pretargeted Radioimmunotherapy of Non-Hodgkin's Lymphoma with a New Recombinant, Trivalent, Anti-CD20, Bispecific Antibody" Cancer Res. 68:5282-90 (2008).

Sharkey et al., "Metastatic Human Colonic Carcinoma: Molecular Imaging with Pretargeted SPECT and PET in a Mouse Model" Radiology 246:497-507 (2008).

Sidky et al., "Inhibition of Angiogenesis by Interferons: Effects on Tumor- and Lymphocyte-induced Vascular Responses" Cancer Res. 47:5155-5161, Oct. 1, 1987.

Stein et al., "Characterization of a New Humanized Anti-CD20 Monoclonal Antibody, IMMU-106, and its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

(56) References Cited

OTHER PUBLICATIONS

Taylor, S., "cAMP-dependent Protein Kinase" J. Biol. Chem. 1989;264(15):8443-8446.
Walsh et al., "An Adenosine 3', 5'-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody" J. Immunol. 165:4505-14 (2000).
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time" Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor" Invest. New Drugs 17:195-212, 1999.
Abushahba et al., "Antitumor activity of type I and type III interferons in BNL hepatoma model", Cancer Immunol Immunother. Jul. 2010;59(7):1059-71.
Ank et al., "IFN-lambda: novel antiviral cytokines", J Interferon Cytokine Res. Jun. 2006;26(6):373-9.
Ank et al., "Lambda interferon (IFN-lambda), a type III IFN, is induced by viruses and IFNs and displays potent antiviral activity against select virus infections in vivo", J Virol. May 2006;80(9):4501-9.
Ank et al., "An important role for type III interferon (IFN-lambda/IL-28) in TLR-induced antiviral activity", J Immunol. Feb. 15, 2008;180(4):2474-85.
Billiau, A., "Interferon: the pathways of discovery I. Molecular and cellular aspects", Cytokine Growth Factor Rev. Oct. 2006;17(5):381-409. Epub Aug. 22, 2006.
Chang et al., "A new method to produce monoPEGylated dimeric cytokines shown with human interferon-α2b", Bioconjug Chem. Oct. 21, 2009;20(10):1899-907.
Cohen et al., "Alemtuzumab versus interferon beta 1a as first-line treatment for patients with relapsing-remitting multiple sclerosis: a randomised controlled phase 3 trial", Lancet. Nov. 24, 2012;380(9856):1819-28.
Coles et al., "Alemtuzumab versus interferon β-1a in early relapsing-remitting multiple sclerosis: post-hoc and subset analyses of clinical efficacy outcomes", Lancet Neurol. Apr. 2011;10(4):338-48.
Coles et al., "Alemtuzumab for patients with relapsing multiple sclerosis after disease-modifying therapy: a randomised controlled phase 3 trial", Lancet. Nov. 24, 2012;380(9856):1829-39.
Contoli et al., "Role of deficient type III interferon-lambda production in asthma exacerbations", Nat Med. Sep. 2006;12(9):1023-6.
Dellgren et al., "Human interferon-lambda3 is a potent member of the type III interferon family", Genes Immun. Mar. 2009;10(2):125-31.
Dickensheets et al., Interferon-lambda (IFN-λ) induces signal transduction and gene expression in human hepatocytes, but not in lymphocytes or monocytes, J Leukoc Biol. Mar. 2013;93(3):377-85.
Doyle et al., "Interleukin-29 uses a type 1 interferon-like program to promote antiviral responses in human hepatocytes", Hepatology. Oct. 2006;44(4):896-906.
Edwards et al., "Interferon-lambda as a new approach for treatment of allergic asthma?", EMBO Mol Med. Jun. 2011;3(6):306-8.
Ge et al., "Genetic variation in IL28B predicts hepatitis C treatment-induced viral clearance", Nature. Sep. 17, 2009;461 (7262):399-401.
Guenterberg et al., "Interleukin-29 binds to melanoma cells inducing Jak-STAT signal transduction and apoptosis", Mol Cancer Ther. Feb. 2010;9(2):510-20.
Investigational Compound PEG-Interferon Lambda Achieved Higher Response Rates with Fewer Flu-Like and Musculoskeletal Symptoms and Cytopenias Than PEG-Interferon Alfa in Phase IIb Study of 526 Treatment-Naive Hepatitis C Patients, Press Release from Bristol-Myers Squibb, Apr. 2, 2011, retrieved from World Wide Net: http://news.bms.com/press-release/hepatitis-c/investigational-compound-peg-interferon-lambda-achieved-higher-response-ra.
Javed et al., "Therapeutic role of beta-interferons in multiple sclerosis", Pharmacol Ther. Apr. 2006;110(1):35-56.
Jewell et al., "Lambda interferon is the predominant interferon induced by influenza A virus infection in vivo", J Virol. Nov. 2010;84(21):11515-22.
Kappos et al., "Natalizumab treatment for multiple sclerosis: updated recommendations for patient selection and monitoring", Lancet Neurol. Aug. 2011;10(8):745-58.
Koltsida et al., "IL-28A (IFN-λ2) modulates lung DC function to promote Th1 immune skewing and suppress allergic airway disease", EMBO Mol Med. Jun. 2011;3(6):348-61.
Kotenko et al., "IFN-lambdas mediate antiviral protection through a distinct class II cytokine receptor complex", Nat Immunol. Jan. 2003;4(1):69-77.
Lasfar et al., "Characterization of the mouse IFN-lambda ligand-receptor system: IFN-lambdas exhibit antitumor activity against B16 melanoma", Cancer Res. Apr. 15, 2006;66(8):4468-77.
Li et al., "Interferon-lambda induces G1 phase arrest or apoptosis in oesophageal carcinoma cells and produces anti-tumour effects in combination with anti-cancer agents", Eur J Cancer Jan. 2010;46(1):180-90.
Maher et al., "IFNalpha and IFNlambda differ in their antiproliferative effects and duration of JAK/STAT signaling activity", Cancer Biol Ther. Jul. 2008;7(7):1109-15.
Marcello et al., "Interferons alpha and lambda inhibit hepatitis C virus replication with distinct signal transduction and gene regulation kinetics", Gastroenterology. Dec. 2006;131(6):1887-98.
Meager et al., "Biological activity of interleukins-28 and -29: comparison with type I interferons", Cytokine. Jul. 21, 2005;31(2):109-18.
Miller et al., "Clinical Use of Interferon-gamma", Ann N Y Acad Sci. Dec. 2009;1182:69-79.
Miller et al., "Interferon lambda as a potential new therapeutic for hepatitis C", Ann N Y Acad Sci. Dec. 2009;1182:80-7.
Muir et al., "Phase 1b study of pegylated interferon lambda 1 with or without ribavirin in patients with chronic genotype 1 hepatitis C virus infection", Hepatology. Sep. 2010;52(3):822-32.
Nakamaru et al., "Macrophage migration inhibitory factor (MIF) contributes to the development of allergic rhinitis", Cytokine. Jul. 21, 2005;31(2):103-8.
Numasaki et al., "IL-28 elicits antitumor responses against murine fibrosarcoma", J Immunol. Apr. 15, 2007;178 (8):5086-98.
Ontaneda et al., "Multiple sclerosis: new insights in pathogenesis and novel therapeutics", Annu Rev Med. 2012;63:389-404.
Pagliaccetti et al., "Interleukin-29 functions cooperatively with interferon to induce antiviral gene expression and inhibit hepatitis C virus replication", J Biol Chem. Oct. 31, 2008;283(44):30079-89.
Pardoll et al., "Immunotherapy earns its spot in the ranks of cancer therapy", J Exp Med. Feb. 13, 2012;209(2):201-9.
Pestka et al., "Interferons, interferon-like cytokines, and their receptors", Immunol Rev. Dec. 2004;202:8-32.
Pestka, S., "The interferons: 50 years after their discovery, there is much more to learn", J Biol Chem. Jul. 13, 2007;282(28):20047-51.
Pott et al., "IFN-lambda determines the intestinal epithelial antiviral host defense", Proc Natl Acad Sci U S A. May 10, 2011;108(19):7944-9.
Ramos, E., Preclinical and clinical development of pegylated interferon-lambda 1 in chronic hepatitis C, J Interferon Cytokine Res. Aug. 2010;30(8):591-5.
Robek et al., "Lambda interferon inhibits hepatitis B and C virus replication", J Virol. Mar. 2005;79(6):3851-4.
Rossi et al., "CD20-targeted tetrameric interferon-alpha, a novel and potent immunocytokine for the therapy of B-cell lymphomas", Blood. Oct. 29, 2009;114(18)3864-71.
Rossi et al., "A bispecific antibody-IFNalpha2b immunocytokine targeting CD20 and HLA-DR is highly toxic to human lymphoma and multiple myeloma cells", Cancer Res. Oct. 1, 2010;70(19):7600-9.

(56) References Cited

OTHER PUBLICATIONS

Rossi et al., "Preclinical studies on targeted delivery of multiple IFNα2b to HLA-DR in diverse hematologic cancers", Blood. Aug. 18, 2011;118(7):1877-84.
Rossi et al., "Optimization of multivalent bispecific antibodies and immunocytokines with improved in vivo properties", Bioconjug Chem. Jan. 16, 2013;24(1):63-71.
Rossi et al., "A veltuzumab-IFNα2b conjugate with potent in vitro and in vivo anti-lymphoma activity", Proceedings of the American Association for Cancer Research, Apr. 2009;50:783-784, Abstract # 3237.
Sanford et al., "Subcutaneous recombinant interferon-β-1a (Rebif®): a review of its use in the treatment of relapsing multiple sclerosis", Drugs. Oct. 1, 2011;71(14):1865-91.
Sato et al., "Antitumor activity of IFN-lambda in murine tumor models", J Immunol. Jun. 15, 2006;176(12):7686-94.
Sheppard et al., "IL-28, IL-29 and their class II cytokine receptor IL-28R", Nat Immunol. Jan. 2003;4(1):63-8.
Vilcek, J., "Fifty years of interferon research: aiming at a moving target", Immunity. Sep. 2006;25(3):343-8.
Witte et al., "Despite IFN-lambda receptor expression, blood immune cells, but not keratinocytes or melanocytes, have an impaired response to type III interferons: implications for therapeutic applications of these cytokines", Genes Immun. Dec. 2009;10(8):702-14.
Witte et al., "IL-28A, IL-28B, and IL-29: promising cytokines with type I interferon-like properties", Cytokine Growth Factor Rev. Aug. 2010;21(4):237-51.
Wolk et al., "Is there an interaction between interleukin-10 and interleukin-22?", Genes Immun. Feb. 2005;6(1):8-18.
Zeuzem et al., "Pegylated interferon-lambda (pegifn-I) shows superior viral response with improved safety and olerability versus pegifna-2a in hcv patients (g1/2/3/4): emerge phase iib through week 12", J Hepatology 2011,54: S538-39, Abstr # 1360.
Zhou et al., "Type III interferon (IFN) induces a type I IFN-like response in a restricted subset of cells through signaling pathways involving both the Jak-STAT pathway and the mitogen-activated protein kinases", J Virol. Jul. 2007;81(14):7749-58.
Zitzmann et al., "Novel interferon-lambdas induce antiproliferative effects in neuroendocrine tumor cells", Biochem Biophys Res Commun. Jun. 16, 2006;344(4):1334-41.
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract" FEBS Letters 2005; 579:3264-3270.
Banky et al., "Dimerization/Docking Domain of the Type Iα Regulatory Subunit of cAMP-dependent Protein Kinase" J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation" Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif" J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function" Trends Cell Biol. 6:216-21 (1999).
Corbin et al., "Regulation of Adenosine 3',5'-Monophosphate-dependent Protein Kinase" J. Biol. Chem. 248:1813-21 (1973).
Dhalluin et al., "Structural and Biophysical Characterization of the 40 kDa PEG-Interferon-α2a and its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor" Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Foser et al., "Improved biological and transcriptional activity of monopegylated interferon-α-2a isomers" The Pharmacogenomics J 3:312-319 (2003).
Gillies et al., "High-level expression of chimeric antibodies using adapted cDNA variable region cassettes" J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting" J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site" Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).

(56) References Cited

OTHER PUBLICATIONS

Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).

Gutterman et al., "Cytokine therapeutics: Lessons from interferon α" Proc. Natl. Acad. Sci. USA 91:1198-205 (1994).

Harris et al., "Effect of pegylation on pharmaceuticals" Nat. Rev. Drug. Discov. 2:214-221 (2003).

Hausken et al. "Mutational Analysis of the A-Kinase Anchoring Protein (AKAP)-binding Site on RII" J. Biol. Chem. 271:29016-22 (1996).

Hodneland et al., Selective immobilization of proteins to self-assembled monolayers presenting active site-directed capture ligands, Proc. Natl. Acad. Sci. USA 2002; 99:5048-5052.

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7δ-protein kinase A interaction yields novel protein kinase A-anchoring disruptor peptides" Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF" Pharm. Res. 1996;13 (7):996-1002.

Kramer et al., "Cell and virus sensitivity studies with recombinant human alpha interferons" J. Interferon. Res. 3 (4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

Lohmann et al., "High-affinity binding of the regulatory subunit (RII) of cAMP-dependent protein kinase to microtubule-associated and other cellular proteins" Proc. Natl. Acad. Sci. USA 81:6723-27 (1984).

Luft et al., "Type I IFNs Enhance the Terminal Differentiation of Dendritic Cells" J. Immunol. 161:1947-1953 (1998).

Mason, Anthony J., "Functional Analysis of the Cysteine Residues of Activin A" Mol. Endocrinol. 8:325-32 (1994).

Cardillo et al., "Targeting both IGF-1R and mTOR synergistically inhibits growth of renal cell carcinoma in vitro", BMC Cancer. Apr. 1, 2013;13:170.

Chang et al., "A novel class of anti-HIV agents with multiple copies of enfuvirtide enhances inhibition of viral replication and cellular transmission in vitro", PLoS One. 2012;7(7):e41235.

Chang et al., "Evaluation of a novel hexavalent humanized anti-IGF-1R antibody and its bivalent parental IgG in diverse cancer cell lines", PLoS One. 2012;7(8):e44235.

Goldenberg et al., "Cancer Imaging and Therapy with Bispecific Antibody Pretargeting", Update Cancer Ther. Mar. 2007;2(1):19-31.

Govindan et al., "Designing immunoconjugates for cancer therapy", Expert Opin Biol Ther. Jul. 2012;12(7):873-90.

Liu et al., "Trop-2-targeting tetrakis-ranpirnase has potent antitumor activity against triple-negative breast cancer", Mol Cancer. Mar. 10, 2014;13:53.

Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.

Rossi et al., "The dock-and-lock method combines recombinant engineering with site-specific covalent conjugation to generate multifunctional structures", Bioconjug Chem. Mar. 21, 2012;23(3):309-23.

Rossi et al., "Complex and defined biostructures with the dock-and-lock method", Trends Pharmacol Sci. Sep. 2012;33(9):474-81.

Rossi et al., "A new class of bispecific antibodies to redirect T cells for cancer immunotherapy", MAbs. Mar.-Apr. 2014;6(2):381-91.

Sharkey et al., "Improved cancer therapy and molecular imaging with multivalent, multispecific antibodies", Cancer Biother Radiopharm. Feb. 2010;25(1):1-12.

* cited by examiner

*FIG. 9*

| Cancer | Cell line | Background GAH-FITC | CD20 +hA20 | Trop-2 +hRS7 | CEACAM6 +hMN15 | HLA-DR +hL243 | EGFR +h225 |
|---|---|---|---|---|---|---|---|
| Cervical | ME-180 | 2.9 | 2.77 | 979 | 46.7 | 2.99 | 317 |
| Esophageal | TE-11 | 4.22 | 4.29 | 433 | 27.3 | 4.16 | 524 |
| Liver | HepG2 | 3.12 | 3.55 | 3.1 | 119 | 3.14 | 15 |
| | Huh-7 | 9.45 | 9.11 | 9.82 | 95.4 | 9.24 | 155 |
| Lung | A549 | 3.87 | 3.94 | 3.92 | 162 | 4.03 | 61.4 |
| | SK-MES-1 | 5.96 | 5.26 | 48.3 | 6.32 | 6.52 | 190 |
| Melanoma | A375 | 2.75 | 2.72 | 2.88 | 7.01 | 306 | 5.22 |

*FIG. 13*
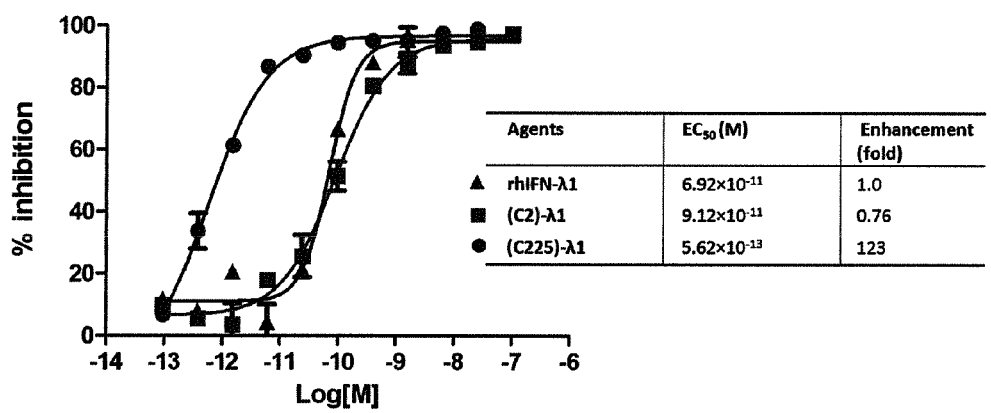
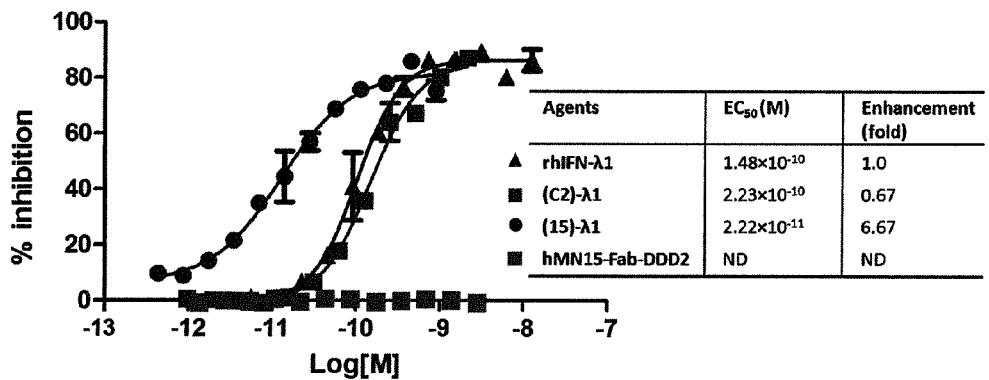

INTERFERON LAMBADA-ANTIBODY COMPLEXES

RELATED APPLICATIONS

The present application claims the benefit under 35 U.S.C. 119(e) of provisional U.S. patent application 61/591,087, filed Jan. 26, 2012. This application is a continuation-in-part of U.S. patent application Ser. No. 13/412,816, filed Mar. 6, 2012; which was a divisional of U.S. patent application Ser. No. 13/178,092 (now U.S. Pat. No. 8,158,129), filed Jul. 7, 2011; which was a continuation-in-part of U.S. patent application Ser. No. 12/731,781 (now U.S. Pat. No. 8,003,111), filed Mar. 25, 2010, which claimed the benefit under 35 U.S.C. 119(e) of provisional U.S. patent application 61/163,666, filed Mar. 26, 2009. The text of each priority application cited above is incorporated herein by reference in its entirety.

SEQUENCE LISTING

The instant application contains a Sequence Listing which has been submitted via EFS-Web and is hereby incorporated by reference in its entirety. Said ASCII copy, created on Jan. 22, 2013, is named IBC136US.txt and is 50,910 bytes in size

BACKGROUND

1. Field of the Invention

The present invention relates to compositions and methods of therapeutic use of DOCK-AND-LOCK™ (DNL™) complexes comprising interferon-lambda (IFN-λ), more preferably IFN-λ1, attached to an antibody or antigen-binding antibody fragment. In preferred embodiments the antibody may be an anti-TROP-2, anti-CEACAM5, anti-CEACAM6, anti-HLA-DR, anti-mucin, anti-CD19, anti-CD20, anti-CD74, anti-AFP, or anti-CD22 antibody. However, the skilled artisan will realize that the invention is not so limited and more broadly covers antibody-interferon complexes. Preferably, the DNL™ complexes are made using compositions and techniques as exemplified in U.S. Pat. Nos. 7,521,056; 7,527,787; 7,534,866; 7,550,143 and 7,666,400, the Examples section of each of which is incorporated herein by reference. The antibody-conjugated interferons retain in vitro activity and show substantially enhanced in vivo efficacy and increased serum half-life. Additional advantages of the DNL™ products may also include lower immunogenicity, decreased dosing frequency, increased solubility, enhanced stability, and reduced renal clearance.

2. Related Art

Interferon-α (IFNα) has been reported to have anti-tumor activity in both animal models of cancer (Ferrantini et al., 1994, J Immunol 153:4604-15) and human cancer patients (Gutterman et al., 1980, Ann Intern Med 93:399-406). IFNα can exert a variety of direct anti-tumor effects, including down-regulation of oncogenes, up-regulation of tumor suppressors, enhancement of immune recognition via increased expression of tumor surface MHC class I proteins, potentiation of apoptosis, and sensitization to chemotherapeutic agents (Gutterman et al., 1994, PNAS USA 91:1198-205; Matarrese et al., 2002, Am J Pathol 160:1507-20; Mecchia et al., 2000, Gene Ther 7:167-79; Sabaawy et al., 1999, Int J Oncol 14:1143-51; Takaoka et al, 2003, Nature 424:516-23). For some tumors, IFNα can have a direct and potent antiproliferative effect through activation of STAT1 (Grimley et al., 1998 Blood 91:3017-27).

Indirectly, IFNα can inhibit angiogenesis (Sidky and Borden, 1987, Cancer Res 47:5155-61) and stimulate host immune cells, which may be vital to the overall antitumor response but has been largely under-appreciated (Belardelli et al., 1996, Immunol Today 17:369-72). IFNα has a pleiotropic influence on immune responses through effects on myeloid cells (Raefsky et al, 1985, J Immunol 135:2507-12; Luft et al, 1998, J Immunol 161:1947-53), T-cells (Carrero et al, 2006, J Exp Med 203:933-40; Pilling et al., 1999, Eur J Immunol 29:1041-50), and B-cells (Le et al, 2001, Immunity 14:461-70). As an important modulator of the innate immune system, IFNα induces the rapid differentiation and activation of dendritic cells (Belardelli et al, 2004, Cancer Res 64:6827-30; Paquette et al., 1998, J Leukoc Biol 64:358-67; Santini et al., 2000, J Exp med 191:1777-88) and enhances the cytotoxicity, migration, cytokine production and antibody-dependent cellular cytotoxicity (ADCC) of NK cells (Biron et al., 1999, Annu Rev Immunol 17:189-220; Brunda et al. 1984, Cancer Res 44:597-601).

The therapeutic effectiveness of IFNs has been validated to date by the approval of IFN-α2 for treating hairy cell leukemia, chronic myelogenous leukemia, malignant melanoma, follicular lymphoma, condylomata acuminata, AIDs-related Kaposi sarcoma, and chronic hepatitis B and C; IFN-β for treating multiple sclerosis; and IFN-γ for treating chronic granulomatous disease and malignant osteopetrosis. Despite a vast literature on this group of autocrine and paracrine cytokines, their functions in health and disease are still being elucidated, including more effective and novel forms being introduced clinically (Pestka, 2007, J. Biol. Chem. 282:20047-51; Vilcek, 2006, Immunity 25:343-48).

Interferons are critical role players in the antitumor and antimicrobial host defense, and have been extensively explored as therapeutic agents for cancer and infectious disease (Billiau et al., 2006, Cytokine Growth Factor Rev 17:381-409; Pestka et al., 2004, Immunol Rev 202:8-32). Despite considerable efforts with type I and II interferons (IFN-α/(β and γ), their use in clinic settings have been limited because of the short circulation half-life, systemic toxicity, and suboptimal responses in patients (Pestka et al., 2004, Immunol Rev 202:8-32; Miller et al., 2009, Ann NY Acad Sci 1182:69-79). The discovery of the IFN-λ family in early 2003 brought an exciting new opportunity to develop alternative IFN agents for these unmet clinical indications (Kotenko et al., 2003, Nat Immunol 4:69-77; Sheppard et al., 2003, Nat Immunol 4:63-8).

IFN-λs, designated as type III interferons, are a newly described group of cytokines that consist of IFN-λ1, 2, 3 (also referred to as interleukin-29, 28A, and 28B, respectively), that are genetically encoded by three different genes located on chromosome 19 (Kotenko et al., 2003, Nat Immunol 4:69-77; Sheppard et al., 2003, Nat Immunol 4:63-8). At the protein level, IFN-λ2 and λ3 are is highly homologous, with 96% amino acid identity, while IFN-λ shares approximately 81% homology with IFN-λ2 and -λ3 (Sheppard et al., 2003, Nat Immunol 4:63-8). IFN-λs activate signal transduction via the JAK/STAT pathway similar to that induced by type I IFN, including the activation of JAK1 and TYK2 kinases, the phosphorylation of STAT proteins, and the activation of the transcription complex of IFN-stimulated gene factor 3 (ISGF3) (Witte et al., 2010, Cytokine Growth Factor Rev 21:237-51; Zhou et al., 2007, J Virol 81:7749-58).

A major difference between type III and type I IFN systems is the distribution of their respective receptor complexes. IFN-α/β signals through two extensively expressed type I interferon receptors, and the resulting systemic toxicity associated with IFN-α/β administration has limited their use as therapeutic agents (Pestka et al., 2007, J Biol Chem 282: 20047-51). In contrast, IFN-λs signal through a heterodimeric receptor complex consisting of unique IFN-λ receptor 1 (IFN-λR1) and IL-10 receptor 2 (IL-10R2). As previously reported (Witte et al., 2009, Genes Immun 10:702-14), IFN-λR1 has a very restricted expression pattern with the highest levels in epithelial cells, melanocytes, and hepatocytes, and the lowest level in primary central nervous system (CNS) cells. Blood immune system cells express high levels of a short IFN-λ, receptor splice variant (sIFN-λR1) that inhibits IFN-λ action. The limited responsiveness of neuronal cells and immune cells implies that the severe toxicity frequently associated with IFN-α therapy may be absent or significantly reduced with IFN-λs (Witte et al., 2009, Genes Immun 10:702-14; Witte et al., 2010, Cytokine Growth Factor Rev 21:237-51). A recent publication reported that while IFN-α and IFN-λ induce expression of a common set of ISGs (interferon-stimulated genes) in hepatocytes, unlike IFN-α, administration of IFN-λ did not induce STAT activation or ISG expression in purified lymphocytes or monocytes (Dickensheets et al., 2013, J Leukoc Biol. 93, published online Dec. 20, 2012). It was suggested that IFN-λ, may be superior to IFN-α for treatment of chronic HCV infection, as it is less likely to induce leukopenias that are often associated with IFN-α therapy (Dickensheets et al., 2013).

IFN-λs display structural features similar to IL-10-related cytokines, but functionally possess type I IFN-like anti-viral and anti-proliferative activity (Witte et al., 2009, Genes Immun 10:702-14; Ank et al., 2006, J Virol 80:4501-9; Robek et al., 2005, J Virol 79:3851-4). IFN-λ1 and λ2 have been demonstrated to reduce viral replication or the cytopathic effect of various viruses, including DNA viruses (hepatitis B virus (Robek et al., 2005, J Virol 79:3851-4, Doyle et al., 2006, 44:896-906) and herpes simplex virus 2 (Ank et al., 2008, J Immunol 180:2474-85)), ss (+) RNA viruses (EMCV; Sheppard et al., 2003, Nat Immunol 4:63-8) and hepatitis C virus (Robek et al., 2005, J Virol 79:3851-4, Doyle et al., 2006, 44:896-906; Marcello et al., 2006, Gastroenterol 131: 1887-98; Pagliaccetti et al., 2008, J Biol Chem 283:30079-89), ss (−) RNA viruses (vesicular stomatitis virus; Pagliaccetti et al., 2008, J Biol Chem 283:30079-89) and influenza-A virus (Jewell et al., 2010, J Virol 84:11515-22) and double-stranded RNA viruses, such as rotavirus (Pott et al., 2011, PNAS USA 108:7944049). IFN-λ3 has been identified from genetic studies as a key cytokine in HCV infection (Ge et al., 2009, Nature 461:399-401), and has also shown potent activity against EMCV (Dellgren et al., 2009, Genes Immun 10:125-31). A deficiency of rhinovirus-induced IFN-λ production was reported to be highly correlated with the severity of rhinovirus-induced asthma exacerbation (Controli et al., 2006, Nature Med 12:1023-26) and IFN-λ therapy has been suggested as a new approach for treatment of allergic asthma (Edwards and Johnston, 2011, EMBO Mol Med 3:306-8; Koltsida et al., 2011, EMBO Mol Med 3:348-61).

The anti-proliferative activity of IFN-λs has been established in several human cancer cell lines, including neuroendocrine carcinoma BON1 (Zitzmann et al., 2006, 344:1334-41), glioblastoma LN319 (Meager et al., 2005, Cytokine 31:109-18), immortalized keratinocyte HaCaT (Maher et al., 2008, Cancer Biol Ther 7:1109-15), melanoma F01 (Guenterberg et al., 2010, Mol Cancer Ther 9:510-20), and esophageal carcinoma TE-11 (Li et al., 2010, Eur J Cancer 46:180-90). In animal models, IFN-λs induce both tumor apoptosis and destruction through innate and adaptive immune responses, suggesting that local delivery of IFN-λ might be a useful adjunctive strategy in the treatment of human malignancies (Numasaki et al., 2007, J Immunol 178:5086-98).

In clinical settings, PEGylated IFN-λ1 (PEG-IFN-λ1) has been provisionally used for patients with chronic hepatitis C virus infection. In a phase Ib study (n=56), antiviral activity was observed at all dose levels (0.5-3.0 µg/kg), and viral load reduced 2.3 to 4.0 logs when PEG-IFN-λ1 was administrated to genotype 1 HCV patients who relapsed after IFN-α therapy (Muir et al., 2010, Hepatology 52:822-32). A phase IIb study (n=526) showed that patients with HCV genotypes 1 and 4 had significantly higher response rates to treatment with PEG-IFN-λ1 compared to PEG-IFN-α. At the same time, rates of adverse events commonly associated with type I interferon treatment were lower with PEG-IFN-λ1 than with PEG-IFN-α. Neutropenia and thrombocytopenia were infrequently observed and the rates of flu-like symptoms, anemia, and musculoskeletal symptoms decreased to about ⅓ of that seen with PEG-IFN-α treatment. However, rates of serious adverse events, depression and other common adverse events (>10%) were similar between PEG-IFN-λ1 and PEG-IFN-α. Higher rates of hepatotoxicity were seen in the highest-dose PEG-IFN-λ1 compared with PEG-IFN-α ("Investigational Compound PEG-Interferon Lambda Achieved Higher Response Rates with Fewer Flu-like and Musculoskeletal Symptoms and Cytopenias Than PEG-Interferon Alfa in Phase IIb Study of 526 Treatment-Naive Hepatitis C Patients," Apr. 2, 2011, Press Release from Bristol-Myers Squibb).

There exists a need for compositions and methods comprising interferon-lambda-antibody complexes, which retain the bioactivity of the unmodified interferon, but exhibit improved in vivo efficacy, decreased toxicity and/or superior pharmacokinetic properties.

SUMMARY OF THE INVENTION

The present invention discloses methods and compositions for producing DNL™ complexes comprising an interferon, preferably interferon-λ, more preferably IFN-λ1, attached to an antibody or antigen-binding antibody fragment. The interferon moiety may be conjugated to a dimerization and docking domain (DDD) moiety from human protein kinase A (PKA) regulatory subunit RIα, RIβ, RIIα or RIIβ or alternatively to an anchor domain (AD) moiety from an A-kinase anchoring protein (AKAP). The antibody or antibody fragment moiety is conjugated to a complementary AD or DDD moiety. Because the DDD moiety spontaneously forms dimers that bind with high affinity to the AD moiety, a DNL™ complex may be assembled from effectors, such as an interferon, an antibody or an antibody fragment, each of which is attached to a DDD moiety or an AD moiety. By mixing effectors attached to a DDD moiety with an effector attached to an AD moiety, virtually any effector can be incorporated into a DNL™ complex.

The DNL™ complex preferably contains one, two, or four copies of the interferon moiety attached to the antibody or fragment. However, the skilled artisan will realize that other types of DNL™ complexes with different structures and different ratios of interferon to antibody may be constructed and used within the scope of the claimed methods and compositions, such as those disclosed in U.S. Pat. Nos. 7,521,056; 7,527,787; 7,534,866; 7,550,143 and 7,666,400. In more preferred embodiments, the DNL™ complex may be covalently stabilized by introduction of cysteine residues at appropriate locations in the DDD and AD sequences, to form disulfide bonds that stabilize the complex.

In other preferred embodiments, the DNL™ complex comprising an interferon-conjugated antibody shows a rate of clearance from serum that is at least an order of magnitude slower than the unconjugated interferon.

The skilled artisan will realize the technique is not limited to interferon-lambda, but rather may be applied to targeted delivery of a variety of therapeutic agents, including but not limited to enzymes, cytokines, chemokines, growth factors, peptides, aptamers, hemoglobin, antibodies and fragments thereof. Exemplary agents include MIF, HMGB-1 (high mobility group box protein 1), TNF-α, IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-21, IL-23, IL-24, CCL19, CCL21, IL-8, MCP-1, RANTES, MIP-1A, MIP-1B, ENA-78, MCP-1, W-10, Gro-λ, Eotaxin, interferon-α, interferon-β, interferon-γ, interferon-λ, G-CSF, GM-CSF, SCF, PDGF, MSF, Flt-3 ligand, erythropoietin, thrombopoietin, hGH, CNTF, leptin, oncostatin M, VEGF, EGF, FGF, PlGF, insulin, hGH, calcitonin, Factor VIII, IGF, somatostatin, tissue plasminogen activator, and LIF.

Antibodies that may be of use for targeted therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), MN-15 (anti-CEACAM6), Mu-9 (anti-colon-specific antigen-p), Immu-31 (an anti-alpha-fetoprotein), anti-TAG-72 (e.g., CC49), anti-Tn, J591 or HuJ591 (anti-PSMA (prostate-specific membrane antigen)), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387, 773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983, 372, deposited as ATCC PTA-4405 and PTA-4406) and D2/B (WO 2009/130575) the text of each recited patent or application is incorporated herein by reference with respect to the Figures and Examples sections.

Anti-TNF-α antibodies are known in the art and may be of use to treat immune diseases, such as asthma (see, e.g., Erin et al., 2006, Am J Respir Crit. Care Med 174:753-62). Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

The pharmaceutical composition of the present invention may be used to treat a subject having a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. The presence of CD74 in neurofibrillary tangles of Alzheimer patients' brains (Bryan et al., Mol Neurodegeneration 2008; 3:13 doi:10.1186/1750-1326-3-13) suggests that CD74 may be a target for peptide or antibody therapy, or for targeting a therapeutic, to these areas of the brain of Alzheimer patients.

Other antibodies that may be used include antibodies against infectious disease agents, such as bacteria, viruses, mycoplasms or other pathogens. Many antibodies against such infectious agents are known in the art and any such known antibody may be used in the claimed methods and compositions. For example, antibodies against the gp120 glycoprotein antigen of human immunodeficiency virus I (HIV-1) are known, and certain of such antibodies can have an immunoprotective role in humans. See, e.g., Rossi et al., Proc. Natl. Acad. Sci. USA. 86:8055-8058, 1990. Known anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agents Chemother. 2006; 50(5):1773-9, all incorporated herein by reference.

Antibodies against malaria parasites can be directed against the sporozoite, merozoite, schizont and gametocyte stages. Monoclonal antibodies have been generated against sporozoites (cirumsporozoite antigen), and have been shown to neutralize sporozoites in vitro and in rodents (N. Yoshida et al., Science 207:71-73, 1980). Several groups have developed antibodies to T. gondii, the protozoan parasite involved in toxoplasmosis (Kasper et al., J. Immunol. 129:1694-1699, 1982; Id., 30:2407-2412, 1983). Antibodies have been developed against schistosomular surface antigens and have been found to act against schistosomulae in vivo or in vitro (Simpson et al., Parasitology, 83:163-177, 1981; Smith et al., Parasitology, 84:83-91, 1982: Gryzch et al., J. Immunol., 129:2739-2743, 1982; Zodda et al., J. Immunol. 129:2326-2328, 1982; Dissous et al., J. immunol., 129:2232-2234, 1982)

*Trypanosoma cruzi* is the causative agent of Chagas' disease, and is transmitted by blood-sucking reduviid insects. An antibody has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639-640, 1982).

Anti-fungal antibodies are known in the art, such as anti-*Sclerotinia* antibody (U.S. Pat. No. 7,910,702); antiglucuronoxylomannan antibody (Zhong and Priofski, 1998, Clin Diag Lab Immunol 5:58-64); anti-*Candida* antibodies (Matthews and Burnie, 2001, 2:472-76); and anti-glycosphingolipid antibodies (Toledo et al., 2010, BMC Microbiol 10:47).

Suitable antibodies have been developed against most of the microorganism (bacteria, viruses, protozoa, fungi, other parasites) responsible for the majority of infections in humans, and many have been used previously for in vitro diagnostic purposes. Commercially available antibodies against a wide variety of pathogens are known and may be utilized. Exemplary anti-pathogen antibodies from EMD MILLIPORE® (Billerica, Mass.) include anti-*E. coli* (MAB8272), anti-*Salmonella* (MAB748-MG-K), anti-*Listeria monocytogenes* (MAB8001), anti-*Helicobacter pylori* (IHC2140-6), anti-*Staphylococcus aureus* (MAB930), anti-*Chlamydia trachomatis* (AB1120F), anti-*Mycoplasma bovis* (MAB970), anti-*Giardia muris* (MAB 10242), anti-Dengue virus (MAB 10226), anti-Flavivirus (MAB 10216), anti-*L. pneumophila* (MAB 10223), anti-Hepatitis B (MAB10201), anti-Dengue virus (MAB10217), anti-Herpes simplex (MAB8685), anti-Epstein Barr virus (MAB 10219), anti-Coxsackievirus (MAB 10220), anti-Respiratory Syncytial virus (MAB8262-KC), anti-Adenovirus (MAB8043-KC), anti-Influenza virus (MAB8661-KC), anti-RSV (MAB8594), anti-Papillomavirus (MAB837), anti-Hepatitis C virus (AB307), anti-Enterovirus 71 (MAB979-K), anti-Measles (MAB8905-K), anti-Cytomegalovirus (MAB8140-KC), anti-Yellow Fever virus (MAB984-K), anti-Rabies (MAB8724), anti-Herpes virus 6 (MAB8535), anti-Poliovirus (MAB8566), anti-SARS (MAB8785), anti-Newcastle Disease virus (MAB80144) and anti-West Nile virus (MAB8150). Exemplary anti-pathogen antibodies from SANTA CRUZ BIOTECHNOLOGY® (Santa Cruz, Calif.) include anti-Dengue virus (sc-325018), anti-Vaccinia virus (sc-69949), anti-Polyoma virus (sc065925), anti-Rubella virus (sc101364), anti-Ebola virus (sc-51872), anti-EBV (sc-17500), anti-Measles (sc-58167), anti-Mumps (sc-57918), anti-Hantavirus (sc-57755) and anti-*Mycoplasma hominis* (sc-58171). Exemplary anti-pathogen antibodies from PROSCI® Inc. (Poway, Calif.) include anti-*Aspergillus* (35-595), anti-*Candida albicans* (35-121) and anti-*Saccharomyces cerevisiae* (35-361). Exemplary anti-pathogen antibodies from KPL (Gaithersburg, Md.) include anti-*Staphylococcus aureus* (01-90-05), anti-*Borrelia burgdorferi* (01-97-91), anti-*Helicobacter pylori* (01-93-94), anti-*Legionella* spp. (01-90-03) and anti-*Yersinia* spp. (01-90-04). There are many other sources of commercial anti-pathogen antibodies that are well known in the art. The skilled artisan will realize that antibodies against virtually any pathogen of interest are commercially and/or publicly available and any such known antibody may be incorporated into a DNL™ complex using the methods and compositions described below.

The DNL™ complexes are suitable for use in a wide variety of therapeutic and diagnostic applications. Methods of use of DNL™ complexes may include detection, diagnosis and/or treatment of a disease or other medical condition. Such conditions may include, but are not limited to, cancer, hyperplasia, asthma, multiple sclerosis, infectious diseases, chronic viral hepatitis, herpes virus infection, chronic infection with hepatitus B or C virus, chronic granulomatous disease, malignant osteopetrosis, Karposi's sarcoma, human papilloma virus infection, influenza, chronic myelogenous leukemia, hairy cell leukemia, cutaneous T-cell lymphoma, follicular lymphoma, metastatic renal cell carcinoma, haemangioma, hematologic malignancies, condylomata acuminata and malignant melanoma.

Exemplary types of tumors that may be treated include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

Various viral infections may be treated, including but not limited to human immunodeficiency virus (HIV), herpes virus, herpes simplex virus, vaccinia virus, cytomegalovirus, rabies virus, influenza virus, rhinovirus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus; or the bacterium is selected from the group consisting of *Streptococcus agalactiae, Legionella pneumophila, Streptococcus pyogenes, Escherichia coli, Neisseria gonorrhoeae, Neisseria meningitidis, Pneumococcus, Hemophilus influenzae* B, *Treponema pallidum*, Lyme disease spirochetes, *Pseudomonas aeruginosa, Mycobacterium leprae, Brucella abortus, Mycobacterium tuberculosis* or *Clostridium tetani*.

BRIEF DESCRIPTION OF THE DRAWINGS

FIG. 2(A) cell-based reporter gene assay.

FIG. 2(B) viral protection assay with EMC virus and A549 cells.

FIG. 2(C) In vitro lymphoma proliferation assays using Daudi cells.

FIG. 2(D) In vitro lymphoma proliferation assays using Jeko-1 cells.

FIG. 9 Cell surface expression of antigens in various cell lines.

FIG. 13. Anti-viral effects. (A) Enhanced anti-HCV potency of (c225)-λ1 in Huh-7 cells. A Huh-7 stable cell line with HCV genotype 1b Con1 replicon expressing firefly luciferase was treated with indicated concentrations of (c225)-λ1, (C2)-λ1, or rhIFN-λ1 agents. After 3 days, luciferase activity was measured and antiviral effects were determined by percent activity reduction relative to untreated cells. Data were analyzed by Graph Pad Prism using a sigmoidal fit (variable slope). Samples were run twice independently in duplicate. (B) Enhanced anti-EMCV potency of (15)-λ1 in A549 cells. A549 cells were incubated with serial dilutions of (15)-1, (C2)-λ1, rhIFN-λ1, or hMN15-Fab-DDD2 before being challenged with EMCV. A visual cytopathic effect (CPE) determination was performed, and the data were analyzed by GraphPad Prism using a sigmoidal fit (variable slope). Samples were run twice independently in duplicate.

DETAILED DESCRIPTION

Definitions

Figure 1:
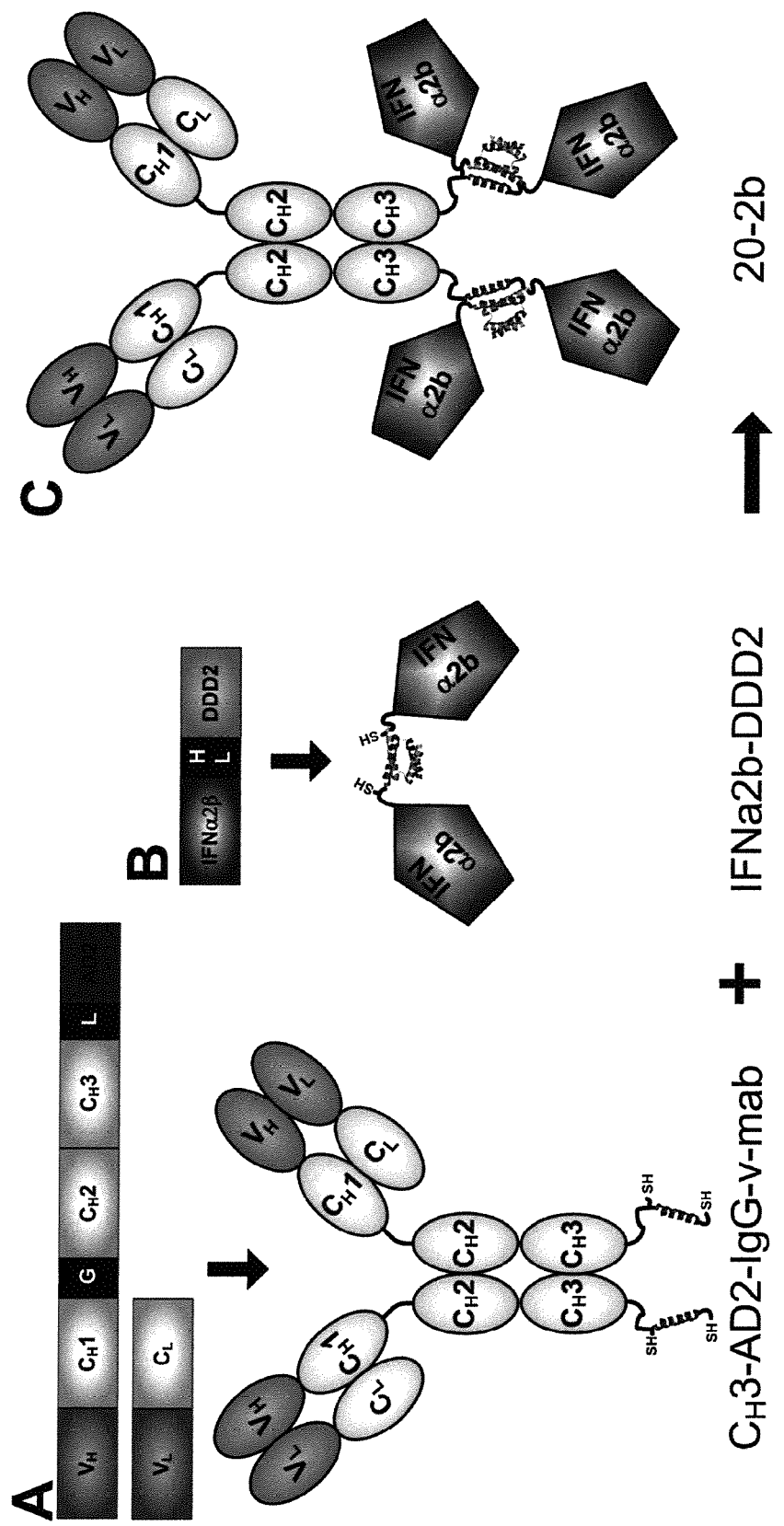
FIG. 1 is a cartoon drawing depicting the gene structures (A and B) for expression of Cytokine-DDD2 (C), and IgG-AD2 (D) DNL™ modules. The modules are combined to form DNL™ structures consisting of four cytokines fused to an IgG (E).

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as F(ab')$_2$, F(ab)$_2$, Fab', Fab, Fv, sFv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb).

An antibody or immunoconjugate preparation, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of a disease state. A physiologically significant effect could also be the evocation of a humoral and/or cellular immune response in the recipient subject leading to growth inhibition or death of target cells.

DOCK-AND-LOCK™ (DNL™)

In preferred embodiments, an interferon-antibody complex is formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell. Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα (Newlon et al., Nat. Struct. Biol. 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL™ constructs, different AD or DDD sequences may be utilized. Exemplary DDD and AD sequences are provided below.

```
DDD1
                                        (SEQ ID NO: 1)
SHIQIPPGLTELLQGYTVEVLRQQPPDLVEFAVEYFTRLREARA

DDD2
                                        (SEQ ID NO: 2)
CGHIQIPPGLTELLQGYTVEVLRQQPPDLVEFAVEYFTRLREARA

AD1
                                        (SEQ ID NO: 3)
QIEYLAKQIVDNAIQQA

AD2
                                        (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                        (SEQ ID NO: 5)
SLRECELYVQKHNIQALLKDSIVQLCTARPERPMAFLR
EYFERLEKEEAK

DDD3C
                                        (SEQ ID NO: 6)
MSCGGSLRECELYVQKHNIQALLKDSIVQLCTARPERPMA
FLREYFERLEKEEAK

AD3
                                        (SEQ ID NO: 7)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                        (SEQ ID NO: 8)
SLRECELYVQKHNIQALLKDVSIVQLCTARPERPMAFLREYFE
KLEKEEAK

PKA RIβ
                                        (SEQ ID NO: 9)
SLKGCELYVQLHGIQQVLKDCIVHLCISKPERPMKFLREHFEK
LEKEENRQILA

PKA RIIα
                                        (SEQ ID NO: 10)
SHIQIPPGLTELLQGYTVEVGQQPPDLVDFAVEYFTRLREARRQ

PKA RIIβ
                                        (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. SH<u>I</u>QIPPG<u>L</u>TE<u>LL</u>QGY<u>T</u> <u>V</u>E<u>V</u>LRQQPPD<u>L</u>VE<u>F</u>A<u>V</u>E<u>Y</u>F<u>T</u>R<u>L</u>REARA (SEQ ID NO:1)

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 1. In devising Table 1, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 1

Conservative Amino Acid Substitutions in DDD1 (SEQ ID NO: 1).
Consensus sequence disclosed as SEQ ID NO: 87.

```
S H I Q I P P G L T E L L Q G Y T V E V L R
T K N     A   S D     N A   S   D     K
  R

Q Q P P D L V E F A V E Y F T R L R E A R A
N N     E   D L   D     S K   K D L K   L
              I             I   I
              V             V   V
```

THIQIPPGLTELLQGYTVEVLRQQPPDLVEFAVEYFTRLREARA (SEQ ID NO: 12)

SKIQIPPGLTELLQGYTVEVLRQQPPDLVEFAVEYFTRLREARA (SEQ ID NO: 13)

SRIQIPPGLTELLQGYTVEVLRQQPPDLVEFAVEYFTRLREARA (SEQ ID NO: 14)

SHINIPPGLTELLQGYTVEVLRQQPPDLVEFAVEYFTRLREARA (SEQ ID NO: 15)

SHIQIPPALTELLQGYTVEVLRQQPPDLVEFAVEYFTRLREARA (SEQ ID NO: 16)

SHIQIPPGLSELLQGYTVEVLRQQPPDLVEFAVEYFTRLREARA (SEQ ID NO: 17)

SHIQIPPGLTDLLQGYTVEVLRQQPPDLVEFAVEYFTRLREARA (SEQ ID NO: 18)

SHIQIPPGLTELLNGYTVEVLRQQPPDLVEFAVEYFIRLREARA (SEQ ID NO: 19)

SHIQIPPGLTELLQAYTVEVLRQQPPDLVEFAVEYFTRLREARA (SEQ ID NO: 20)

SHIQIPPGLTELLQGYSVEVLRQQPPDLVEFAVEYFTRLREARA (SEQ ID NO: 21)

SHIQIPPGLTELLQGYTVDVLRQQPPDLVEFAVEYFTRLREARA (SEQ ID NO: 22)

SHIQIPPGLTELLQGYTVEVLKQQPPDLVEFAVEYFTRLREARA (SEQ ID NO: 23)

SHIQIPPGLTELLQGYTVEVLRNQPPDLVEFAVEYFTRLREARA (SEQ ID NO: 24)

SHIQIPPGLTELLQGYTVEVLRQNPPDLVEFAVEYFTRLREARA (SEQ ID NO: 25)

SHIQIPPGLTELLQGYTVEVLRQQPPELVEFAVEYFTRLREARA (SEQ ID NO: 26)

SHIQIPPGLTELLQGYTVEVLRQQPPDLVDFAVEYFIRLREARA (SEQ ID NO: 27)

SHIQIPPGLTELLQGYTVEVLRQQPPDLVEFLVEYFTRLREARA (SEQ ID NO: 28)

SHIQIPPGLTELLQGYTVEVLRQQPPDLVEFIVEYFTRLREARA (SEQ ID NO: 29)

SHIQIPPGLTELLQGYTVEVLRQQPPDLVEFVVEYFTRLREARA (SEQ ID NO: 30)

SHIQIPPGLTELLQGYTVEVLRQQPPDLVEFAVDYFTRLREARA (SEQ ID NO: 31)

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 2 shows potential conservative amino acid substitutions in the sequence of AKAP-IS (AD1, SEQ ID NO:3), similar to that shown for DDD1 (SEQ ID NO:1) in Table 1 above.

A limited number of such potential alternative AD moiety sequences are shown in SEQ ID NO:32 to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

AKAP-IS

QIEYLAKQIVDNAIQQA (SEQ ID NO: 3)

TABLE 2

Conservative Amino Acid Substitutions in AD1 (SEQ ID NO: 3).
Consensus sequence disclosed as SEQ ID NO: 88.

| Q | I | E | Y | L | A | K | Q | I | V | D | N | A | I | Q | Q | A |
|---|---|---|---|---|---|---|---|---|---|---|---|---|---|---|---|---|
| N | L | D | F | I | | R | N | | | E | Q | | | N | N | L |
| | V | | T | V | | | | | | | | | | | | I |
| | | | S | | | | | | | | | | | | | V |

NIEYLAKQIVDNAIQQA (SEQ ID NO: 32)

QLEYLAKQIVDNAIQQA (SEQ ID NO: 33)

QVEYLAKQIVDNAIQQA (SEQ ID NO: 34)

QIDYLAKQIVDNAIQQA (SEQ ID NO: 35)

QIEFLAKQIVDNAIQQA (SEQ ID NO: 36)

QIETLAKQIVDNAIQQA (SEQ ID NO: 37)

QIESLAKQIVDNAIQQA (SEQ ID NO: 38)

QIEYIAKQIVDNAIQQA (SEQ ID NO: 39)

QIEYVAKQIVDNAIQQA (SEQ ID NO: 40)

QTRYLARQIVDNAIQQA (SEQ ID NO: 41)

QIEYLAKNIVDNAIQQA (SEQ ID NO: 42)

QIEYLAKQIVENAIQQA (SEQ ID NO: 43)

QIEYLAKQIVDQAIQQA (SEQ ID NO: 44)

QIEYLAKQIVDNAINQA (SEQ ID NO: 45)

QIEYLAKQIVDNAIQNA (SEQ ID NO: 46)

QIEYLAKQIVDNAIQQL (SEQ ID NO: 47)

QIEYLAKQIVDNAIQQI (SEQ ID NO: 48)

QIEYLAKQIVDNAIQQV (SEQ ID NO: 49)

Gold et al. (2006, Mol Cell 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

SuperAKAP-IS
(SEQ ID NO: 50)
QIEYVAKQIVDYAIHQA

-continued

Alternative AKAP sequences
(SEQ ID NO: 51)
QIEYKAKQIVDHAIHQA (SEQ ID NO: 52)
QIEYHAKQIVDHAIHQA (SEQ ID NO: 53)
QIEYVAKQIVDHAIHQA FIG. 2 of Gold et al. disclosed additional DDD-binding sequences from a variety of AKAP proteins, shown below.

RII-Specific AKAPs
AKAP-KL
(SEQ ID NO: 54)
PLEYQAGLLVQNAIQQAI

AKAP79
(SEQ ID NO: 55)
LLIETASSLVKNAIQLSI

AKAP-Lbc
(SEQ ID NO: 56)
LIEEAASRIVDAVIEQVK

RI-Specific AKAPs
AKAPce
ALYQFADRFSELVISEAL (SEQ ID NO: 57)

RIAD
LEQVANQLADQIIKEAT (SEQ ID NO: 58)

PV38
FEELAWKIAKMIWSDVF (SEQ ID NO: 59)

Dual-Specificity AKAPs
AKAP7
ELVRLSKRLVENAVLKAV (SEQ ID NO: 60)

MAP2D
TAEEVSARIVQVVTAEAV (SEQ ID NO: 61)

DAKAP1
QIKQAAFQLISQVILEAT (SEQ ID NO: 62)

DAKAP2
LAWKIAKMIVSDVMQQ (SEQ ID NO: 63)

Stokka et al. (2006, Biochem J 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

Ht31
DLIFEAASRIVDAVIEQVKAAGAY (SEQ ID NO: 64)

RIAD
LEQYANQLADQIIKEATE (SEQ ID NO: 65)

PV-38
FEELAWKIAKMIWSDVFQQC (SEQ ID NO: 66)

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

| AKAP Peptide sequences | |
|---|---|
| | Peptide Sequence |
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEATEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Figure 4:
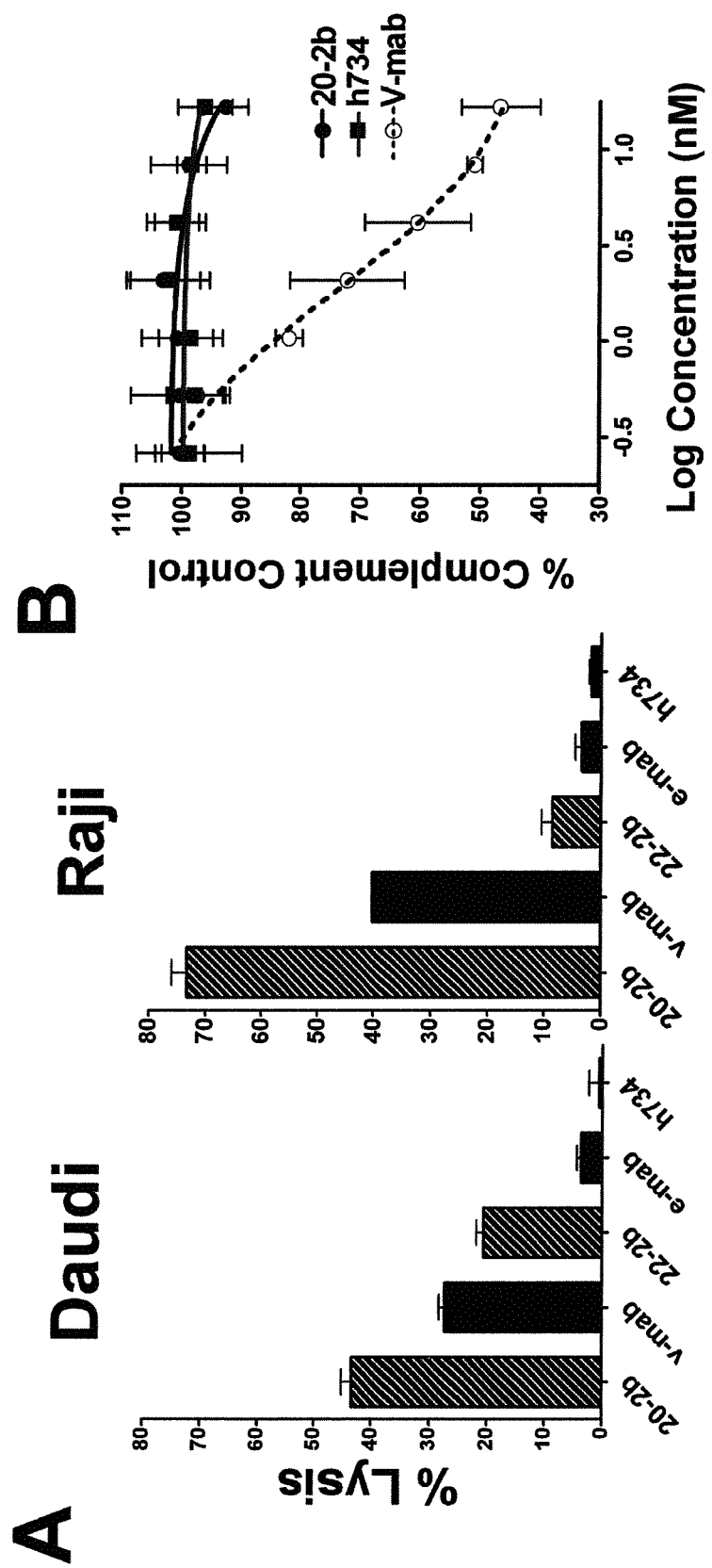
FIG. 4(A) illustrates ADCC effector functions of 20-2b. Daudi or Raji cells were incubated with 20-2b, 22-2b, v-mab, epratuzumab (e-mab), or h734 at 5 μg/ml in the presence of freshly isolated PBMCs for 4 h before quantification of cell lysis.
FIG. 4(B) shows CDC effector functions of 20-2B. Daudi cells were incubated with serial dilutions of 20-2b (●), 734-2b (■) or v-mab (○) in the presence of human complement. The % complement control (number of viable cells in the test sample compared to cells treated with complement only) was plotted vs. the log of the nM concentration. Error bars, SD.

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
                AKAP-IS
                                        (SEQ ID NO: 3)
            QIEYLAKQIVDNAIQQA
```

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                                      (SEQ ID NO: 1)
        SHIQIPPGLTELLQGYTVEVLRQQPPDLVEFAVEYFTRLREARA
```

A modified set of conservative amino acid substitutions for the DDD1 (SEQ ID NO:1) sequence, based on the data of Carr et al. (2001) is shown in Table 4. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 1 and Table 2.

Interferons and Other Immunomodulators

In certain preferred embodiments, the effector moiety is an immunomodulator. An immunomodulator is an agent that when present, alters, suppresses or stimulates the body's immune system. Immunomodulators of use may include a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferon-β, interferon-β, interferon-γ or interferon-λ, and stem cell growth factor, such as that designated "S1 factor".

In more preferred embodiments, the effector moieties are cytokines, such as lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); placenta growth factor (PlGF), hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -γ and -λ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor (TNF, such as TNF-α) and LT. In a particularly preferred embodiment, the cytokine is IFN-α2b.

The amino acid sequences of protein or peptide immunomodulators, such as cytokines, are well known in the art and any such known sequences may be used in the practice of the

TABLE 4

Conservative Amino Acid Substitutions in DDD1 (SEQ ID NO: 1).
Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   |   | S |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   |   |   |   | I | D |   |   |   | S | K |   | K |   | L |   | L |
|   |   |   |   |   |   |   |   |   | L |   |   |   |   |   |   |   |   |   | I |   | I |
|   |   |   |   |   |   |   |   |   | A |   |   |   |   |   |   |   |   |   | V |   | V |

The skilled artisan will realize that these and other amino acid substitutions in the DDD or AD amino acid sequences may be utilized to produce alternative species within the genus of AD or DDD moieties, using techniques that are standard in the field and only routine experimentation.

instant invention. The skilled artisan is aware of numerous sources of public information on cytokine sequence. For example, the NCBI database contains both protein and encoding nucleic acid sequences for a large number of cytokines and immunomodulators, such as erythropoietin (GEN- BANK® NM 000799), IL-1 beta (GenPept AAH08678), GM-CSF (GenPept AAA52578), TNF-α (GenPept CAA26669), interferon-alpha (GenPept AAA52716.1), interferon-alpha 2b (GenPept AAP20099.1), interferon-lambda (GenPept 30G6_B; 3HHC_A; 3HHC_B; 3HHC_C; 3HHC_D; EAW56870.1; EAW56869.1; AAI40873.1) and virtually any of the peptide or protein immunomodulators listed above. It is a matter of routine for the skilled artisan to identify an appropriate amino acid and/or nucleic acid sequence for essentially any protein or peptide effector moiety of interest. Commercial sources of cytokines are also available and may be used, such as the full-length human IFN-α2b cDNA clone (INVITROGEN™ ULTIMATE™ ORF human clone cat# HORF01Clone ID IOH35221).

Antibodies

In certain embodiments, an antibody or antigen binding fragment thereof may be incorporated into a DNL™ construct, such as by attachment of an antibody or fragment to an interferon or other cytokine for targeted delivery of the cytokine. Any known antibody or antigen-binding fragment thereof may be incorporated into a DNL™ construct. In preferred embodiments, the complex is of use for cancer therapy and the antibody binds to a tumor associated antigen (TAA). A variety of tumor-associated antigens are known in the art, including but not limited to carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5ac, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product. Other types of target antigen are of use for antibody-based therapy of different disease states and DNL™ constructs incorporating antibodies that target any such alternative antigen may be utilized.

Exemplary anti-cancer antibodies that may be utilized in DNL™ constructs include, but are not limited to, hR1 (anti-IGF-1R, U.S. Provisional Patent Application Ser. No. 61/145,896, filed Jan. 20, 2009) hPAM4 (anti-MUC1, U.S. Pat. No. 7,282,567), hA20 (anti-CD20, U.S. Pat. No. 7,251,164), hA19 (anti-CD19, U.S. Pat. No. 7,109,304), hIMMU-31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. patent application Ser. No. 10/672,278), hRS7 (anti-EGP-1, U.S. Pat. No. 7,238,785) and hMN-3 (anti-CEA, U.S. Pat. No. 7,541,440) the Examples section of each cited patent or application incorporated herein by reference. The skilled artisan will realize that this list is not limiting and any other known anti-TAA antibody may be incorporated into the DNL™ constructs.

Antigen-binding antibody fragments are well known in the art, such as F(ab')$_2$, F(ab)$_2$, Fab', Fab, Fv, scFv and the like, and any such known fragment may be used. As used herein, an antigen-binding antibody fragment refers to any fragment of an antibody that binds with the same antigen that is recognized by the intact or parent antibody. Techniques for preparing AD and/or DDD conjugates of virtually any antibody or fragment of interest are known (e.g., U.S. Pat. No. 7,527,787).

An antibody or fragment thereof may be used which is not conjugated to a therapeutic agent is referred to as a "naked" antibody or fragment thereof. In alternative embodiments, antibodies or fragments may be conjugated to one or more therapeutic and/or diagnostic agents. A wide variety of such therapeutic and diagnostic agents are known in the art, as discussed in more detail below, and any such known therapeutic or diagnostic agent may be used.

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A SEPHAROSE®, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and IgG$_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, *Nature* 380:364-366; Pasqualini, 1999, *The Quart. J. Nucl. Med.* 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, *Science*, 246:1274-1281) to allow rapid and easy identification of monoclonal Fab' fragments with the desired specificity. F(ab)$_2$ fragments may be generated by papain digestion of an antibody and Fab fragments obtained by disulfide reduction.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs*." FASEB Vol 9:73-80 (1995) and R. E. Bird and B. W. Walker, "*Single Chain Antibody Variable Regions*," TIBTECH, Vol 9: 132-137 (1991).

Techniques for producing single domain antibodies (DABs) are also known in the art, as disclosed for example in Cossins et al. (2006, Prot Express Purif 51:253-259), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Particular antibodies that may be of use for therapy of cancer within the scope of the claimed methods and compositions include, but are not limited to, LL1 (anti-CD74), epratuzumab (LL2) and RFB4 (anti-CD22), RS7 (anti-epithelial glycoprotein-1 (EGP-1) or anti-TROP-2), PAM4 and KC4 (both anti-mucin), MN-14 (anti-carcinoembryonic antigen (CEACAM5, also known as CD66e), Mu-9 (anti-colon-specific antigen-p), Immu-31 (an anti-alpha-fetoprotein), anti-TAG-72 (e.g., CC49), anti-Tn, J591 or HuJ591 (anti-PSMA (prostate-specific membrane antigen)), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); veltuzumab (anti-CD20), and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387, 773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983, 372, deposited as ATCC PTA-4405 and PTA-4406) and D2/B (WO 2009/130575) the text of each recited patent or application is incorporated herein by reference with respect to the Figures and Examples sections.

Anti-TNF-α antibodies are known in the art and may be of use to treat immune diseases, such as asthma. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

The pharmaceutical composition of the present invention may be used to treat a subject having a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Due to the expression of CD74 in the neurofibrillary tangles of the brains of Alzheimer disease patients (Bryan et al., Mol Neurodegeneration 2008; 3:13), this is another target for treating this disease, either via an anti-CD74 antagonistic peptide or antibody, used either alone or as a conjugate via DNL constructs, as described herein.

Other antibodies that may be used include antibodies against infectious disease agents, such as bacteria, viruses, mycoplasms or other pathogens. Many antibodies against such infectious agents are known in the art and any such known antibody may be used in the claimed methods and compositions. For example, antibodies against the gp120 glycoprotein antigen of human immunodeficiency virus I (HIV-1) are known, and certain of such antibodies can have an immunoprotective role in humans. See, e.g., Rossi et al., Proc. Natl. Acad. Sci. USA. 86:8055-8058, 1990. Known anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agents Chemother. 2006; 50(5):1773-9, all incorporated herein by reference.

Antibodies against malaria parasites can be directed against the sporozoite, merozoite, schizont and gametocyte stages. Monoclonal antibodies have been generated against sporozoites (cirumsporozoite antigen), and have been shown to neutralize sporozoites in vitro and in rodents (N. Yoshida et al., Science 207:71-73, 1980). Several groups have developed antibodies to T. gondii, the protozoan parasite involved in toxoplasmosis (Kasper et al., J. Immunol. 129:1694-1699, 1982; Id., 30:2407-2412, 1983). Antibodies have been developed against schistosomular surface antigens and have been found to act against schistosomulae in vivo or in vitro (Simpson et al., Parasitology, 83:163-177, 1981; Smith et al., Parasitology, 84:83-91, 1982: Gryzch et al., J. Immunol., 129:2739-2743, 1982; Zodda et al., J. Immunol. 129:2326-2328, 1982; Dissous et al., J. immunol., 129:2232-2234, 1982)

Trypanosoma cruzi is the causative agent of Chagas' disease, and is transmitted by blood-sucking reduviid insects. An antibody has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639-640, 1982).

Anti-fungal antibodies are known in the art, such as anti-Sclerotinia antibody (U.S. Pat. No. 7,910,702); antiglucuronoxylomannan antibody (Zhong and Priofski, 1998, Clin Diag Lab Immunol 5:58-64); anti-Candida antibodies (Matthews and Burnie, 2001, 2:472-76); and anti-glycosphingolipid antibodies (Toledo et al., 2010, BMC Microbiol 10:47).

Suitable antibodies have been developed against most of the microorganism (bacteria, viruses, protozoa, fungi, other parasites) responsible for the majority of infections in humans, and many have been used previously for in vitro diagnostic purposes. These antibodies, and newer antibodies that can be generated by conventional methods, are appropriate for use in the present invention.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:85) and veltuzumab (SEQ ID NO:86).

Rituximab heavy chain variable region sequence (SEQ ID NO:85)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCPPCPAPELLGG

PSVFLFPPKPKDTLMISRTPEVTCVVVDVSHEDPEVKFNWYVDGVEVHNAKTKPREEQY

-continued

NSTYRVVSVLTVLHQDWLNGKEYKCKVSNKATPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Veltuzumab heavy chain variable region (SEQ ID NO:86

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m-1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies. Table 5 compares the allotype sequences of rituximab vs. veltuzumab. As shown in Table 5, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113: 1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 5

Allotypes of Rituximab vs. Veltuzumab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Amino Acid Substitutions

In certain embodiments, the disclosed methods and compositions may involve production and use of proteins or peptides with one or more substituted amino acid residues. In a non-limiting example, the DDD and/or AD sequences used to make the DNL™ constructs may be further optimized, for example to increase the DDD-AD binding affinity.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Be and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. No. 5,475,096 and U.S. Pat. No. 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

AFFIBODY® AND FYNOMER®

Certain alternative embodiments may utilize an AFFIBODY® in place of an antibody. The AFFIBODY® are commercially available from AFFIBODY® AB (Solna, Sweden). An AFFIBODY® is a small protein that functions as an antibody mimetic and is of use in binding target molecules. The AFFIBODY® was developed by combinatorial engineering on an alpha helical protein scaffold (Nord et al., 1995, Protein Eng 8:601-8; Nord et al., 1997, Nat Biotechnol 15:772-77). The AFFIBODY® design is based on a three helix bundle structure comprising the IgG binding domain of protein A (Nord et al., 1995; 1997). AFFIBODY® with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins. The phage display library may be screened against any known antigen, using standard phage display screening techniques (e.g., Pasqualini and Ruoslahti, 1996, Nature 380:364-366; Pasqualini, 1999, Quart. J. Nucl. Med. 43:159-162), in order to identify one or more AFFIBODY® against the target antigen.

A $^{177}$Lu-labeled AFFIBODY® specific for HER2/neu has been demonstrated to target HER2-expressing xenografts in vivo (Tolmachev et al., 2007, Cancer Res 67:2773-82). Although renal toxicity due to accumulation of the low molecular weight radiolabeled compound was initially a problem, reversible binding to albumin reduced renal accumulation, enabling radionuclide-based therapy with labeled affibody (Id.).

The feasibility of using radiolabeled AFFIBODY® for in vivo tumor imaging has been recently demonstrated (Tolmachev et al., 2011, Bioconjugate Chem 22:894-902). A maleimide-derivatized NOTA was conjugated to the anti-HER2 affibody and radiolabeled with ¹¹¹In (Id.). Administration to mice bearing the HER2-expressing DU-145 xenograft, followed by gamma camera imaging, allowed visualization of the xenograft (Id.).

FYNOMER® can also bind to target antigens with a similar affinity and specificity to antibodies. FYNOMER® are based on the human Fyn SH3 domain as a scaffold for assembly of binding molecules. The Fyn SH3 domain is a fully human, 63 amino acid protein that can be produced in bacteria with high yields. FYNOMER® may be linked together to yield a multispecific binding protein with affinities for two or more different antigen targets. FYNOMER® are commercially available from COVAGEN® AG (Zurich, Switzerland).

The skilled artisan will realize that AFFIBODY® or FYNOMER® may be used as targeting molecules in the practice of the claimed methods and compositions.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "DOCK-AND-LOCK™" (DNL™) has been utilized to produce combinations of virtually any desired antibodies, antibody fragments and other effector molecules (see, e.g., U.S. Pat. Nos. 7,550,143; 7,521,056; 7,534,866; 7,527,787 and U.S. Ser. No. 11/925,408, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074, 405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents, such as interferon-λ.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO:98), wherein DOTA is 1,4,7,10-tetraazacyclododecane-1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Therapeutic Agents

In various embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used as adjunct therapies to the interferon-antibody DNL™ constructs described herein. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum (CDDP), Cox-2 inhibitors, irinotecan (CPT-11), SN-38, carboplatin, cladribine, clofarabine, cytosine arabinoside, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, tyrosine kinase and Bruton kinase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicamycin, procarbazine, paclitaxel, pentostatin, PSI-341, raloxifene, semustine, streptozocin, tamoxifen, temazolomide (an aqueous form of DTIC), transplatinum, thalidomide, thioguanine, thiotepa, teniposide, topotecan, uracil mustard, vinorelbine, vinblastine, vincristine and vinca alkaloids.

Tyrosine kinase inhibitors of use may include LFM-A13, dasatinib, imatinib or nilotinib.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{19}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Conjugation Techniques

In certain embodiments, the DNL™ construct may be conjugated to one or more therapeutic or diagnostic agents. For example, $^{131}$I can be incorporated into a tyrosine of a protein or peptide, or a drug attached to an epsilon amino group of a lysine residue. Therapeutic and diagnostic agents also can be attached, for example to reduced SH groups. Many methods for making covalent or non-covalent conjugates of therapeutic or diagnostic agents with proteins or peptides are known in the art and any such known method may be utilized.

A therapeutic or diagnostic agent can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

In some embodiments, a chelating agent may be attached to a protein or peptide and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins or peptides are well known in the art (see, e.g., U.S. Pat. No. 7,563,433, the Examples section of which is incorporated herein by reference). Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$I, $^{67}$Ga, $^{68}$Ga, $^{99m}$Tc, $^{94m}$Tc, $^{11}$C, $^{13}$N, $^{15}$O or $^{76}$Br for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433.

Methods of Treatment

Various embodiments concern methods of treating a cancer in a subject, such as a mammal, including humans, domestic or companion pets, such as dogs and cats, comprising administering to the subject a therapeutically effective amount of a interferon-antibody DNL™ construct. The administration of interferon-antibody DNL™ construct can be supplemented by administering concurrently or sequentially a therapeutically effective amount of an antibody that binds to or is reactive with an antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5ac, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof.

The interferon-antibody DNL™ construct therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The interferon-antibody DNL™ construct can be formulated according to known methods to prepare pharmaceutically useful compositions, whereby the interferon-antibody DNL™ construct is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, EMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The interferon-antibody DNL™ construct can be formulated for intravenous administration via, for example, bolus injection or continuous infusion. Preferably, interferon-antibody DNL™ construct is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the interferon-antibody DNL™ construct. Control release preparations can be prepared through the use of polymers to complex or adsorb the interferon-antibody DNL™ construct. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the interferon-antibody DNL™ construct, the amount of interferon-antibody DNL™ construct within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The interferon-antibody DNL™ construct may also be administered to a mammal subcutaneously or even by other parenteral routes. Preferably, the construct is infused over a period of less than about 4 hours, and more preferably, over a period of less than about 3 hours.

More generally, the dosage of an administered interferon-antibody DNL™ construct for humans will vary depending upon such factors as the patient's age, weight, height, sex, general medical condition and previous medical history. In non-limiting examples, the dosage may be 10 µg, 20 µg, 50 µg, 75 µg, 100 µg, 150 µg, 200 µg, 250 µg, 300 µg, 400 µg, 500 µg, 750 µg, 1 mg, 1.5 mg, 2 mg, 2.5 mg, 5 mg, 10 mg, 20 mg, 50 mg, 75 mg or 100 mg. The skilled artisan will realize that the dosage may be decreased or treatment terminated if signs of toxicity are observed. The dosage may be repeated as needed, for example, twice per week for 4-10 weeks, once per week for 4-10 weeks, once per week for 8 weeks, or once per week for 4 weeks. It may also be given less frequently, such as every other week for several months, or monthly or quarterly for many months, as needed in a maintenance therapy. Alternatively, a interferon-antibody DNL™ construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule.

In preferred embodiments, the interferon-antibody DNL™ constructs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

In still other embodiments, the PEGylated DNL™ complexes may be of use to treat subjects infected with pathogenic organisms, such as bacteria, viruses or fungi. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albicans*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophila, Streptococcus pyogenes, Escherichia coli, Neisseria gonorrhoeae, Neisseria meningitidis, Pneumococcus* spp., *Hemophilus influenzae* B, *Treponema pallidum*, Lyme disease spirochetes, *Pseudomonas aeruginosa, Mycobacterium leprae, Brucella abortus, Mycobacterium tuberculosis* or a *Mycoplasma*.

Kits

Various embodiments may concern kits containing components suitable for treating diseased tissue in a patient. Exemplary kits may contain at least one or more interferon-antibody constructs as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are provided to illustrate, but not to limit, the claims of the present invention.

Example 1

$C_{H3}$-AD2-IgG Expression Vectors

The pdHL2 mammalian expression vector has been used for the expression of recombinant IgGs (Qu et al., Methods 2005, 36:84-95). A plasmid shuttle vector was produced to facilitate the conversion of any IgG-pdHL2 vector into a $C_{H3}$-AD2-IgG-pdHL2 vector. The gene for the Fc ($C_{H2}$ and $C_{H3}$ domains) was amplified by PCR using the pdHL2 vector as a template and the following oligonucleotide primers:

```
Fc BglII Left
                                    (SEQ ID NO: 90)
AGATCTGGCGCACCTGAACTCCTG Fc Bam- EcoRI Right
                                    (SEQ ID NO: 91)
GAATTCGGATCCTTTACCCGGAGACAGGGAGAG.
```

The amplimer was cloned in the pGemT PCR cloning vector (Promega). The Fc insert fragment was excised from pGemT with Xba I and Bam HI and ligated with AD2-pdHL2 vector that was prepared by digesting h679-Fab-AD2-pdHL2 (Rossi et al., Proc Natl Acad Sci USA 2006, 103:6841-6) with Xba I and Bam HI, to generate the shuttle vector Fc-AD2-pdHL2. To convert IgG-pdHL2 expression vectors to a $C_{H3}$-AD2-IgG-pdHL2 expression vectors, an 861 bp BsrG I/Nde I restriction fragment was excised from the former and replaced with a 952 bp BsrG I/Nde I restriction fragment excised from the Fc-AD2-pdHL2 vector. The following is a partial list of $C_{H3}$-AD2-IgG-pdHL2 expression vectors that have been generated and used for the production of recombinant humanized IgG-AD2 modules:

$C_{H3}$-AD2-IgG-hA20 (anti-CD20)
$C_{H3}$-AD2-IgG-hLL2 (anti-CD22)
$C_{H3}$-AD2-IgG-hL243 (anti-HLA-DR)
$C_{H3}$-AD2-IgG-hLL1 (anti-CD74)
$C_{H3}$-AD2-IgG-hR1 (anti-IGF-1R)
$C_{H3}$-AD2-IgG-h734 (anti-Indium-DTPA).

Example 2

Production of $C_H3$-AD2-IgG

Transfection and Selection of Stable $C_H3$-AD2-IgG Secreting Cell Lines

All cell lines were grown in Hybridoma SFM (Invitrogen, Carlsbad Calif.). $C_{H3}$-AD2-IgG-pdHL2 vectors (30 µg) were linearized by digestion with Sal I restriction endonuclease and transfected into Sp2/0-Ag14 ($2.8 \times 10^6$ cells) by electroporation (450 volts, 25 g). The pdHL2 vector contains the gene for dihydrofolate reductase allowing clonal selection as well as gene amplification with methotrexate (MTX).

Following transfection, the cells were plated in 96-well plates and transgenic clones were selected in media containing 0.2 µM MTX. Clones were screened for $C_H3$-AD2-IgG productivity by a sandwich ELISA using 96-well microtitre plates coated with specific anti-idiotype MAbs. Conditioned media from the putative clones were transferred to the microplate wells and detection of the fusion protein was accomplished with horseradish peroxidase-conjugated goat anti-human IgG F(ab')$_2$ (Jackson ImmunoResearch Laboratories, West Grove, Pa.). Wells giving the highest signal were expanded and ultimately used for production.

Production and Purification of C3-AD2-IgG Modules

For production of the fusion proteins, roller bottle cultures were seeded at $2\times10^5$ cells/ml and incubated in a roller bottle incubator at 37° C. under 5% $CO_2$ until the cell viability dropped below 25% (~10 days). Culture broth was clarified by centrifugation, filtered, and concentrated up to 50-fold by ultrafiltration. For purification of $C_H3$-AD2-IgG modules, concentrated supernatant fluid was loaded onto a Protein-A (MABSELECT™) affinity column. The column was washed to baseline with PBS and the fusion proteins were eluted with 0.1 M Glycine, pH 2.5.

Example 3

Production of AD- and DDD-Linked Fab and IgG Fusion Proteins from Multiple Antibodies Using the techniques described in the preceding Examples, the IgG and Fab fusion proteins shown in Table 6 were constructed and incorporated into DNL™ constructs. The fusion proteins retained the antigen-binding characteristics of the parent antibodies and the DNL™ constructs exhibited the antigen-binding activities of the incorporated antibodies or antibody fragments.

TABLE 6

| Fusion proteins comprising IgG or Fab | |
|---|---|
| Fusion Protein | Binding Specificity |
| C-AD1-Fab-h679 | HSG |
| C-AD2-Fab-h679 | HSG |
| C-(AD)₂-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 4

Generation of DDD-Module Based on Interferon (IFN)-α2b

Construction of IFN-α2b-DDD2-pdHL2 for expression in mammalian cells The cDNA sequence for IFN-α2b was amplified by PCR resulting in sequences comprising the following features, in which XbaI and BamHI are restriction sites, the signal peptide is native to IFN-α2b, and 6 His is a hexahistidine tag: XbaI---Signal peptide---IFNα2b---6 His---BamHI (6 His disclosed as SEQ ID NO: 92). The resulting secreted protein consisted of IFN-α2b fused at its C-terminus to a polypeptide of the following sequence:

(SEQ ID NO: 93)
KSHHHHHHGSGGGGSGGGCGHIQIPPGLTELLQGYTVEVLRQQPPDLVEFAVEYFTRLR

EARA.

PCR amplification was accomplished using a full length human IFNα2b cDNA clone (INVITROGEN™ ULTI-MATE™ ORF human clone cat# HORF01Clone ID IOH35221) as a template and the following oligonucleotides as primers:

```
IFNA2 Xba I Left
                                         (SEQ ID NO: 94)
TCTAGACACAGGACCTCATCATGGCCTTGACCTTTGCTTTACTGG IFNA2 BamHI right
                                         (SEQ ID NO: 95)
GGATCCATGATGGTGATGATGGTGTGACTTTTCCTTACTTCTTAAACTT

TCTTGC
```

The PCR amplimer was cloned into the PGEM®-T vector. A DDD2-pdHL2 mammalian expression vector was prepared for ligation with IFN-α2b as follows. The $C_{H1}$-DDD2-Fab-hMN-14-pdHL2 (Rossi et al., Proc Natl Acad Sci USA 2006, 103:6841-6) vector was digested with Xba I and Bam HI, which removes all of the Fab gene sequences but leaves the DDD2 coding sequence. The IFN-α2b amplimer was excised from PGEM®-T with Xba I and Bam HI and ligated into the DDD2-pdHL2 vector to generate the expression vector IFN-α2b-DDD2-pdHL2.

Mammalian Cell Expression of IFN-α2b-DDD2

IFN-α2b-DDD2-pdHL2 was linearized by digestion with Sal I and stably transfected by electroporation into Sp/ESF myeloma cells (see U.S. patent application Ser. No. 11/877,728, the Examples section of which is incorporated herein by reference). Two clones were found to have detectable levels of IFN-α2b by ELISA. One of the two clones, designated 95, was adapted to growth in serum-free media without substantial decrease in productivity. The clone was subsequently amplified with increasing MTX concentrations from 0.1 to 0.8 μM over five weeks. At this stage, it was sub-cloned by limiting dilution and the highest producing sub-clone (95-5) was expanded. The productivity of 95-5 grown in shake-flasks was estimated to be 2.5 mg/L using commercial rIFN-α2b (Chemicon IF007, Lot 06008039084) as standards.

Purification of IFN-α2b-DDD2 from Batch Cultures Grown in Roller Bottles

Clone 95-5 was expanded to 34 roller bottles containing a total of 20 L of serum-free Hybridoma SFM with 0.8 μM MTX and allowed to reach terminal culture. The culture broth was processed and IFN-α2b-DDD2 was purified by immobilized metal affinity chromatography (IMAC) as follows. The supernatant fluid was clarified by centrifugation, 0.2 μM filtered, diafiltered into 1× Binding buffer (10 mM imidazole, 0.5 M NaCl, 50 mM NaH$_2$PO$_4$, pH 7.5), concentrated to 310 mL, added Tween 20 to a final concentration of 0.1%, and loaded onto a 30-mL Ni-NTA column. Following sample loading, the column was washed with 500 mL of 0.02% Tween 20 in 1× binding buffer and then 290 mL of 30 mM imidazole, 0.02% Tween 20, 0.5 M NaCl, 50 mM NaH$_2$PO$_4$, pH 7.5. The product was eluted with 110 mL of 250 mM imidazole, 0.02% Tween 20, 150 mM NaCl, 50 mM NaH$_2$PO$_4$, pH 7.5. Approximately 6 mg of IFNα2b-DDD2 was purified.

Production of IFN-α2b-DDD2 in E. Coli

IFN-α2b-DDD2 was also expressed by microbial fermentation as a soluble protein in E. coli. The coding sequence was amplified by PCR using IFN-α2b-DDD2-pdHL2 DNA as a template. The amplimer was cloned into the pET26b E. coli expression vector using Nde I and Xho I restriction sites. Protein was expressed intracellularly in BL21pLysS host cells by induction of LB shake flasks with 100 μM IPTG at 18° C. for 12 hours. Soluble IFN-α2b-DDD2 was purified from cell lysates by IMAC as described above.

Example 5

Generation of a DNL™ Conjugate Comprising Four IFN-α2b-DDD2 Moieties Linked to C$_H$3-AD2-IgG A DNL™ complex comprising four IFN-α2b-DDD2 moieties linked to C$_H$3-AD2-IgG (FIG. 1) was made as follows. Briefly, a select C$_H$3-AD2-IgG was combined with approximately two mole-equivalents of IFN-α2b-DDD2 and the mixture was reduced under mild conditions overnight at room temperature after adding 1 mM EDTA and 2 mM reduced glutathione (GSH). Oxidized glutathione was added to 2 mM and the mixture was held at room temperature for an additional 12-24 hours. The DNL™ conjugate was purified over a Protein A affinity column. Four such DNL™ conjugates designed 20-2b, 22-2b, hR1-2b, and 243-2b, each comprising four copies of IFN-α2b anchored on C$_H$3-AD2-IgG-hA20 (with specificity for CD20), C$_H$3-AD2-IgG-hLL2 (with specificity for CD22), C$_H$3-AD2-IgG-hR1 (with specificity for IGF-1R) and C$_H$3-AD2-IgG-hL243 (with specificity for HLA-DR), respectively, were prepared. SE-HPLC analyses of 20-2b generated from mammalian (m) or E. coli (e)-produced IFN-α2b-DDD2 each showed a major peak having a retention time consistent with a covalent complex composed of an IgG and 4 IFN-α2b groups (not shown). Similar SE-HPLC profiles were observed for the other three IFN-IgG conjugates.

Example 6

In Vitro Activity of the IFN-IgG Conjugates

Figure 2:
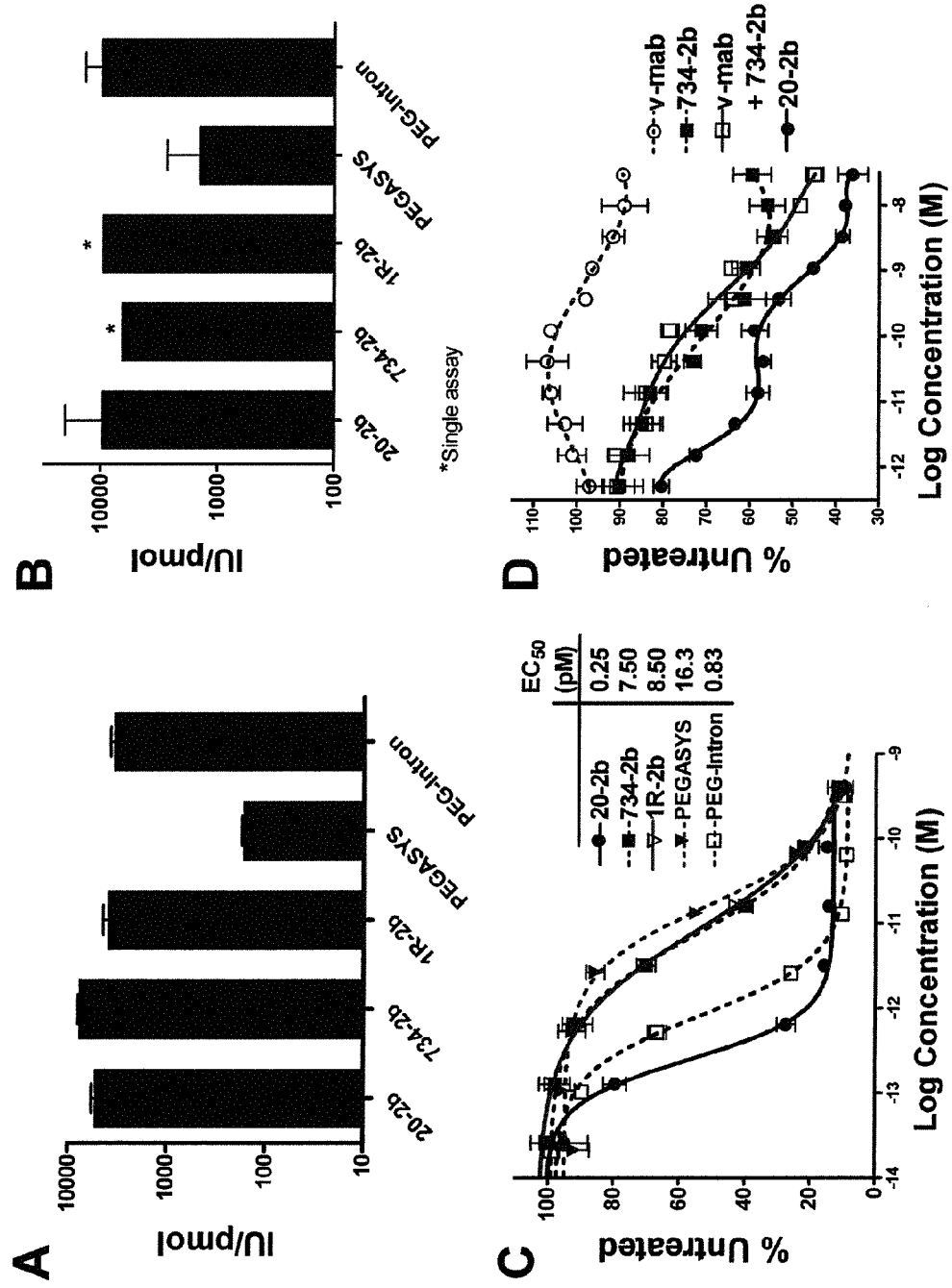
FIG. 2 shows in vitro IFNα activity in a cytokine-MAb DNL™ construct compared to PEGylated or native IFNα. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-mab (○), v-mab+734-2b (□), PEGASYS® (▼), PEG-Intron ® (▲) or 1R-2b (▽) and the relative viable cell densities were measured with MTS. The % of the signal obtained from untreated cells was plotted vs. the log of the molar concentration. Dose-response curves and $EC_{50}$ values were generated using Prism software. Error bars, SD.

The in vitro IFNα biological activity of 20-2b was compared to that of commercial PEGylated IFNα2 agents, PEGASYS® and PEGINTRON®, using cell-based reporter, viral protection, and lymphoma proliferation assays. Specific activities were determined using a cell-based kit, which utilizes a transgenic human pro-monocyte cell line carrying a reporter gene fused to an interferon-stimulated response element (FIG. 2A-2D). The specific activity of 20-2b (5300 IU/pmol) was greater than both PEGASYS® (170 IU/pmol) and PEGINTRON® (3400 IU/pmol) (FIG. 2A). 734-2b, 1R-2b and five additional MAb-IFNα constructs (data not shown), which were produced similarly to 20-2b, each exhibited similar specific activities (4000-8000 IU/pmol), demonstrating the consistency of the DNL™ method for generating such structures (FIG. 2A). Having four IFNα2b groups contributed to the enhanced potency of MAb-IFNα. When normalized to IFNα equivalents, the specific activity/IFNα was about 10-fold greater than PEGASYS® and only about 2-fold less than PEGINTRON™.

Comparison of MAb-IFNα, PEGASYS® and PEGINTRON® in an in vitro viral protection assay demonstrated that MAb-IFNα retains IFNα2b antiviral activity with specific activities similar to PEGINTRON® and 10-fold greater than PEGASYS® (FIG. 2B).

IFNα2b can have a direct anti-proliferative or cytotoxic effect on some tumor lines. The activity of 20-2b was measured in an in vitro proliferation assay with a Burkitt lymphoma cell line (Daudi) that is highly sensitive to IFNα (FIG. 2C). Each of the IFNα2 agents efficiently inhibited (>90%) Daudi in vitro with high potency (EC$_{50}$=4-10 pM). However, 20-2b (EC$_{50}$=0.25 pM) was about 30-fold more potent than the non-targeting MAb-IFNα constructs. The parent anti-CD20 MAb of 20-2b has anti-proliferative activity in vitro on many lymphoma cell lines, including Daudi (Rossi et al., 2008, Cancer Res 68:8384-92), at considerably greater concentrations (EC$_{50}$>10 nM). The in vitro activity of 20-2b was also assessed using Jeko-1, which is a mantle cell lymphoma line that has lower sensitivity to both IFNα and anti-CD20 (FIG. 2D). Jeko-1 is only modestly sensitive to the parent anti-CD20 MAb, having 10% maximal inhibition (I$_{max}$) with an EC$_{50}$ near 1 nM. As shown with 734-2b, Jeko-1 (I$_{max}$=43%; EC$_{50}$=23 pM) is less responsive to IFNα2b than Daudi (I$_{max}$=90%; EC$_{50}$=7.5 pM). Compared to 734-2b, 20-2b inhibited Jeko-1 to a greater extent (I$_{max}$=65%) and exhibited a biphasic dose-response curve (FIG. 2D). At <10 pM, a low-concentration response attributed to IFNα2b activity was observed, which plateaus at I$_{max}$=43%, similar to 734-2b. A high-concentration response was evident above 100 pM, where I$_{max}$ reached 65%. The low-concentration IFNα2b response of 20-2b (EC$_{50}$=0.97 pM) was 25-fold more potent than 734-2b, similar to the results with Daudi.

A combination of the parent anti-CD20 antibody and 734-2b (veltuzumab+734-2b) was assayed to elucidate whether the increased potency of 20-2b is due to an additive/synergistic effect of CD20 and IFNα signaling. The dose response curve for v-mab+734-2b was largely similar to 734-2b alone, except at >1 nM, where inhibition increased for the former but not the latter. These results suggest that MAb targeting is responsible for the lower EC$_{50}$ of 20-2b, but its greater I$_{max}$ is apparently due to the additive activity of IFNα2b and CD-20 signaling. The effect of CD20 signaling was only evident in the high-concentration response for 20-2b (EC$_{50}$=0.85 nM), which parallels the response to v-mab (EC$_{50}$=1.5 nM). A biphasic dose-response curve was not obvious for v-mab+734-2b, because the two responses overlap. However, an additive effect was evident at >1 nM concentrations. The I$_{max}$ of 20-2b (65%) was greater than the added responses of IFNα2b (I$_{max}$=43%) and veltuzumab (I$_{max}$=10%), suggesting possible synergism between the actions of IFNα2b and v-mab (veltuzumab).

ADCC Activity

IFNα can potentiate ADCC activity, which is a fundamental mechanism of action (MOA) for anti-CD20 immunotherapy, by activating NK cells and macrophages. We compared ADCC of 20-2b and v-mab with two NHL cell lines using peripheral blood mononuclear cells (PBMCs) as effector cells. Replicate assays using PBMCs from multiple donors consistently demonstrated that 20-2b had enhanced ADCC compared to v-mab, as shown for both Daudi and Raji cells (FIG. 4A). This effect was also shown with 22-2b, a MAb-IFNα comprising the anti-CD22 MAb, epratuzumab, which shows modest ADCC (Carnahan et al., 2007, Mol Immunol 44:1331-41.

CDC Activity

CDC is thought to be an important MOA for Type-I anti-CD20 MAbs (including v-mab and rituximab). However, this function is lacking in the Type-II MAbs, represented by tositumomab (Cardarelli et al., 2002, Cancer Immunol Immunother 51:15-24), which nonetheless has anti-lymphoma activity. Unlike v-mab, 20-2b does not show CDC activity in vitro (FIG. 4B). These results are consistent with those for other DNL structures based on the $C_H3$-AD2-IgG-v-mab module, in which complement fixation is apparently impaired, perhaps by steric interference (Rossi et al., 2008, Cancer Res 68:8384-92).

Example 7

Pharmacokinetic (PK) Analysis of 20-2b

Figure 3:
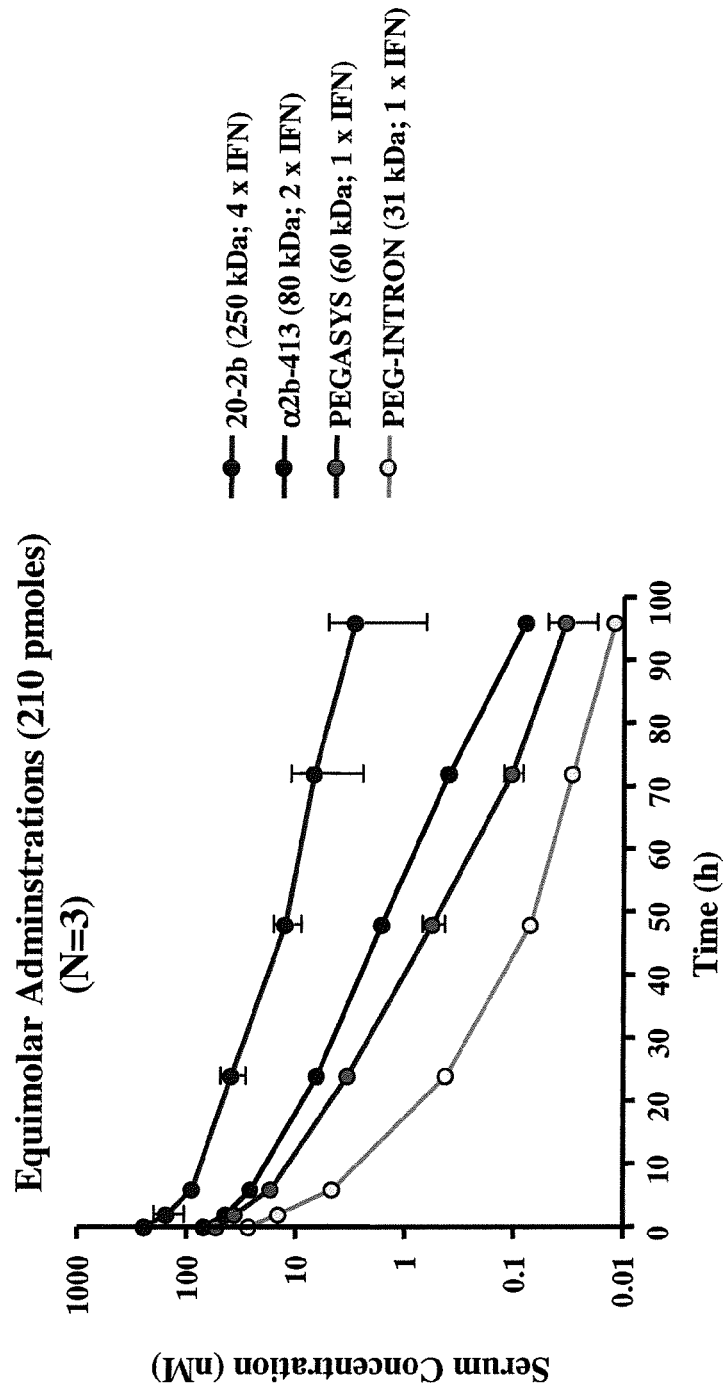
FIG. 3 shows the results of pharmacokinetic analyses in Swiss-Webster mice. Mice were administered 20-2b, α2b-413, PEGINTRON® or PEGASYS® and serum samples were analyzed for IFNα2b concentration by ELISA over 96 hours. Serum elimination curves are shown. Serum half-life ($T_{1/2}$) elimination rates and mean residence times (MRT) are summarized in the inserted table.

The pharmacokinetic (PK) properties of 20-2b were evaluated in male Swiss-Webster mice and compared to those of PEGASYS®, PEG-INTRON® and α2b-413 (Pegylated IFN made by DNL, see U.S. patent application Ser. No. 11/925, 408). Concentrations of IFN-α in the serum samples at various times were determined by ELISA following the manufacturer's instructions. Briefly, the serum samples were diluted appropriately according to the human IFN-α standard provided in the kit. An antibody bound to the microtiter plate wells captures interferon. A second antibody was then used to reveal the bound interferon, which was quantified by anti-secondary antibody conjugated to horseradish peroxidase (HRP) following the addition of Tetramethyl benzidine (TMB). The plates were read at 450 nm. FIG. 3 presents the results of the PK analysis, which showed significantly slower elimination and longer serum residence of 20-2b compared to the other agents. At an injected dose of 210 pmol, the calculated pharmacokinetic serum half-life in hours was 8.0 hr (20-2b), 5.7 hr (α2b-413), 4.7 hr (PEGASYS) and 2.6 hr (PEG-INTRON®). The elimination rate (1/h) was 0.087 (20-2b), 0.121 (α2b-413), 0.149 (PEGASYS®) and 0.265 (PEG-INTRON®). The calculated $MRT_{0.08} \to \infty$ (hr) was 22.2 (20-2b), 12.5 (α2b-413), 10.7 (PEGASYS®) and 6.0 (PEG-INTRON®). Because the pharmacokinetic parameters are determined more by the nature of the complex than the individual antibody or cytokine, it is expected that the PK characteristics of the cytokine-DNL complex are generalizable to other cytokine moieties and antibody moieties and are not limited to the specific 20-2b construct discussed above.

Example 8

In Vivo Activity of 20-2b

Serum Stability 20-2b was stable in human sera (>10 days) or whole blood (>6 days) at 37° C. (not shown). Concentration of 20-2b complex was determined using a bispecific ELISA assay. There was essentially no detectable change in serum 20-2b levels in either whole blood or serum over the time period of the assay.

Ex Vivo Efficacy of 20-2b Against Lymphoma Cells from Whole Human Blood

Figure 5:
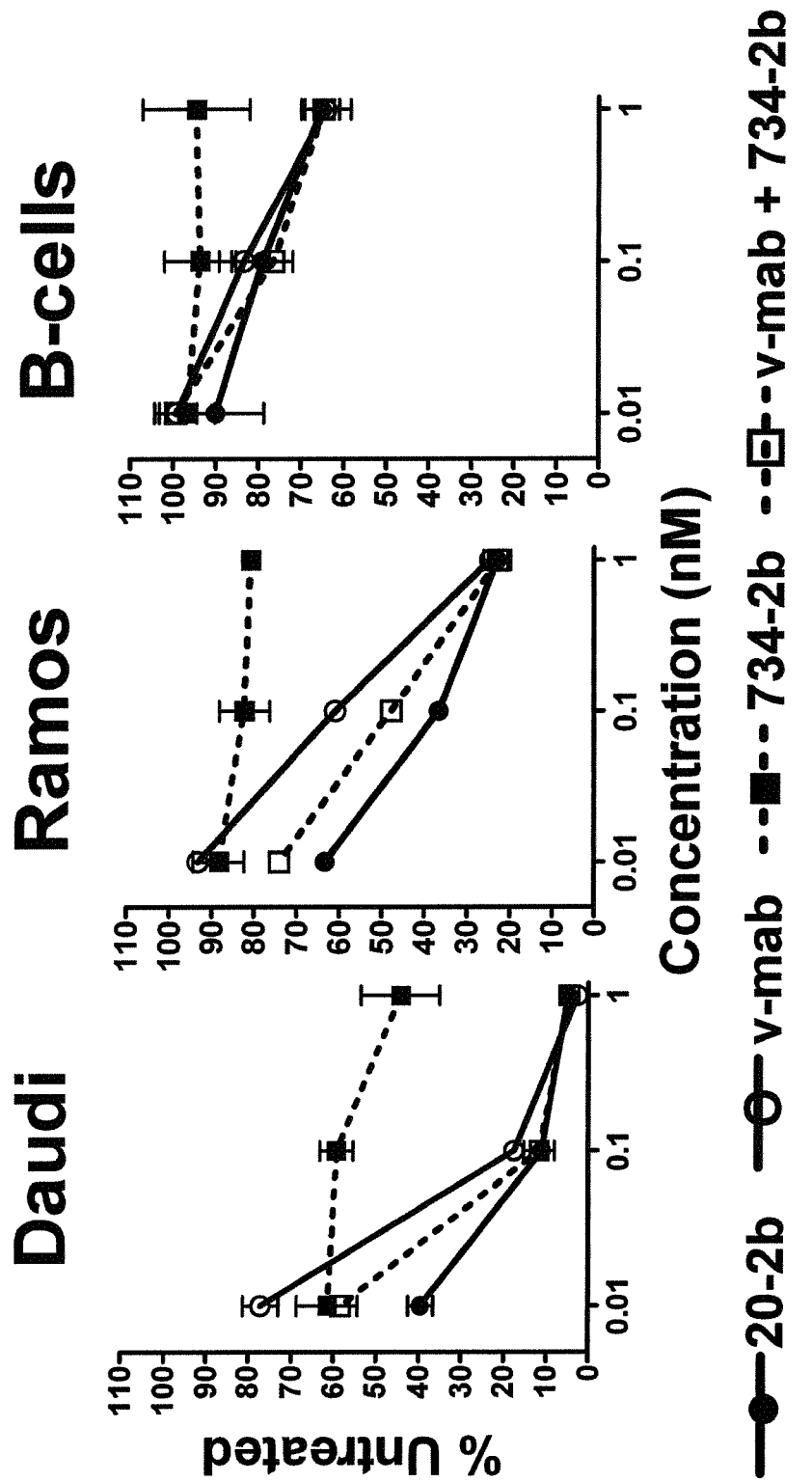
FIG. 5 shows enhanced depletion of NHL cells from whole blood by 20-2b. Fresh heparinized human blood was mixed with either Daudi or Ramos and incubated with 20-2b (●), v-mab (○), 734-2b (■) or v-mab+734-2b (□) at 0.01, 0.1 or 1 nM for two days. The effect of the indicated treatments on lymphoma and peripheral blood lymphocytes was evaluated using flow cytometry. Error bars, SD.

We compared the abilities of 20-2b, v-mab, 734-2b, or v-mab+734-2b to eliminate lymphoma or normal B-cells from whole blood in an ex vivo setting (FIG. 5). The therapeutic efficacy of naked anti-CD20 MAbs is believed to be achieved via three mechanisms of action (MOA)—signaling-induced apoptosis or growth arrest, ADCC, and CDC (Glennie et al., 2007, Mol Immunol 44:3823-37). In this assay, v-mab can employ all three MOA, while, based on the in vitro findings, 20-2b can potentially take advantage of signaling and enhanced ADCC, but not CDC. In this short-term model, the IFNα2b groups of 20-2b and 734-2b can act directly on tumor cells, augment the ADCC activity of v-mab, and possibly have some immunostimulatory effects. However, the full spectrum of IFNα-mediated activation of the innate and adaptive immune systems that might occur in vivo is not realized in this two-day ex vivo assay.

At 0.01 nM, 20-2b depleted Daudi cells (60.5%) significantly more than v-mab (22.8%), 734-2b (38.6%) or v-mab+734-2b (41.7%) (FIG. 5). At 0.1 nM, 20-2b and v-mab+734-2b depleted Daudi to a similar extent (88.9%), which was more than for v-mab (82.4%) or 734-2b (40.7%) (FIG. 5). At 1 nM, each agent depleted Daudi >95%, except for 734-2b (55.7%) (FIG. 5). Each of the differences indicated were statistically significant (P<0.01).

Ramos is less sensitive than Daudi to both IFNα2b and v-mab. The effect of 734-2b was only moderate, resulting in <20% depletion of Ramos at each concentration (FIG. 5). At both 0.01 and 0.1 nM, 20-2b depleted Ramos more than v-mab+734-2b, which in turn eliminated more cells than v-mab (FIG. 5). At 1 nM, all treatments besides 734-2b resulted in similar Ramos depletion (75%) (FIG. 5). Each of the differences indicated were statistically significant (P<0.02).

As demonstrated with 734-2b, IFNα2b alone does not deplete normal B-cells in this assay. At these low concentrations, 20-2b, v-mab, and v-mab+734-2b each show similar dose-responsive depletion of B-cells, which is markedly less than the depletion of either Daudi or Ramos. None of the treatments resulted in significant depletion of T-cells (data not shown).

In Vivo Efficacy of 20-2b in SCID Mice

Figure 6:
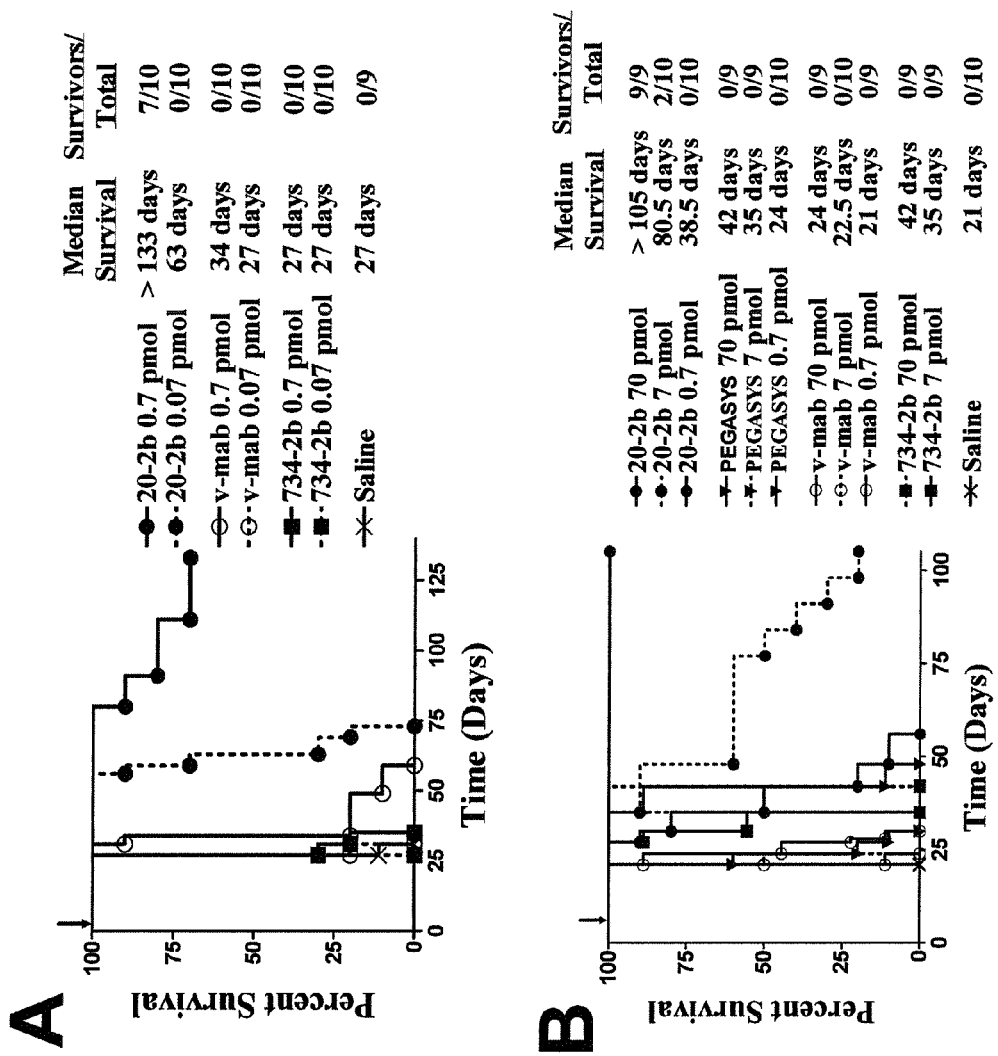
FIG. 6(A) illustrates survival curves showing therapeutic efficacy of 20-2b in a disseminated Burkitt's lymphoma (Daudi) xenograft model. Female C.B. 17 SCID mice were administered Daudi cells i.v. on day 0. Treatments consisted of 20-2b (●), 734-2b (□), v-mab (○), PEGASYS® (∇) or saline (X) given as a single s.c. doses. Days of treatment are indicated with arrows. Survival curves were analyzed using Prism software. In an Early Daudi model. Groups of 10 mice were given a single dose of 0.7 pmol (solid line) or 0.07 pmol (dashed line) on day 1.
FIG. 6(B) shows a similar study to FIG. 6(A), but in an Advanced Daudi model. Groups of 10 mice were given a single dose of 0.7 pmol (solid line), 7 pmol (dashed line) or 70 pmol (gray line) on day 7.

A limitation of the mouse model is the very low sensitivity of murine cells to human IFNα2b. The overall therapeutic advantage of 20-2b that might be achieved in humans can involve the enhancement of both innate and adaptive immunity. With these limitations in mind, we studied the anti-lymphoma in vivo efficacy of 20-2b against disseminated Burkitt lymphoma models in SCID mice. We initially tested a highly sensitive early Daudi model (FIG. 6A). One day after inoculation, groups were administered a single low dose of 20-2b, v-mab, or 734-2b. A single dose of v-mab (veltuzumab) or 734-2b at 0.7 pmol (170 ng) resulted in significant improvement in survival when compared to saline for v-mab (P<0.0001), but not for the irrelevant MAb-IFNα control, 734-2b (FIG. 6A). This improvement was modest, with the median survival time (MST) increasing from 27 days for saline to 34 days for v-mab. However, a single dose of 0.7 pmol (170 ng) of 20-2b improved the MST by more than 100 days over both saline control and v-mab groups (P<0.0001) (FIG. 6A). The study was terminated after 19 weeks, at which time the 7 long-term survivors (LTS) in the 0.7 pmol 20-2b treatment group were necropsied with no visible evidence of disease found (cured) (FIG. 6A). Remarkably, even the lowest dose of 0.07 pmol (17 ng) of 20-2b more than doubled the MST (FIG. 6A).

Next, we assessed the efficacy of 20-2b in a more challenging advanced Daudi model, in which mice were allowed to develop a substantially greater tumor burden prior to treatment (FIG. 6B). Seven days after tumor inoculation, groups were administered a single low dose (0.7, 7.0 or 70 pmol) of 20-2b, v-mab, 734-2b, or PEGASYS®. The MST for the saline control mice was 21 days (FIG. 6B). The highest dose (70 pmol) of PEGASYS® or 734-2b, each of which have enhanced Pk (compared to recombinant IFNα$_2$b) but do not target tumor, doubled the MST (42 days; P<0.0001) (FIG. 6B). Treatment with 20-2b at a 100-fold lower dose (0.7 pmol) produced similar results (38.5 days) as the highest dose (70 pmol) of either PEGASYS® or 734-2b (FIG. 6B). Treatment with 20-2b at a 10-fold lower dose (7 pmol) resulted in significantly improved survival (80.5 days, 20% LTS) over treatment with 70 pmol of PEGASYS® or 734-2b (P<0.0012) (FIG. 6B). At the highest dose tested (70 pmol), 20-2b improved the MST to >105 days with 100% LTS (FIG. 6B). We have demonstrated previously with the early tumor model that v-mab can increase survival of Daudi-bearing mice at relatively low doses (3.5 pmol) while higher doses result in LTS. However, in this advanced tumor model, a single dose of 70 pmol of v-mab had only a modest, though significant, effect on survival (MST=24 days, P=0.0001) (FIG. 6B).

Figure 7:
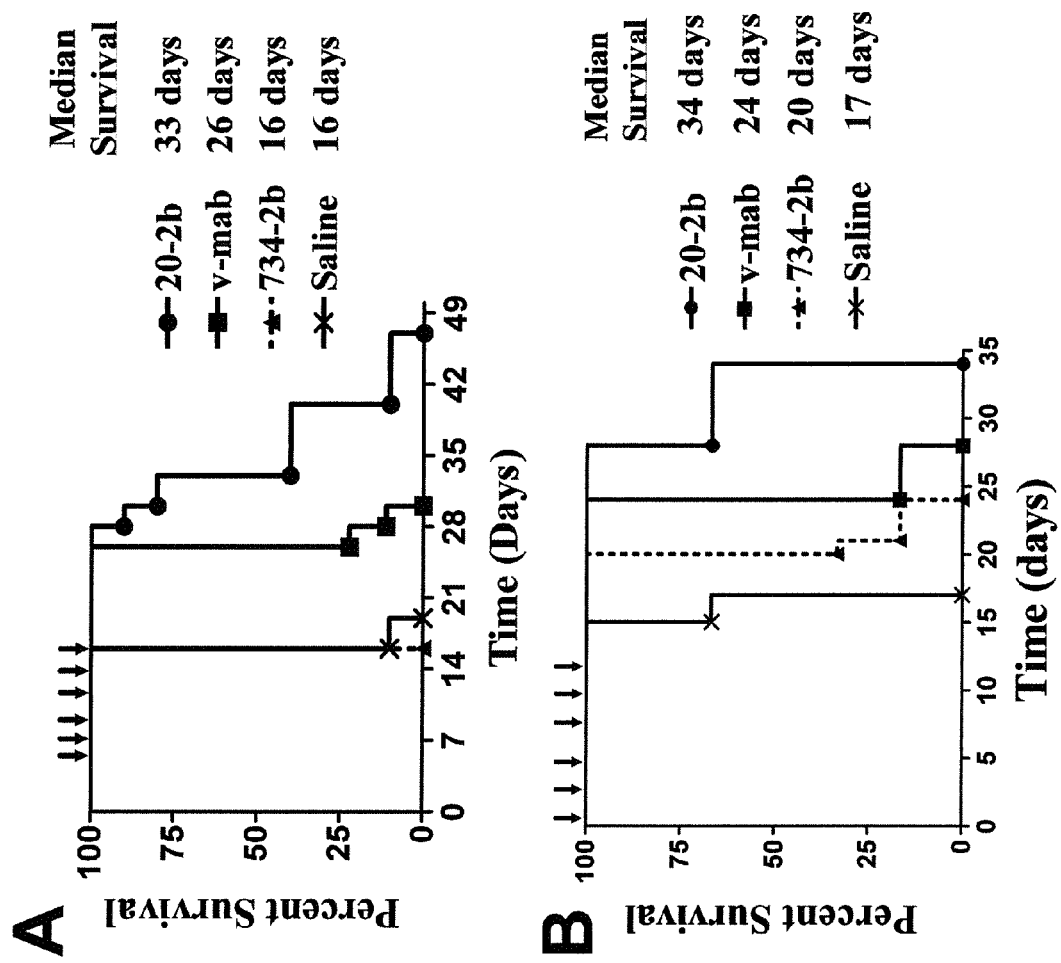
FIG. 7(A) presents survival curves showing therapeutic efficacy of 20-2b in disseminated Burkitt's lymphoma (Raji and NAMALWA) xenograft models. Female C.B. 17 SCID mice were administered NHL cells i.v. on day 0. Treatments consisted of 20-2b (●), 734-2b (■), v-mab (○) or saline (X) given as s.c. doses. Days of treatment are indicated with arrows. Survival curves were analyzed using Prism software. In an Advanced Raji model, groups of 10 received 250 pmol doses on days 5, 7, 9, 12, 14 and 16.
FIG. 7(B) shows a similar study to FIG. 7(A), but in an Early NAMALWA model. Groups of 6 received 250 pmol doses of 20-2b or 734-2b on days 1, 3, 5, 8, 10 and 12 or 3.5 nmol doses of v-mab on days 1, 5, 9, 13, 17, 21 and 25.

We subsequently assayed 20-2b in more challenging models, which are less sensitive than Daudi to direct inhibition by IFNα and less responsive to immunotherapy with v-mab. Raji is ~1000-fold less sensitive to the direct action of IFNα2b compared to Daudi. However, Raji has a similar CD20 antigen density to Daudi (Stein et al., 2006, Blood 108:2736-44) and is responsive to v-mab, albeit considerably less so than Daudi (Goldenberg et al., 2009, Blood 113, 1062-70). The efficacy of 20-2b was studied in an advanced Raji model with therapy beginning five days after tumor inoculation (FIG. 7A). Groups were administered a total of 6 injections (250 pmol each) over two weeks. 734-2b did not improve survival over saline (MST=16 days), consistent with the insensitivity of Raji to IFNα (FIG. 7A). V-mab significantly improved survival over saline (MST=26 days, P<0.0001) (FIG. 7A). 20-2b was superior to all other treatments (MST=33 days, P<0.0001) (FIG. 7A).

Finally, we investigated the efficacy of 20-2b with NAMALWA (FIG. 7B), a human lymphoma that has low sensitivity to the direct action of IFNα, ~25-fold lower CD20 antigen density compared to Daudi or Raji, and is considered to be resistant to anti-CD20 immunotherapy (Stein et al., 2006). Groups were administered a total of 6 doses (250 pmol each) of either 20-2b or 734-2b. Another group was administered a total of 7 doses (3.5 nmol each) of v-mab. The group treated with saline had an MST of 17 days (FIG. 7B). Treatment with 734-2b very modestly, though significantly, improved survival (MST=20 days, P=0.0012) (FIG. 7B). 20-2b (MST=34 days) was superior to 734-2b (P=0.0004) as well as v-mab (MST=24 days, P=0.0026), which was given at a 14-fold higher dose (FIG. 7B).

Conclusions

The results demonstrate unequivocally that targeting of IFNα with an anti-CD20 MAb makes the immunocytokine more potent and effective than either agent alone or in combination. MAb targeting of IFNα to tumors may allow a less frequent dosing schedule of a single agent, reduce or eliminate side effects associated with IFN therapy, and result in profoundly enhanced efficacy. Additionally, targeted IFNα can induce an acute tumor-directed immune response and possibly evoke immune memory via pleiotropic stimulation of innate and adaptive immunity (Belardelli et al, 2002, Cytokine Growth Factor Rev 12:119-34). Other groups have produced MAb-IFNα made by chemical conjugation that revealed some of the potential clinical benefits of such constructs (Pelham et al., 1983, Cancer Immunol Immunother 15:210-16; Ozzello et al., 1998, Breast Cancer Res Treat 48:135-47). A recombinant MAb-IFNα comprising murine IFNα and an anti-HER2/neu MAb exhibited potent inhibition of a transgenic (HER2/neu) murine B-cell lymphoma in immunocompetent mice and was also capable of inducing a protective adaptive immune response with immunologic memory (Huang et al., 2007, J Immunol 179:6881-88).

We expect that therapy with 20-2b will stimulate localized recruitment and activation of a number of immune cells, including NK, T4, T8, and dendritic cells, resulting in enhanced cytotoxicity and ADCC, and may potentially induce tumor-directed immunologic memory. However, murine cells are exceedingly less sensitive (~4 logs) than human cells to human IFNα2b (Kramer et al., 1983, J Interferon Res 3:425-35; Weck et al., 1981, J Gen Virol 57:233-37). Therefore, very little, if any, of the anti-lymphoma activity of 20-2b in the mouse model in vivo studies described above can be attributed to IFNα2b activation of the mouse immune response. Rather, killing is due primarily to the direct action of IFNα2b on the lymphoma cells.

We have shown that 20-2b has augmented ADCC, which may be the most important MOA of anti-CD20 immunotherapy. However, since human IFNα2b is only a very weak stimulator of the murine host's immune effector cells, an IFNα-enhanced ADCC is probably not realized as it might be in humans. Even with these limitations, the in vivo results demonstrate that 20-2b can be a highly effective anti-lymphoma agent, exhibiting more than 100-times the potency of v-mab or a non-targeting MAb-IFNα in the IFNα-sensitive Daudi model. Even with lymphoma models that are relatively insensitive to the direct action of IFNα (Raji/NAMALWA) or are resistant to anti-CD20 immunotherapy (NAMALWA), 20-2b showed superior efficacy to either v-mab or non-targeted MAb-IFNα.

Fusion of IFNα2b to v-mab increases its in vivo potency by extending circulation times and enabling tumor targeting. The therapeutic significance of Pk was demonstrated in the Daudi model, where the slower clearing PEGASYS® was superior to the faster clearing PEGINTRON®, which has a higher specific activity (data not shown). 20-2b was considerably more potent than either PEGASYS® or 734-2b, suggesting that lymphoma targeting via the anti-CD20 MAb is critical to its superior potency and efficacy. Surprisingly, the impact of targeting was evident even in the in vitro assays. In the in vitro proliferation experiments, which only allow for lymphoma inhibition via signaling, 20-2b showed activity at a 25-fold lower concentration compared to non-targeting MAb-IFNα, either alone or when combined with v-mab. The ex vivo setting allows the involvement of all three of the anti-CD20 MOA. Even without CDC activity, 20-2b was more effective at depleting lymphoma from blood than IFNα or v-mab, either alone or in combination, demonstrating the significance of targeting. The influence of MAb targeting in the in vitro/ex vivo studies is somewhat surprising, because the MAbs, effector, and target cells are all confined throughout the experiments. We expect that 20-2b will have a substantially greater impact in vivo in human patients.

The IFNα2b and v-mab components of 20-2b can apparently act additively or synergistically, to contribute to its enhanced potency. The in vitro proliferation assays suggest at least an additive effect, which was substantiated with the results of the ex vivo studies where the combination of v-mab and 734-2b was superior to either agent alone. This may be accomplished ex vivo via increased ADCC activity of v-mab as part of 20-2b or when combined with 734-2b, yet ADCC is not functional in the in vitro proliferation assays, suggesting additional mechanisms. The signal transduced by v-mab-bound CD20 may potentiate the IFNα signal, resulting in enhanced potency. Alternatively, the binding of v-mab, which is a slowly internalizing MAb, may prevent the internalization/down-regulation of the Type-I IFN receptors, resulting in a more prolonged and effective IFNα-induced signal.

Example 9

DNL Constructs of $(Fab)_2$-Interferon-λ1 Show Potent Bioactivity on Targeted Cells Summary and Introduction Interferon lambda 1 (IFN-λ1) is a type III interferon recently described as a member of the class II cytokine family, with therapeutic potential for antivirus and antitumor activity and immune system regulation. IFN-λs, like the type I IFNs, which comprise both IFN-α and IFN-β, trigger signal transduction via the JAK/STAT pathway, including the activation of JAK1 and TYK2 kinases, the phosphorylation of STAT proteins, and the activation of the transcription complex of IFN-stimulated gene factor 3 (Witte et al., 2010, Cytokine Growth Factor Rev 21:237-51; Zhou et al., 2007, J Virol 81:7749-58).

A major difference between type III and type I IFNs is the distribution of their respective receptor complexes. IFN-α/β signals through two widely expressed type I interferon receptors, which is at least partially responsible for the systemic toxicity associated with IFN-α/β therapy (Pestka, 2007, J Biol Chem 282:20047-51). In contrast, IFN-λs signal through a heterodimeric receptor complex comprising the IFN-λreceptor 1 (IFN-λR1) and the IL-10 receptor 2 (IL-10R2). Whereas IL-10R2 is ubiquitously expressed among hematopoietic and nonhematopoietic cells, IFN-λR1 has a highly restricted expression pattern, with the highest levels in epithelial cells, melanocytes, and hepatocytes, and the lowest level in primary central nervous system cells (Wolk et al., 2005, Genes Immun 6:8-18). Although blood immune cells express IFN-λR1, they exhibit impaired response to IFN-λs due to the secretion of a short spliced variant of IFN-λR1 that inhibits the effect of IFN-λ1 (Witte et al., 2009, Genes Immun 10:702-14). The limited responsiveness of neuronal cells and immune cells also contributes to the reduced toxicity of IFN-λs, compared to type I IFN (Witte et al., 2009, Genes Immun 10:702-14).

IFN-λs display structural features similar to IL-10-related cytokines, but exhibit type I IFN-like antiviral and anti-proliferative activity (Witte et al., 2010, Cytokine Growth Factor Rev 21:237-51; Ank et al., 2006, J Virol 80:4501-9; Robek et al., 2005, J Virol 79:3851-54). For example, studies have demonstrated that IFN-λ1 and IFN-λ2 can reduce viral replication or the cytopathic effect of various viruses, including DNA viruses, such as hepatitis B virus (Robek et al., 2005, J Virol 79:3851-54; Doyle et al., 2006, Hepatology 44:896-906) and herpes simplex virus 2 (Ank et al., 2006, J Virol 80:4501-9); positive-sense, single-stranded RNA viruses, such as encephalomyocarditis virus (EMCV) (Sheppard et al., 2003, Nat Immunol 4:63-68) and hepatitis C virus (HCV) (Robek et al., 2005, J Virol 79:3851-54; Doyle et al., 2006, Hepatology 44:896-906); negative-sense, single-stranded RNA viruses, such as vesicular stomatitis virus (Kotenko et al., 2003, Nat Immunol 6:69-77; Pagliaccetti et al., 2008, J Biol Chem 283:30079-89) and influenza-A virus (Jewell et al., 2010, J Virol 84:11515-22); and double-stranded RNA viruses, such as rotavirus (Pott et al., 2011, PNAS USA 108: 7944-49). IFN-λ3 was identified from genetic studies as a key cytokine in HCV infection (Ge et al., 2009, Nature 461:399-401), and has the most potent activity against EMCV (Dellgren et al., 2009, Genes Immun 10:125-31).

The anti-proliferative activity of IFN-λs has also been established in several human cancer cell lines, including neuroendocrine carcinoma BON1 (Zitzmann et al., 2006, BBRC 344:1334-41), glioblastoma LN319 (Meager et al., 2005, Cytokine 31:109-18), immortalized keratinocyte HaCaT (Maher et al., 2008, Cancer Biol Ther 7:1109-15), melanoma F01 (Guenterberg et al., 2010, Mol Cancer Ther 9:510-20), and esophageal carcinoma TE-11 (Li et al., 2010, Eur J Cancer 46:180-90). In animal models, IFN-λs induce tumor apoptosis and elimination through both innate and adaptive immune responses, suggesting that local delivery of IFN-λmight be a useful strategy for the treatment of human malignancies (Numasaki et al., 2007, J Immunol 178:5086-98; Sato et al., 2006, J Immunol 176:7686-94).

Human IFN-λ1 conjugated to a 20-kDa polyethylene glycol (PEG-IFN-λ1) is currently under clinical development for the treatment of chronic HCV infection. In a phase Ib study, antiviral activity was observed at each dose (0.5-3.0 μg/kg), with viral load reduced 2.3 to 4.0 logs when PEG-IFN-λ1 was administered to genotype 1 HCV patients who relapsed after IFN-α therapy (Muir et al., 2010, Hepatology 52:822-32; Ramos, 2010, J Interferon Cytokine Res 30:591-95). A phase IIb study (Zeuzem et al., 2011, J Hepatology 54:5538-39) reported that HCV patients (genotypes 1 and 4) had significantly higher response rates to treatment with PEG-IFN-λ1 versus PEG-interferon α-2a, and the additional advantages of PEG-IFN-λ1 over PEG-interferon α-2a included lower frequency of adverse events, decreased frequency of flu-like symptoms, anemia, and musculoskeletal symptoms, and rarely observed neutropenia and thrombocytopenia. However, higher rates of hepatotoxicity were seen with the highest-dose PEG-IFN-λ1 compared with PEG-interferon α-2a (Zeuzem et al., 2011, J Hepatology 54:5538-39). To improve the potency and safety profile of IFN-λ1, we constructed a modular DOCK-AND-LOCK™ (DNL™) complex to tether this cytokine to a targeting antibody in the format of a stabilized dimer of Fab protein.

Fab-DDD2 modules, derived from the humanized antibodies hRS7 (anti-Trop2), hMN15 (anti-CEACAM6), hL243 (anti-HLA-DR) or c225 (chimeric anti-EGFT), were dimerized and linked with AD2-IFN-λ1 to produce the immunocytokines (E1)-λ1, (15)-λ1, (C2)||1 and (c225)-λ1, respectively. The person of ordinary skill will realize that the invention is not limited to the exemplary antibodies, but could be performed with any known antibody. The bioactivities of the interferon-antibody constructs were evaluated and compared with recombinant human IFN-λ1 (rhIFN-λ1) in targeted and non-targeted cell lines. We observed that the hRS7 Fab dimer in (E1)-λ1 dramatically increased the in vitro potency (~1000-fold) of IFN-λ1 against several Trop2-positive cell lines, including human cervical carcinoma ME-180 ($EC_{50}$<0.1 μM), lung squamous carcinoma SK-MES-1 (maximum 60% inhibition), and esophageal carcinoma TE-11 (maximum 45% inhibition). Similarly, IFN-λ1-mediated growth suppression was remarkably enhanced by the hMN15 Fab dimer (~100-fold) in CEACAM6-positive ME-180 cells ($EC_{50}$<1 pM) and TE-11 cells, but not in CEACAM6-negative SK-MES-1 cells.

To examine the antiviral activities of $(Fab)_2$-IFN-λ1, we compared the effects of rhIFN-λ1, (15)λ1, and (C2)-λ1 on encephalomyocarditis virus (EMCV) infection and replication in A549 cells that express CEACAM6 but not HLA-DR. The results revealed that both rhIFN-Ad and $(Fab)_2$-IFN-λ1 could efficiently prevent EMCV-induced cytopathogenic effects, but (15)-λ1 demonstrated an antiviral efficacy that was 6-fold higher than rhIFN-α,1 and 10-fold higher than (C2)-λ1. Further investigation showed that, in targeted cells, (Fab)₂-IFN-λ1 could enhance the phosphorylation of signal transducer and activator of transcription (STAT) 1, 2, and 3, a critical event in the activation of Jak-STAT signal transduction, and the cell surface expression of major histocompatibility complexes class I (MHC I), which promotes antigen presentation. These data collectively show that cell surface immobilization of IFN-λ1, mediated by targeted binding of Fab antibody fragments, can significantly enhance its potency in targeted cells and improve in vivo safety profiles. The skilled artisan will realize that these effects are not limited to Fab antibody fragments, but will also occur with intact antibodies or other antibody fragments. These results show that DNL™ complexes comprising targeting antibodies or antibody fragments attached to IFN-λ1 can be exploited as therapeutic agents for treatment of cancer, infectious disease, asthma or multiple sclerosis.

Materials and Methods

Antibodies and Reagents—Humanized antibodies hA20-IgG (anti-CD20), hRS7-IgG (anti-Trop-2), hMN15-IgG (anti-CEACAM6) and hL243 (anti-HLA-DR) were from Immunomedics, Inc. Recombinant human IFN-λ1, mouse mAb against human IFN-λ1, and mouse FITC-IgG1k against human HLA-ABC were purchased from R&D Systems Inc. The amino acid sequences of fusion proteins comprising an AD2 moiety and poly-His sequence attached to mutant (C171S) or wild-type IFNλ1 are shown below. Rabbit antibodies against STAT1, STAT3, pY-STAT1 and pY-STAT3 were purchased from Cell Signaling Technology Inc. STAT2 antibody was from SANTA CRUZ BIOTECHNOLOGY®. pY-STAT2 antibody was from EMD MILLIPORE®.

Wild type: AD2-IFN-λ1

```
                                                    (SEQ ID NO: 96)
MCGQIEYLAKQIVDNAIQQAGCEFPKPSTPPGSSGGAPAMDGPVPTSKPTTTGKGCHIGR

FKSLSPQELASFKKARDALEESLKLKNWSCSSPVFPGNWDLRLLQVRERPVALEAELAL

TLKVLEAAAGPALEDVLDQPLHTLHHILSQLQACIQPQPTAGPRPRGRLHHWLHRLQEA

PKKESAGCLEASVTFNLFRLLTRDLKYVADGNLCLRTSTHPESTVEHHHHHH
```

Mutant: AD2-IFN-λ1-C171S

```
                                                    (SEQ ID NO: 97)
MCGQIEYLAKQIVDNAIQQAGCEFPKPSTPPGSSGGAPAMDGPVPTSKPTTTGKGCHIGR

FKSLSPQELASFKKARDALEESLKLKNWSCSSPVFPGNWDLRLLQVRERPVALEAELAL

TLKVLEAAAGPALEDVLDQPLHTLHHILSQLQACIQPQPTAGPRPRGRLHHWLHRLQEA

PKKESAGCLEASVTFNLFRLLTRDLKYVADGNLSLRTSTHPESTVEHHHHHH
```

Expression and Purification of AD2-IFN-λ1—To produce the IFN-λ1 module for DNL™ complex formation, a synthetic DNA sequence containing AD2, hinge linker, and human INF-λ1 (C171S) optimized for expression in *E. coli* was synthesized (FIG. 8A) and cloned into the Msc I and Xho I sites of the pET-26b vector. Rosetta-pLysS cells (Novagen) transformed with the plasmid were grown at 37° C. in Difco 2xYT broth (Becton Dickinson) supplemented with 100 kanamycin sulphate and 34 μg/ml chloramphenicol. When the cell density reached $OD_{600}$ of 1.0, IPTG was added to 0.5 mM and protein expression was induced at 30° C. for 4 hours. The cells were harvested by centrifugation and frozen at −80° C. overnight. The pellets were thawed and homogenized in lysis buffer (2% Triton-X 100, 5 mM $MgSO_4$, 10 units/ml benzonase (Novagen), 100 μM AEBSF, 20 mM Tris-HCl, pH 8.0). The homogenate was centrifuged at 18,000 RPM for 30 minutes and the pellet was re-homogenized in PBS/1% Triton X-100 and then re-pelleted. The pellet was solubilized in 20 ml of 6 M guanidine-HCl, 100 mM Na-phosphate, pH 8.0 and loaded onto a His-Select affinity column (GE-Healthcare), which was subsequently washed with 6 M guanidine, 50 mM Na-phosphate, pH 8.0. The protein was eluted in 4 M guanidine-HCL 100 mM $NaH_2PO4$, pH 4.5, and neutralized by the addition of 200 μL of 3 M Tris-HCl, pH 8.6, DTE was added to 60 mM and the solution was held at room temperature overnight. The reduced, denatured protein solution was rapidly diluted into 0.5 M arginine, 20 mM oxidized glutathione, 2 mM EDTA; 100 mM Tris, pH 8.0, then dialyzed against 5 L of renaturation buffer (0.5 M arginine, 2 mM oxidized glutathione, 0.6 mM DTE, 2 mM EDTA, 20 mM Tris, pH 8.0) and held for 72 hrs at 4° C. The solution was then dialyzed against PBS-AG-2 buffer (35.2 mM $Na_2PO_4.7H_2O$; 0.4 M NaCl; 6.5 mM $NaH_2PO4.H_2O$; 150 mM arginine; 150 mM glutamic acid, pH 8.0). The final product was concentrated to about 0.5 mg/ml and analyzed by SDS-PAGE.

DNL™ Constructs— The $(Fab)_2$-IFN-λ1 conjugates, including (E1)-λ1, (15)-λ1, and (C2)-λ1, were generated by the fusion of hRS7-, hMN15-, or hL243-Fab-DDD2 modules with a AD2-IFN-λ1 module to form a DNL™ complex (FIG. 8B), as described previously (see, e.g., U.S. Pat. Nos. 7,521,056; 7,527,787; 7,550,143; 7,534,866; 7,666,400; 7,858,070; 7,871,622; 7,901,680; 7,906,118; 7,906,121; 7,981,398 and 8,003,111, the Examples section of each of which is incorporated herein by reference). The c225-Fab-DDD2 module was constructed according to the sequences from DrugBank (Access number: DB00002). The products were purified sequentially on Kappa-select and His-select columns and analyzed with SDS-PAGE under reducing and nonreducing conditions using 4-20% Tris-glycine gels (not shown).

Cell Culture and Surface Binding—TE-11 was graciously provided by Dr. Hiroshi Nakagawa (University of Pennsylvania). Huh-7 and T.Tn were purchased from the Japanese Collection of Research Bioresources. All other cell lines were purchased from American Type Culture Collection. ME-180, TE-11, and A375 cells were grown in RPMI 1640 media (INVITROGEN™) with 10% FBS (HYCLONE™). HepG2, Huh-7, and SK-MES-1 cells were grown in EMEM media (ATCC) with 10% FBS. A549 was grown in F12 media (INVITROGEN™) with 10% FBS, and T.Tn was grown in DMEM/F12 media (INVITROGEN™) with 10% FBS. All cell lines were cultured in a humidified atmosphere of 5% $CO_2$ at 37° C.

For binding assays, cells were briefly trypsinized, suspended in fresh medium and pelleted, then re-suspended with 10 μg/ml of humanized mAbs or serially diluted IFN-λ1-based agents in 1% BSA-PBS. After incubation for 45 min at 4° C., cells were pelleted and washed twice with 1% BSA-PBS, incubated for another 45 min at 4° C. with FITC labeled goat anti-human IgG-Fc or mouse antihuman IFN-λ1, then probed with FITC labeled goat anti-mouse IgG-Fc. After three washes, binding was measured by flow cytometry. To examine the changes of MHC I expression, cells were exposed to IFN-λ1 agents for 3 days, and their surface MHC 1 was detected by binding with FITC labeled mouse IgG1k against human HLA-ABC. FITC labeled non-specific mouse IgG1k was used as negative control.

In Vitro Proliferation— ME-180, SK-MES-1, TE-11, and T.Tn cells were seeded in 96-well plates at 1000 cells/well and incubated at 37° C. overnight, then exposed to IFN-α1 agents at increasing concentrations for 4 days. Viable cell densities were determined using a CellTiter 96 Cell Proliferation Assay (Promega).

Antiviral Assays— The anti-HCV activities of IFN-λ1 and 2(Fab)-λ1 were measured by HD Biosciences (China) Co., Ltd (Shanghai, China), using a stable Huh-7 cell line containing HCV genotype 1b Con1 replicon, designated as Huh-7-Con1. A firefly luciferase gene was integrated into this replicon as a reporter of viral level. Three IFN-λ1 agents, (c225)-λ1, (C2)-λ1, and rhIFN-λ1, were included in this assay. Among them, (c225)-λ1 comprises two Fabs of chimeric mAb that specifically targets EGFR on Huh-7 cell surface, while (C2)-λ1 and rhIFN-λ1 were two non-targeting controls. Huh-7-Con1 cells were treated with three agents for 3 days, and the viral replication level was determined by measuring luciferase activity. Meanwhile, the cytotoxicity of these agents was also evaluated on parental Huh-7 cells using CELLTITER-GLO® kit (Promega).

In another assay, the antiviral activity of (15)-λ1 was measured on A549 cells with EMCV using the cytopathic effect inhibition assay, which was performed by PBL Interferon Source (Piscataway, N.J.). Included in the assay were hMN-15-Fab-DDD2 as a negative control, rhIFN-λ1 standard (PBL Interferon Source) as a positive control, and (C2)-λ1 as a non-targeting control for structural counterpart.

Western Blot— ME-180, HepG2, and A375 cells were plated into 6-well plates at 5×10$^5$ cells/well and incubated at 37° C. overnight. To evaluate STAT activation, cells were treated with the indicated IFN-λ1 agents at decreasing concentrations for 1 hour, and then lysed with PhosphoSafe™ extraction reagent (EMD). Cell lysates were resolved on SDS-PAGE, transferred onto a nitrocellulose membrane (Bio-Rad), and then blotted with rabbit antibodies against total STAT1, STAT2, or STAT3 and the phosphotyrosine-specific antibodies pY-STAT1, pY-STAT2, or pY-STAT3, detected with HRP-goat anti-rabbit antibody. The β-actin antibody was used for loading control.

Four groups of 8-week-old female athymic nude mice (Taconic, Germantown, N.Y.) were injected subcutaneously with 2.4 nmol of (E1)-λ1 and bled at 6, 16, 24, and 48 hours. Serum concentrations of intact (E1)-λ1 were measured using enzyme-linked immunosorbent assay (ELISA). Pharmacokinetic parameters were calculated using WINNONLIN® Noncompartmental Analysis Program (Version 5.3, Pharsight Corporation, St. Louis, Mo.). To corroborate with the results of ELISA, the bioactivity of IFN-λ1 in selective serum samples was also evaluated by ex vivo proliferation assay of ME-180 cells, using (E1)-λ1 as a standard.

RT-PCR Analysis. HepG2 cells were treated with IFN-λ1 agents for 24 h and total RNA was isolated using TRIzol® Reagent (Life Technologies). The mRNA expression of the myxovirus resistance A (MxA) gene was analyzed using SuperScript® III One-Step RT-PCR System (Life Technologies) with forward and reverse primers at conditions: cDNA synthesis-55° C./30 min for one cycle and PCR-94° C./15 sec, 62° C./30 sec, 68° C./30 sec for 25 cycles. A 452-bp fragment of the glyceraldehyde-3-phosphate dehydrogenase (GAPDH) cDNA was amplified at similar conditions as an internal control.

Pharmacokinetics in mice. Four groups of 8-week-old female athymic nude mice (Taconic, Germantown, N.Y.) were injected subcutaneously with 2.4 nmol of (E1)-λ1 and bled at 6, 16, 24, and 48 hours. Serum concentrations of intact (E1)-λ were measured using enzyme-linked immunosorbent assay (ELISA). Pharmacokinetic parameters were calculated using WINNONLIN® Noncompartmental Analysis Program (Version 5.3, Pharsight Corporation, St. Louis, Mo.). To corroborate with the results of ELISA, the bioactivity of IFN-λ1 in selective serum samples was also evaluated by ex vivo proliferation assay of ME-180 cells, using (E1)-λ1 as a standard.

Statistical Analyses. Statistical significance (P<0.05) was determined with F tests for all results using the Prism Graph-Pad software package (Advanced Graphics Software, Rancho Santa Fe, Calif.).

Results

Generation and Characterization of (Fab)$_2$-IFN-λ1— A point mutation (C171S) was introduced into the wild type IFN-λ1 sequence to eliminate the potential interference of the unpaired cysteine residue with the refolding and assembly of the DNL modules. The recombinant form of AD2-IFN-λ1 module was produced in E. coli and purified from inclusion bodies under denaturing conditions by immobilized metal ion affinity chromatography (IMAC). The protein was reduced with dithiothreitol (DTE) and then refolded in a refolding buffer containing oxidized glutathione to allow the formation of disulfide bonds. As determined by SDS-PAGE (not shown), the AD2-IFN-λ1 protein was highly purified and existed mainly in a monomeric state. The yield of final product was about 6 mg/ml E. coli cell culture.

Figure 8A:
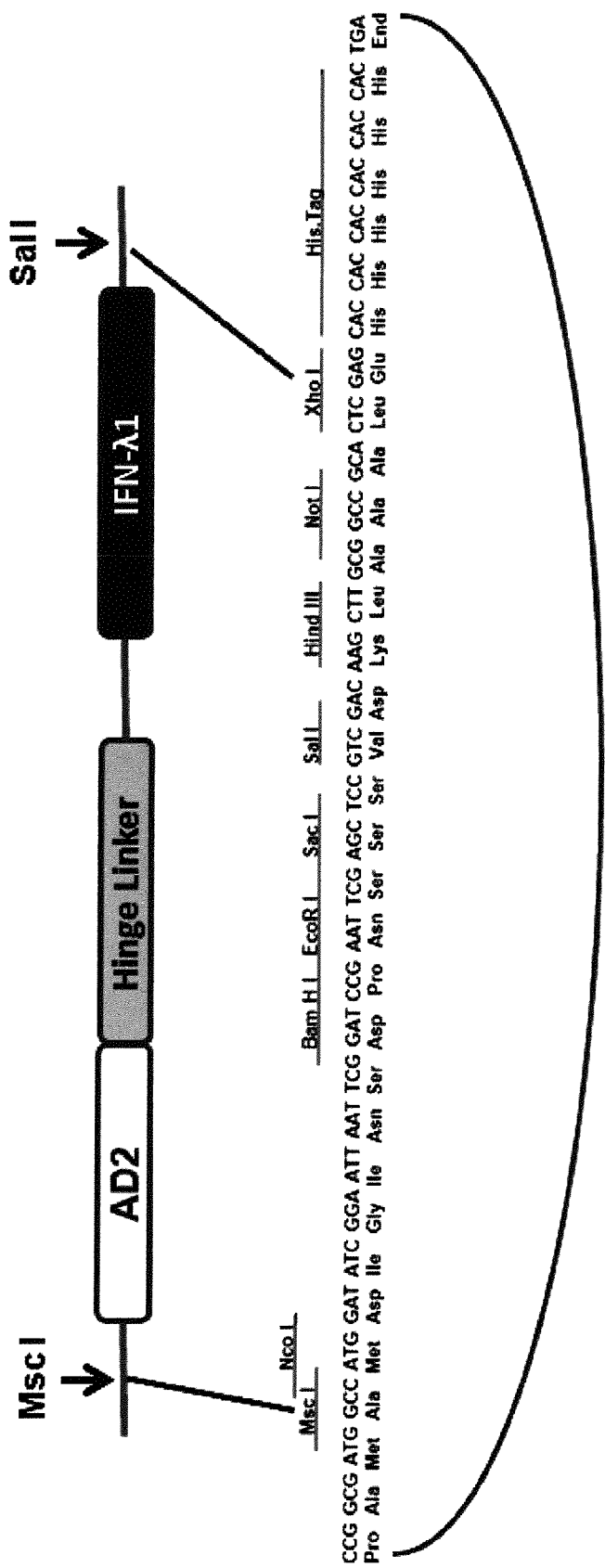
FIG. 8 (A) Schematic illustration of AD2-IFN-λ1 expression module. Figure discloses SEQ ID NOS 99-100, respectively, in order of appearance. (B) Schematic diagram showing construction of interferon-antibody DNL™ module.
Figure 8B:
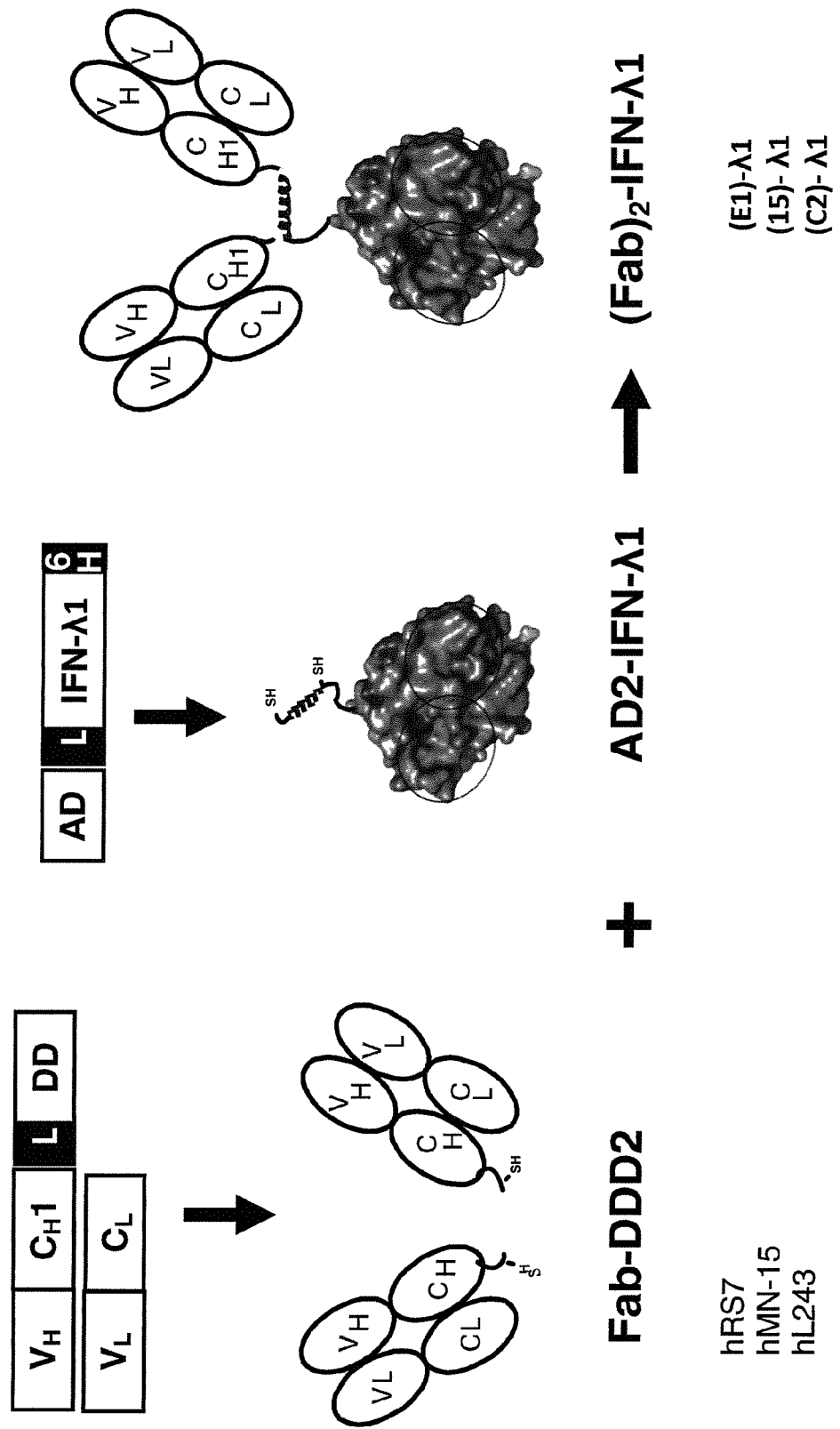

As illustrated in FIG. 8B, the (Fab)$_2$-IFN-λ1 conjugate was generated by combining the AD2-IFN-λ1 module with the Fab-DDD2 module. In the current study, the Fab-DDD2 module of hRS7, hMN15, or hL243 was mixed with an excess molar quantity of AD2-IFN-λ1, and incubated overnight with 1 mmol/L of reduced glutathione before the addition of oxidized glutathione (2 mmol/L). The reaction mixtures were purified on a Kappa-select column, and four conjugates (E1)-λ1, (15)-λ1, (C2)-λ1 and (c225)-λ1 were successfully generated. The purity of these conjugates was shown by SDS-PAGE, which resolved three bands (Fab DDD2-heavy chain, Fab light chain, and AD2-IFN-λ1) in reducing gels and a major high molecular weight band in non-reducing gels (not shown).

Cell Surface Expression of Antigens— The expression levels of Trop-2, CEACAM6, HLA-DR, and EGFR on the cell surface of seven human cancer cell lines (cervix, ME-180; esophagus, TE-11; lung, A549, SK-MES-1; liver, HepG2, Huh-7; and melanoma-skin, A375) were determined by flow cytometry. As shown in FIG. 9, Trop-2 is highly expressed on ME-180 and TE-11 cells, and moderately expressed on SK-MES-1 cells. Except for A375 and SK-MES-1, CEACAM6 is expressed on all other cell lines with the highest levels on A549 and HelpG2 cells. The A375 cell line showed high expression of HLA-DR. High expression of EGFR was observed to Huh-7, ME-180, TEAL SK-MES-1 and A549. These data provided the basis for our further study of cell-specific targeting of (Fab)$_2$-IFN-λ1.

Figure 10A:
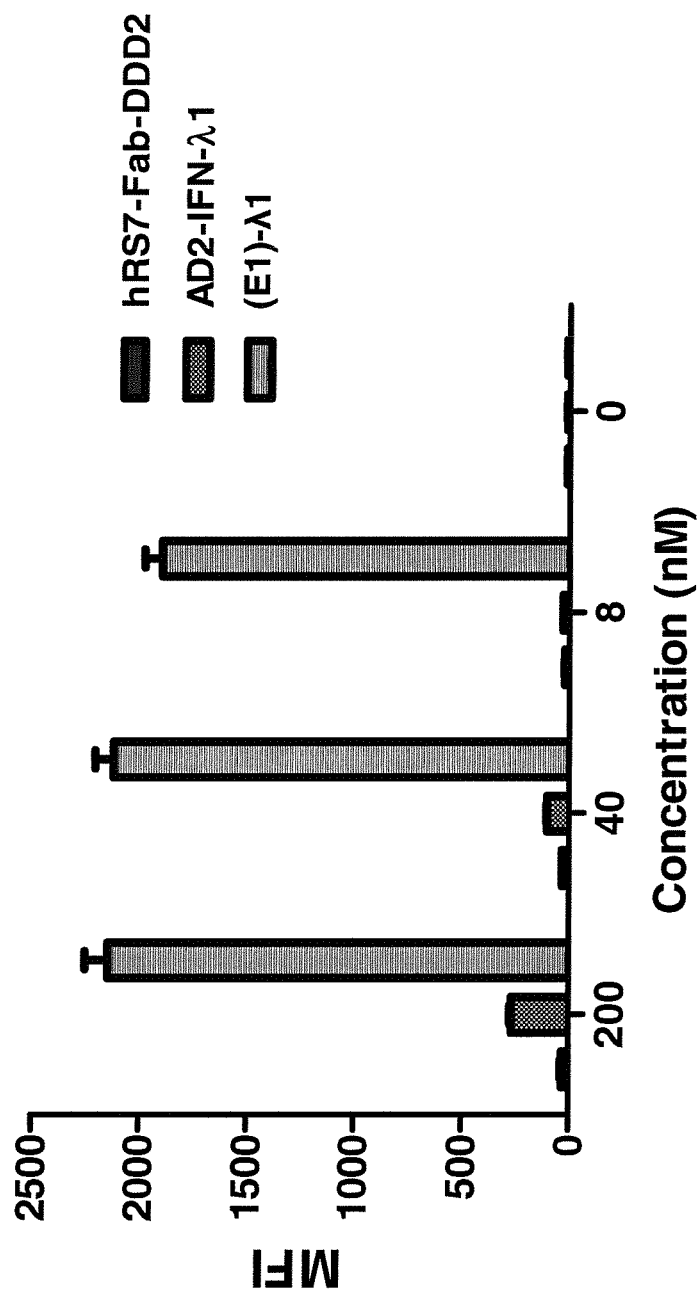
FIG. 10 Enhanced binding activity of (A) (E1)-λ1 to ME-180 cells (B) (15)-λ1 to HepG2 cells and (C) (C2)-λ1 to A375 cells compared to AD2-λ1 module.
Figure 10B:
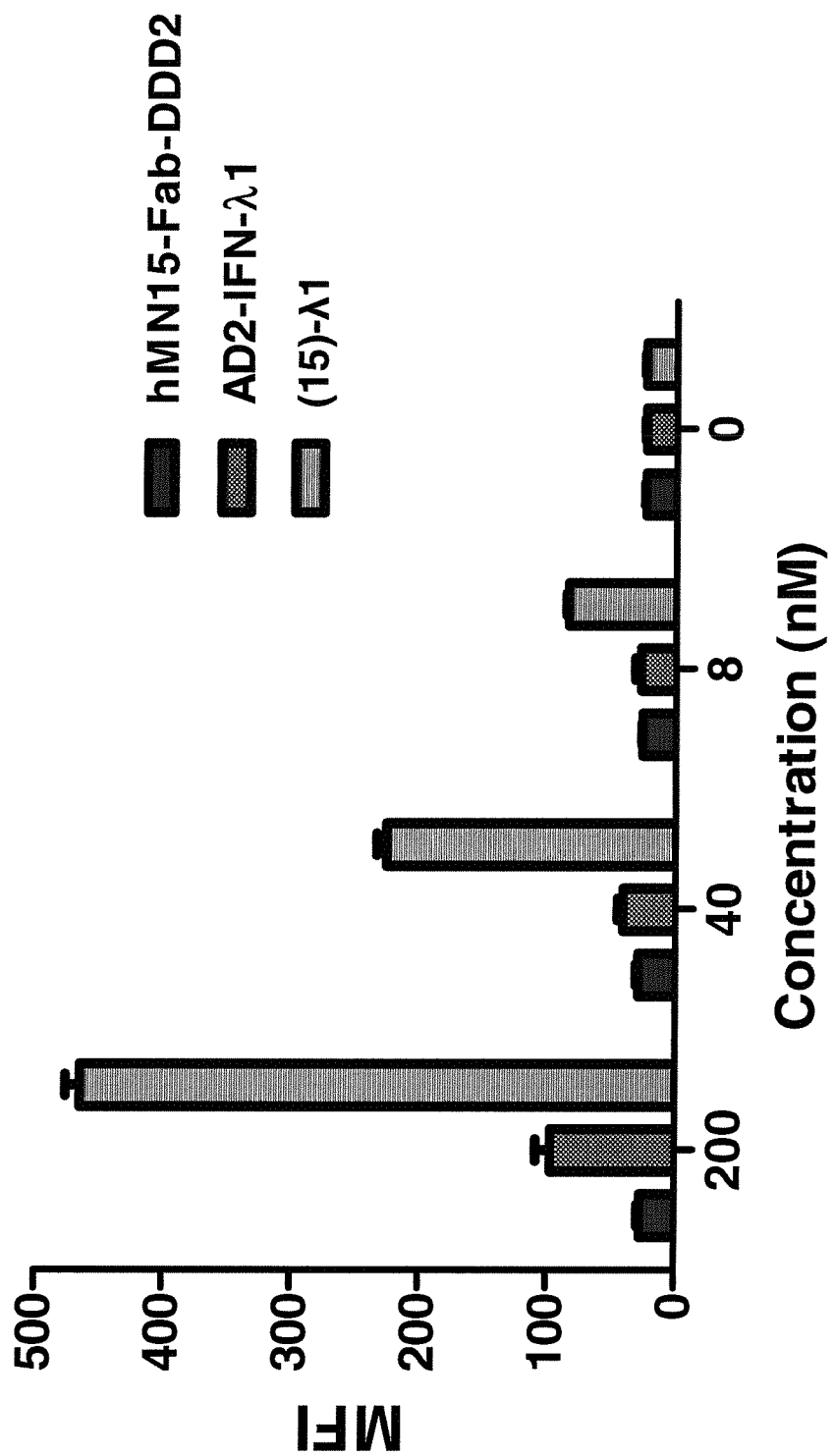
Figure 10C:
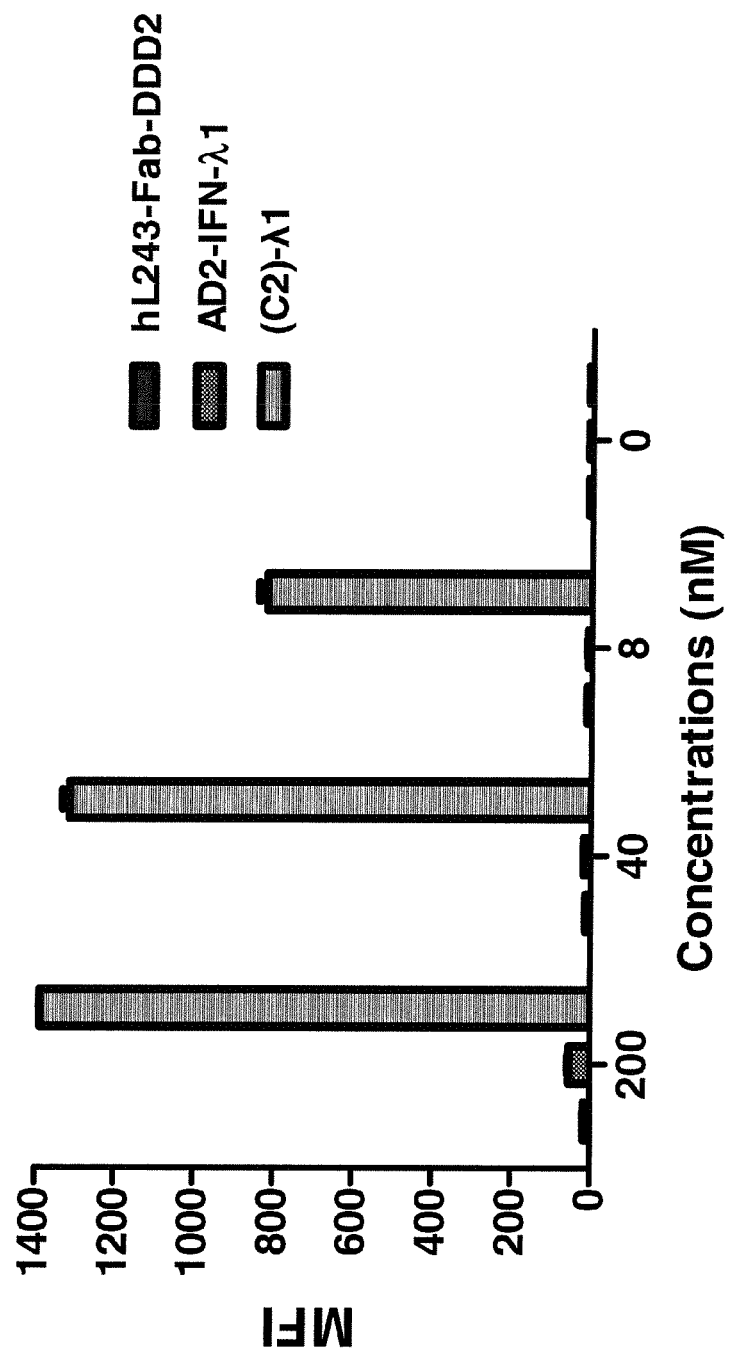

Enhanced Immobilization of (Fab)$_2$-IFN-λ1 on Cell Surface— In comparison with the AD2-IFN-21 module, (Fab)$_2$-IFN-λ1 showed significantly enhanced binding affinity to targeted cells. At a concentration of 8 nM, as detected by mouse anti-human IFN-λ1 mAb, the binding signals were 107-fold higher for (E1)-21 to ME-180 (FIG. 10A), 15-fold higher for (15)-λ1 to HepG2 (FIG. 10B), and 508-fold higher for (C2)-λ1 to A375 cells (FIG. 10C) compared to the AD2-IFN-λ1 module. These data show that IFN-λ1 conjugated with (Fab)$_2$ exhibits dramatically enhanced immobilization on the targeted cell surface.

Figure 11:
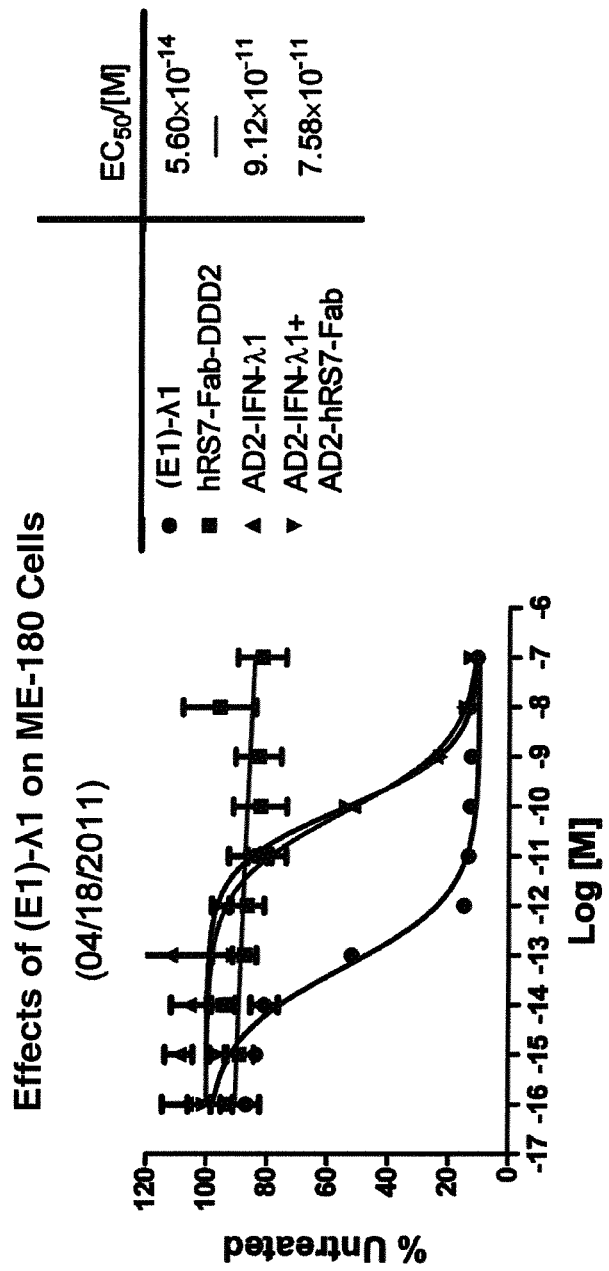
FIG. 11 Cytotoxic effect of (E1)-λ1 on ME-180 cells.
Figure 12:
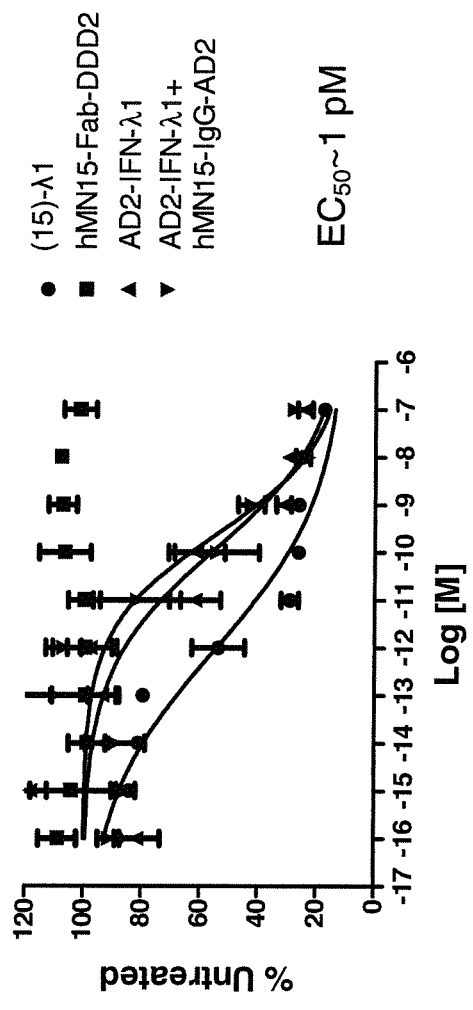
FIG. 12 Cytotoxic effect of (15)-λ1 on ME-180 cells.

In Vitro Growth Suppression and Cytotoxicity— Cervical carcinoma ME-180 was identified as a cell line highly sensitive to IFN-λ1. The cell growth was almost completely suppressed by rhIFN-λ1 at concentrations above 10 nM, and the AD$_2$-IFN-λ1 module showed activity equal to rhIFN-λ1 ($EC_{50}$=0.1 nM, data not shown). The specific activity of IFN-λ1 on ME-180 was significantly enhanced in the targeting conjugate (E1)-λ1 ($EC_{50}$<0.1 pM), which is >1000-fold greater than AD2-IFN-λ1 or the combination of AD2-IFN-λ1 and AD2-hRS7-Fab (FIG. 11). In comparison with ME-180, the lung squamous carcinoma SK-MES-1 and esophageal carcinoma TE-11 cells were less sensitive to ITN-λ1 and only showed maximum 60% and 45% growth inhibition respectively at the highest concentration of IFN-λ1 (not shown). However, the enhanced activity of (E1)-λ1 was still observed in these two cell lines, about 1000-fold higher than AD2-IFN-λ1 or the combination of AD2-IFN-λ1 and AD2-hRS7-Fab (not shown). Further, we evaluated the activity of (15)-λ1 on CEACAM6-positive ME-180 and TE-11 cell lines. As shown in FIG. 12, (15)-λ1 exhibited activity 100-fold higher than AD2-IFN-λ1 or the combination of AD2-IFN-λ1 and hMN15-IgG-AD2. The $EC_{50}$ of (15)-λ1 on ME-180 was about 1 pM, which is 10-fold higher than (E1)-λ1.

Antiviral Activity— The antiviral activity of selective 2(Fab)-λ1 constructs was measured against HCV and EMCV in Huh-7 and A549 cells, respectively. In EGFR-expressing Huh-7 cells, (c225)-λ1 ($EC_{50}$=0.56 pM) was 163- and 123-fold more potent than the non-targeting (C2)-λ1 ($EC_{50}$=91.2 pM) and commercial rhIFN-λ1 ($EC_{50}$=69.2 pM), respectively, at inhibiting HCV replication (FIG. 13A). In CEACAM6-expressing A549 cells, (15)-λ1 compared to the non-targeting (C2)-λ1 and rhIFN-λ1 showed 10- and 6-fold higher anti-EMCV activity, respectively (FIG. 13B). Notably, (C2)-λ1 retains 65 to 75% antiviral activity of rhIFN-λ1. These results indicate that cell surface targeting of IFN-λ1 can effectively enhance its antiviral activity.

Cell Signaling— To understand the mechanism of (Fab)$_2$-enhanced IFN-λ1 activity, we compared the signaling activity of (Fab)$_2$-IFN-λ1 and AD2-IFN-λ1 in three cell lines. The phosphorylation assay showed that 15-Fab-DDD2 did not induce any STAT phosphorylation in HepG2 cells, while AD2-IFN-λ1 induced detectable phosphorylation at 0.1 nM concentration (not shown). In comparison, (15)-λ1 induced significantly greater phosphorylation of three STATs, particularly of STAT1, showing a signaling activity of 0.01 nM (15)-λ1 nearly equal to 0.1 nM AD2-IFN-λ1 (not shown). The enhanced STAT phosphorylation of (Fab)$_2$-IFN-λ1 versus AD2-IFN-λ was also demonstrated in (E1)-λ1-targeted ME-180 and (C2)-λ1-targeted A375 cells (data not shown).

The ability of (15)-λ1 to up-regulate the cell surface expression of MHC class I antigens (MHC-I) also was investigated in HepG2 cells by flow cytometry (not shown). Whereas treatment of HepG2 cells with hMN-15-Fab-DDD2 up to 1 nM for three days gave no change in the surface levels of MHC-1 (MFI ~50), a more than 3-fold increase in MFI (~170) was observed in cells treated with (15)-λ1 as low as 1 pM. The expression of MHC-1 reached a maximal level (MFI~270) with (15)-λ1 at 100 pM. Although AD2-IFN-λ1 was capable of up-regulating MHC-1, it required a higher concentration (100 pM) to be effective (not shown).

We also examined the capability of (15)-λ1 to induce the expression of the myxovirus resistance A (MxA) gene, a reliable marker for IFN bioactivity, and the results were determined by RT-PCR. In untreated or hMN-15-Fab-DDD2-treated HepG2 cells, the mRNAs of MxA were undetectable by RT-PCR (not shown). The induction of the MxA gene was evident in cells treated with 0.1 pM of (15)-λ1 or 10 pM of AD2-IFN-λ1 (not shown), thus further attesting to the advantage of (15)λ1 over AD2-IFN-λ1 in particular, and 2(Fab)-λ1 over IFN-λ1 in general.

Pharmacokinetics in Mice. After a single dose (2.4 nmol) of subcutaneous administration, the mean serum concentration of intact (E1)-λ1 reached a high level by 6 h and fell below the limit of ELISA detection by 48 h (not shown). The pharmacokinetic (PK) parameters derived from noncompartmental analysis demonstrate a mean residence time of 12 h with a $T_{1/2}$ of 8.6 h, and clearance of 2.2 ml/h. When the concentrations of (E1)-λ1 in the serum sample were also measured by its inhibitory activity on ME-180 cells using the MTS assay, the results were largely consistent (not shown).

Recombinant IFN-α has a very rapid rate of clearance in mice, showing a mean residence time of only 0.7 h. Thus, 2(Fab)-λ1 demonstrates a significantly improved PK that is comparable to PEG-IFN-α [37] and PEG-IFN-λ (not shown).

Discussion

The type III interferons (IFNs), comprising IFN-1, IFN-λ2, and IFN-λ3, behave similarly to IFN-α in eliciting antiviral, antitumor, and immune-modulating activities. Due to their more restricted cellular targets, IFN-λs are attractive as potential alternatives to existing therapeutic regimens based on IFN-αs. We produced DOCK-AND-LOCK™ complexes comprising antibody-conjugated IFN-λ1 to improve the antiproliferative potency of IFN-λ1 up to 1,000-fold in targeted cancer cell lines by tethering stabilized Fab dimers, derived from hRS7 (humanized anti-Trop-2), hMN-15 (humanized anti-CEACAM6), hL243 (humanized anti-HLA-DR), and c225 (chimeric anti-EGFR), to IFN-λ1 site-specifically, resulting in novel immunocytokines designated (E1)-λ1, (15)-λ1, (C2)-λ1, and (c225)-λ1, respectively. Targeted delivery of IFN-λ1 via (15)-λ1 or (c225)-λ1 to respective antigen-expressing cells also significantly increased anti-viral activity when compared with non-targeting (C2)-λ1, as demonstrated in human lung adenocarcinoma epithelial cell line A549 by (15)-λ1 against encephalomyocarditis virus ($EC_{50}$=22.2 pM versus 223 pM), and in human hepatocarcinoma cell line Huh-7 by (c225)-λ1 against hepatitis C virus ($EC_{50}$=0.56 pM versus 91.2 pM). These surprising and unexpected results are attributed to better localization and stronger binding of IFN-λ1 to antibody-targeted cells, together with the favorable pharmacokinetic profile of (E1)-λ1 in mice ($T_{1/2}$=8.6 h).

Trop-2 and CEACAM6 are expressed at higher levels than the receptors for IFN-λ1 on target cells (not shown). As a result, 10-fold more molecules of IFN-λ1 can be bound to target cells with the DNL conjugates. The co-ligation of Trop-2 or CEACAM6 with the heterodimeric receptors of IFN-λ1 may also increase the binding strength of IFN-λ1 nearly 100-fold as shown for (E1)-λ1 in ME-180. The targeted delivery of immunoconjugated IFN-λ1 provides significantly greater bioactivity for both tumor and infectious disease therapy than separately administered antibody and interferon, either alone or in combination.

The potential of TN-λ as a therapeutic alternative to IFN-α is being explored with PEG-IFN-λ1, which shows an improved safety profile over PEG-IFN-α-2a in clinical studies (Miller et al., 2009, Ann N Y Acad Sci 1182:80-87; Ramos, 2010, J Interferon Cytokine Res 30:591-95). However, rates of some serious adverse events, including dose-limiting hepatotoxicity, are similar for patients treated with PEG-IFN-λ1 and PEG-IFN-α-2a, and even more frequent in patients treated with the highest dose of PEG-TN-λ1 (Zeuzem et al., 2011, J Hepatology 54:5538-38). On the other hand, IFN-λs were less effective than type I IFNs against certain cancers (Meager et al., 2005, Cytokine 31:109-18) or viruses (Ank et al., 2006, J Interferon Cytokine Res 26:373-79). We postulated that linking IFN-λs to an antibody specific for an abundantly expressed surface antigen could enhance its localization at the target cells, resulting in greater potency and, hopefully, less toxicity to non-target cells. Accordingly, we developed four prototypes of IFN-λ-based immunocytokines, each comprising TN-λ1 conjugated site-specifically to a stabilized dimer of Fab, and demonstrated their superiority compared to the unconjugated parental modules alone or in combination. The improved effects were shown in both antitumor and antiviral assays, and are consistent with enhanced cell-surface binding and signal transduction, which are enabled by the constitutive antibody.

In the antitumor studies, we established ME-180 as the most sensitive cell line to IFN-λ1, with over 80% maximum inhibition and a 20-fold lower $EC_{50}$ than other cell lines reported in the literature (Zitzman et al., 2006, BBRC 344:1334-41; Meager et al., 2005, Cytokine 31:109-18; Maher et al., 2-8, Cancer Biol Ther 7:1109-15; Guenterberg et al., 2010, Mol Cancer Ther 9:510-20). Moreover, the abundant expression of Trop-2 on ME-180 renders these tumor cells highly sensitive to (E1)-λ1, with growth inhibition detectable at 1 fM and an $EC_{50}$ (<0.1 pM) 1000-fold lower than AD2-IFN-λ1 ($EC_{50}$~100 pM). Similar enhancements of inhibitory potency also were observed in TE-11, SK-MES-1, and other cancer cell lines. Because IFN-λs also induce innate and adaptive immune responses, which were not evaluated here, and in view of recent studies showing that the constitutive expression of IFN-λ in several murine cancer cell lines, including B16 melanoma, BNL hepatoma, and MCA205 fibrosarcoma, despite the lack of in vitro antiproliferative activity, markedly suppressed tumor growth and metastasis in syngeneic mouse models by recruiting immune cells and related cytokines (Numasaki et al., 2007, J Immunol 178:5086-98; Abushahba et al., 2010, Cancer Immunol Immunother 59:1059-71; Lasfar et al., 2006, Cancer Res 66:4468-77), we posit that targeted delivery of IFN-λ will resemble constitutive expression of IFN-λ in cancer cells, resulting in a local immune response and enhanced cytotoxicity in the immunotherapy of cancer (Pardoll and Drake, 2012, J Exp Med 209:201-9).

In the antiviral studies, the specific targeting of (c225)-λ1 to EGFR-positive Huh-7 cells hosting HCV genotype 1b Con1 replicon exhibited 123- and 163-fold enhancement of antiviral potency over non-targeting rhIFN-λ1 and (C2)-λ1, respectively. In another assay, the targeting of (15)-λ1 to CEACAM6-positive A549 cells challenged with EMCV exhibited 6- and 10-fold improvement of antiviral protection over the non-targeting rhIFN-λ1 and (C2)-λ1, respectively. The difference in potency between (c225)-λ1 and (15)-λ1 is likely due to the distinct sensitivity of their targeted cell/virus systems to IFN-λ1. In a previous study (Marcello et al., 2006, Gastroenterol 131:1887-98), rhIFN-λ1 was 10-fold less potent than rhIFN-α in the Huh-7/HCV system, but it is 210-fold less potent in A549/EMCV (Meager et al., 2005, Cytokine 31:109-18). Although the enhancement of (15)-21-induced antiviral activity is not as high in target cells, compared to (c225)-λ1, it is still a significant finding, considering that pegylated IFNs only retain about 30% or less activity of unpegylated IFNs (Grace et al., 2005, J Biol Chem 280:6327-36), and the specific activity of AD2-IFN-λ1 was similar to rhIFN-λ1. Thus, 2(Fab)-λ1 may allow a lower dose with the same or less frequent dosing schedule than the PEG-IFN-λ1 used in current clinical studies.

As a therapeutic agent, recombinant IFN is limited by its very rapid rate of clearance. Based on our previous study, recombinant IFN-α-2b, PEG-IFN-α-2a, and PEG-IFN-α-2b exhibited a half-life of 0.7, 14.9, and 9.3 h, respectively (Rossi et al., 2009, Blood 114:3864-71). Thus, a comparable half-life of (E1)-21 in mice (8.6 h) to PEG-IFN-α is promising for in vivo therapeutic use.

Example 10

DNL Constructs of (Fab)$_2$-Interferon-λ1 for Treatment of Alzheimer's Disease

Alzheimer's disease (AD) is a degenerative brain disorder characterized clinically by progressive memory deficits, confusion, gradual physical deterioration and, ultimately, death. Approximately 15 million people worldwide are affected by Alzheimer's disease. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP).

Aβ appears to have a central role in the neuropathology of Alzheimer's disease. Familial forms of the disease have been linked to mutations in APP and the presenilin genes (Tanzi et al., 1996, Neurobiol. Dis. 3:159-168; Hardy, 1996, Ann. Med. 28:255-258). Diseased-linked mutations in these genes result in increased production of the 42-amino acid form of Aβ, the predominant form found in amyloid plaques. Immunization of transgenic mice that overexpress a disease-linked mutant form of APP with human Aβ reduces plaque burden and associated pathologies (Schenk et al., 1999, Nature 400:173-177; WO 99/27944). Peripheral administration of antibodies directed against Aβ also reduces plaque burden in the brain (Bard et al., 2000, Nature Medicine 6(8):916-919; WO 2004/032868; WO 00/72880).

Antibody therapy provides a promising approach to the treatment and prevention of Alzheimer's disease. However, human clinical trials with a vaccine including A131-42 were suspended due to meningoencephalitis in a subset of patients. Orgogozo et al., Nerulogy 61:7-8 (2003); Ferrer et al., Brain Pathol. 14:11-20 (2004). Passive immunization with an N-terminal specific anti-Aβ antibody resulted in a significant reduction of diffuse amyloid, but increased cerebral microhemorrhage frequency in transgenic mice. Pfeifer et al., Science 298:1379 (2002). There remains a need for improved antibodies and/or immunoconjugates for treatment of Alzheimer's disease, with reduced toxicity.

A DNL™ complex comprising alemtuzumab attached to interferon-λ1 is prepared according to Example 9. The interferon-antibody complex is administered i.v. to human patients diagnosed with Alzheimer's disease at a dosage of 2 mg, twice weekly, for 4, 8 or 12 weeks. Efficacy is measured by neuropsychological testing, which includes the ADAS-cog and the CERAD neuropsychological test battery.

A slight (15%) improvement in ADAS-cog is observed after 12 weeks of treatment in all patients except the lowest dosage treatment group. Similar findings are observed for the Mini-Mental State Examination (MMSE). Visual construction abilities are improved in four out of ten patients. No serious adverse effects of interferon-antibody administration are observed.

A DNL™ complex comprising milatuzumab (anti-CD74 humanized IgG), or its Fab fragment attached to interferon-λ1 is prepared according to Example 9. This complex is administered i.v. to a 75-year-old woman with early Alzheimer's disease at twice weekly doses of 2 mg for 8 weeks. Some evidence of minor nausea and hypotension is noted after each infusion, which abates over the next 3 days. Efficacy is measured by cognitive skills testing (ADAS-cog) and the CERAD neuropsychological battery, at baseline and at weeks 2 and 8 post-therapy. The results indicate a 20% improvement in cognitive skills and general psychological and communicative status. The treatment is repeated 4 months later, is well-tolerated, and the patient shows maintenance of the improvement of cognitive skills, including visual construction abilities.

A DNL™ complex comprising hL243 (anti-HLA-DR humanized IgG), or its Fab fragment attached to interferon-λ1 is prepared according to Example 9. This complex is administered i.v. to a 82-year-old woman with Alzheimer's disease at twice weekly doses of 1 mg for 8 weeks. Some evidence of minor nausea and hypotension is noted after each infusion, which abates over the next 3 days. Efficacy is measured by cognitive skills testing (ADAS-cog) and the CERAD neuropsychological battery, at baseline and at weeks 2 and 8 post-therapy. The results indicate a 17% improvement in cognitive skills and general psychological and communicative status. The treatment is repeated 4 months later, is well-tolerated, and the patient shows maintenance of the improvement of cognitive skills, including visual construction abilities.

Example 11

DNL Constructs of (Fab)$_2$-Interferon-λ1 for Treatment of Asthma

Asthma is a heterogeneous family of diseases, characterized by hyper-responsiveness of the tracheobronchi to stimuli. Clinically, asthma is manifested by the extensive narrowing of the tracheobronchi, by thick tenacious secretions, by paroxysms of dyspnea, cough, and wheezing, resulting in an increase in airway resistance, hyperinflation of the lungs and thorax, abnormal distribution of ventilation and pulmonary blood flow. The disease is manifested in episodic periods of acute symptoms interspersed between symptom-free periods. The acute episodes result in hypoxia, and can be fatal. Approximately 3% of the general world population suffers from the disease. Asthma symptoms may be exacerbated by the presence and level of the triggering antigen, environmental factors, occupational factors, physical exertion, and emotional stress. Although asthma may be treated with methylxanthines (such as theophylline), beta-adrenergic agonists (such as catecholamines, resorcinols, saligenins, and ephedrine), glucocorticoids (such as hydrocortisone), inhibitors of mast cell degranulation (i.e. chromones such as cromolyn sodium) and anticholinergics (such as stropine), improved methods and compositions for treating asthma are needed.

An 80-year-old male bronchial asthmatic patient develops a cold with acute exacerbation of his asthma, with frequent cough producing large amounts of thick, yellow mucin. He is administered (15)-λ1 by aerosol inhalation twice daily over 6 days. The antibody-interferon complex is prepared as described in Example 9. Within a few hours of his first inhalation, his breathing is markedly improved, with infrequent cough. At the conclusion of this therapy course, his condition under physical exertion appears to be improved, as is his emotional status, since his breathing has had an improvement and there is a notable reduction in mucinous coughing.

Example 12

DNL Constructs of (Fab)$_2$-Interferon-λ1 for Treatment of Multiple Sclerosis

Multiple sclerosis (MS) is an autoimmune disease in which autoreactive T cells cross the blood-brain barrier and attack the myelin sheath, leading to inflammation and resulting in demyelination and axonal degeneration. Unpredictable episodes of neurological disability in young adults are followed by the accumulation of physical and cognitive disabilities in either discrete attacks (relapsing forms) or gradually over time. Although there is no known cure, interferon-β therapy is now the front-line treatment for relapsing remitting multiple sclerosis, with demonstrated efficacy in terms of decreased relapse rates. However, IFN therapy is associated with significant morbidity, with side effects such as influenza-like symptoms, myelosuppression, development or exacerbation of autoimmune disease, neutropenia, thrombocytopenia and neuropsychiatric effects.

A DNL™ complex comprising alemtuzumab attached to interferon-λ1 is prepared as disclosed in Example 9. The complex is administered at 2 mg every four weeks to a 64-year-old woman with relapsing multiple sclerosis (RMS). After 12 months of treatment, there is a decrease in annualized relapse rates and a reduced risk of sustained progression of disability observed with the complex. Compared to baseline measurements, significantly fewer gadolinium-enhancing lesions per T1-weighted MRI scan are noted. Side effects include grade-1/2 infusion reactions, grade 1 hypotension, and some hypersensitivity, all controlled well by corticosteroids.

What is claimed is:

1. A composition comprising:
a) a first fusion protein comprising interferon-λ attached to an anchor domain (AD) moiety from an AKAP (A-kinase anchoring protein), wherein the first fusion protein has an amino acid sequence selected from the group consisting of SEQ ID NO:96 and SEQ ID NO:97; and
b) a second fusion protein comprising an antibody or antigen-binding fragment thereof attached to a dimerization and docking domain (DDD) moiety from human protein kinase A (PKA) RIIα; and
wherein two copies of the DDD moiety form a dimer that binds to the AD moiety to form the complex.

2. The composition of claim 1, wherein the antibody or antibody fragment binds to an antigen selected from the group consisting of carbonic anhydrase IX, CCCL19 (C-C motif chemokine ligand 19), CCCL21, CSAp (colon-specific antigen-p), CD1(cluster of differentiation 1), CD1a, CD2, CD3, CD4, CD5, CD8, CD11A, CD14, CD15, CD16, CD18, CD19, IGF-1R (insulin-like growth factor 1 receptor), CD20, CD21, CD22, CD23, CD25, CD29, CD30, CD32b, CD33, CD37, CD38, CD40, CD40L , CD45, CD46, CD52, CD54, CD55, CD59, CD64, CD66a-e, CD67, CD70, CD74, CD79a , CD80, CD83, CD95, CD126, CD133, CD138, CD147, CD154, AFP (alpha fetoprotein), PSMA (prostate-specific membrane antigen), CEACAM5 (carcinoembryonic antigen-related cell adhesion molecule 5), CEACAM-6, B7 (B-cell activation antigen), ED-B (extradomain B) of fibronectin, Factor H, FHL-1 (four and a half LIM domains protein 1), Flt-3 (Fms-like tyrosine kinase 3), folate receptor, GRO-β (growth regulatory oncogene beta), HMGB-1 (high mobility group protein B 1), hypoxia inducible factor (HIF), HM 1.24, insulin-like growth factor-1 (ILGF-1), IFN-γ (interferon-gamma), IFN-α, IFN-β, IL-2 (interleukin-2), IL-4R (interleukin-4 receptor), IL-6R, IL-13R, IL-15R, IL-17R, IL-18R, IL-6, IL-8, IL-12, IL-15, IL-17, IL-18, IL-25, IP-10 (interferon gamma-induced protein 10), MAGE (melanoma antigen), mCRP (modified C-reactive protein), MCP-1 (monocyte chemoattractant protein-1), MIP-1A (macrophage inflammatory protein-1A), MIP-1B, MIF (macrophage migration inhibitory factor), MUC1 (mucin 1), MUC2, MUC3, MUC4, MUC5ac, PAM4 antigen, NCA-95 (normal glycoprotein crossreacting with CEA-95), NCA-90, Ia (immune-response associated), HM1.24 (CD317), EGP-1 (epithelial/carcinoma antigen-1), EGP-2, HLA-DR (human leukocyte antigen-DR), tenascin, Le(y) (Lewis antigen y), RANTES (regulated on activation, normal T cell expressed and secreted), TAC (T-cell activation), Tn (Thomsen-nouvelle) antigen, Thomson-Friedenreich antigens, tumor necrosis antigens, TNF-α (tumor necrosis factor-alpha), TRAIL (TNF-related apoptosis-inducing ligand) receptor (R1 and R2), VEGFR (vascular endothelial growth factor receptor), EGFR (epidermal growth factor receptor), PlGF (placental growth factor), complement factors C3, C3a, C3b, C5a, C5, and an oncogene product.

3. The composition of claim 1, wherein the antibody or antibody fragment binds to an antigen selected from the group consisting of TROP-2 (trophoblast cell-surface marker), CEACAM5, CEACAM6, HLA-DR, CD19, CD20, CD22, CD74, CD52, and EGFR.

4. The composition of claim 1, wherein the antibody or antibody fragment thereof is selected from the group consisting of hLL1, hLL2, RFB4, hRS7, hPAM4, hMN-3, hMN-14, hMN-15, hMu-9, Immu-31, hL243, hA19, hA20 and hR1.

5. The composition of claim 1, wherein the antibody fragment is selected from the group consisting of Fab, Fv, scFv and dAb.

6. The composition of claim 1, further comprising an additional therapeutic agent selected from the group consisting of a second antibody, a second antibody fragment, a drug, a toxin, an enzyme, a hormone, an immunomodulator, a cytokine, a chemokine, an antisense oligonucleotide, siRNA, RNAi, a radionuclide, a boron compound, a photoactive agent, an anti-angiogenic agent and a pro-apoptotic agent.

* * * * *

SEQUENCE LISTING

<160> NUMBER OF SEQ ID NOS: 100

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15
```

-continued

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
                20                  25                  30

Pro Met Lys Phe Leu Arg Glu His Phe Glu Lys Leu Glu Lys Glu Glu
            35                  40                  45

Asn Arg Gln Ile Leu Ala
        50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
            35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
            35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala

```
                    20                  25                  30

Val Glu Tyr Phe Thr Arg Leu Arg Glu Ala Arg Ala
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15
```

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

```
Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
```

```
                1               5                  10                  15
Thr Val Glu Val Leu Arg Gln Asn Pro Pro Asp Leu Val Glu Phe Ala
                20                  25                  30

Val Glu Tyr Phe Thr Arg Leu Arg Glu Ala Arg Ala
            35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                  10                  15

Thr Val Glu Val Leu Arg Gln Gln Pro Pro Glu Leu Val Glu Phe Ala
                20                  25                  30

Val Glu Tyr Phe Thr Arg Leu Arg Glu Ala Arg Ala
            35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                  10                  15

Thr Val Glu Val Leu Arg Gln Gln Pro Pro Asp Leu Val Asp Phe Ala
                20                  25                  30

Val Glu Tyr Phe Thr Arg Leu Arg Glu Ala Arg Ala
            35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                  10                  15

Thr Val Glu Val Leu Arg Gln Gln Pro Pro Asp Leu Val Glu Phe Leu
                20                  25                  30

Val Glu Tyr Phe Thr Arg Leu Arg Glu Ala Arg Ala
            35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

```
Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
                20                  25                  30

Val Glu Tyr Phe Thr Arg Leu Arg Glu Ala Arg Ala
            35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
                20                  25                  30

Val Glu Tyr Phe Thr Arg Leu Arg Glu Ala Arg Ala
            35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Asp Tyr Phe Thr Arg Leu Arg Glu Ala Arg Ala
            35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15
```

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gln Ile Glu Tyr Leu Ala Lys Gln Ile Val Asp Gln Ala Ile Gln Gln
1               5                   10                  15
Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gln Ile Glu Tyr Leu Ala Lys Gln Ile Val Asp Asn Ala Ile Asn Gln
1               5                   10                  15
Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gln Ile Glu Tyr Leu Ala Lys Gln Ile Val Asp Asn Ala Ile Gln Asn
1               5                   10                  15
Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gln Ile Glu Tyr Leu Ala Lys Gln Ile Val Asp Asn Ala Ile Gln Gln
1               5                   10                  15
Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25
```

```
<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
```

```
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
            145                 150                 155                 160
        Tyr Val Asp Gly Val Glu Val His Asn Ala Lys Thr Lys Pro Arg Glu
                        165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
                        210                 215                 220

Gln Pro Arg Glu Pro Gln Val Tyr Thr Leu Pro Pro Ser Arg Glu Glu
        225                 230                 235                 240

Met Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                        290                 295                 300

Val Phe Ser Cys Ser Val Met His Glu Ala Leu His Asn His Tyr Thr
        305                 310                 315                 320

Gln Lys Ser Leu Ser Leu Ser Pro Gly Lys
                        325                 330

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
```

```
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 87

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

-continued

```
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1               5                   10                  15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
```

```
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agatctggcg cacctgaact cctg                                          24

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gaattcggat cctttacccg gagacaggga gag                                33

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5
```

```
<210> SEQ ID NO 93
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Lys Ser His His His His His His Gly Ser Gly Gly Gly Ser Gly
1               5                   10                  15

Gly Gly Cys Gly His Ile Gln Ile Pro Pro Gly Leu Thr Glu Leu Leu
            20                  25                  30

Gln Gly Tyr Thr Val Glu Val Leu Arg Gln Gln Pro Asp Leu Val
        35                  40                  45

Glu Phe Ala Val Glu Tyr Phe Thr Arg Leu Arg Glu Ala Arg Ala
    50                  55                  60

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tctagacaca ggacctcatc atggccttga cctttgcttt actgg              45

<210> SEQ ID NO 95
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ggatccatga tggtgatgat ggtgtgactt ttccttactt cttaaacttt cttgc    55

<210> SEQ ID NO 96
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Cys Gly Gln Ile Glu Tyr Leu Ala Lys Gln Ile Val Asp Asn Ala
1               5                   10                  15

Ile Gln Gln Ala Gly Cys Glu Phe Pro Lys Pro Ser Thr Pro Pro Gly
            20                  25                  30

Ser Ser Gly Gly Ala Pro Ala Met Asp Gly Pro Val Pro Thr Ser Lys
        35                  40                  45

Pro Thr Thr Thr Gly Lys Gly Cys His Ile Gly Arg Phe Lys Ser Leu
    50                  55                  60

Ser Pro Gln Glu Leu Ala Ser Phe Lys Lys Ala Arg Asp Ala Leu Glu
65                  70                  75                  80

Glu Ser Leu Lys Leu Lys Asn Trp Ser Cys Ser Ser Pro Val Phe Pro
                85                  90                  95

Gly Asn Trp Asp Leu Arg Leu Leu Gln Val Arg Glu Arg Pro Val Ala
            100                 105                 110
```

```
Leu Glu Ala Glu Leu Ala Leu Thr Leu Lys Val Leu Glu Ala Ala Ala
            115                 120                 125

Gly Pro Ala Leu Glu Asp Val Leu Asp Gln Pro Leu His Thr Leu His
        130                 135                 140

His Ile Leu Ser Gln Leu Gln Ala Cys Ile Gln Pro Gln Pro Thr Ala
145                 150                 155                 160

Gly Pro Arg Pro Arg Gly Arg Leu His His Trp Leu His Arg Leu Gln
                165                 170                 175

Glu Ala Pro Lys Lys Glu Ser Ala Gly Cys Leu Glu Ala Ser Val Thr
            180                 185                 190

Phe Asn Leu Phe Arg Leu Leu Thr Arg Asp Leu Lys Tyr Val Ala Asp
        195                 200                 205

Gly Asn Leu Cys Leu Arg Thr Ser Thr His Pro Glu Ser Thr Val Glu
210                 215                 220

His His His His His His
225                 230
```

<210> SEQ ID NO 97
<211> LENGTH: 230
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 97

```
Met Cys Gly Gln Ile Glu Tyr Leu Ala Lys Gln Ile Val Asp Asn Ala
1               5                   10                  15

Ile Gln Gln Ala Gly Cys Glu Phe Pro Lys Pro Ser Thr Pro Pro Gly
            20                  25                  30

Ser Ser Gly Gly Ala Pro Ala Met Asp Gly Pro Val Pro Thr Ser Lys
        35                  40                  45

Pro Thr Thr Thr Gly Lys Gly Cys His Ile Gly Arg Phe Lys Ser Leu
50                  55                  60

Ser Pro Gln Glu Leu Ala Ser Phe Lys Lys Ala Arg Asp Ala Leu Glu
65                  70                  75                  80

Glu Ser Leu Lys Leu Lys Asn Trp Ser Cys Ser Ser Pro Val Phe Pro
            85                  90                  95

Gly Asn Trp Asp Leu Arg Leu Leu Gln Val Arg Glu Arg Pro Val Ala
        100                 105                 110

Leu Glu Ala Glu Leu Ala Leu Thr Leu Lys Val Leu Glu Ala Ala Ala
            115                 120                 125

Gly Pro Ala Leu Glu Asp Val Leu Asp Gln Pro Leu His Thr Leu His
        130                 135                 140

His Ile Leu Ser Gln Leu Gln Ala Cys Ile Gln Pro Gln Pro Thr Ala
145                 150                 155                 160

Gly Pro Arg Pro Arg Gly Arg Leu His His Trp Leu His Arg Leu Gln
                165                 170                 175

Glu Ala Pro Lys Lys Glu Ser Ala Gly Cys Leu Glu Ala Ser Val Thr
            180                 185                 190

Phe Asn Leu Phe Arg Leu Leu Thr Arg Asp Leu Lys Tyr Val Ala Asp
        195                 200                 205

Gly Asn Leu Ser Leu Arg Thr Ser Thr His Pro Glu Ser Thr Val Glu
210                 215                 220

His His His His His His
```

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)
<220> FEATURE:
<223> OTHER INFORMATION: C-term NH2

<400> SEQUENCE: 98

Phe Lys Tyr Lys
1

<210> SEQ ID NO 99
<211> LENGTH: 99
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(96)

<400> SEQUENCE: 99 ccg gcg atg gcc atg gat atc gga att aat tcg gat ccg aat tcg agc    48
Pro Ala Met Ala Met Asp Ile Gly Ile Asn Ser Asp Pro Asn Ser Ser
1               5                   10                  15 tcc gtc gac aag ctt gcg gcc gca ctc gag cac cac cac cac cac cac    96
Ser Val Asp Lys Leu Ala Ala Ala Leu Glu His His His His His His
            20                  25                  30 tga                                                                99

<210> SEQ ID NO 100
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Pro Ala Met Ala Met Asp Ile Gly Ile Asn Ser Asp Pro Asn Ser Ser
1               5                   10                  15

Ser Val Asp Lys Leu Ala Ala Ala Leu Glu His His His His His His
            20                  25                  30